(12) United States Patent
Osterhout et al.

(10) Patent No.: US 10,059,967 B2
(45) Date of Patent: Aug. 28, 2018

(54) MICROORGANISMS AND PROCESSES FOR PRODUCING TEREPHTHALIC ACID AND ITS SALTS

(71) Applicant: Genomatica, Inc., San Diego, CA (US)

(72) Inventors: Robin E. Osterhout, San Diego, CA (US); Anthony P. Burgard, San Diego, CA (US); Mark J. Burk, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 222 days.

(21) Appl. No.: 14/373,160

(22) PCT Filed: Jan. 18, 2013

(86) PCT No.: PCT/US2013/022113
§ 371 (c)(1),
(2) Date: Jul. 18, 2014

(87) PCT Pub. No.: WO2013/109865
PCT Pub. Date: Jul. 25, 2013

(65) Prior Publication Data
US 2015/0080547 A1  Mar. 19, 2015

Related U.S. Application Data

(60) Provisional application No. 61/589,081, filed on Jan. 20, 2012, provisional application No. 61/598,743, filed on Feb. 14, 2012.

(51) Int. Cl.
| | | |
|---|---|---|
| *C12P 7/44* | (2006.01) | |
| *C12N 1/20* | (2006.01) | |
| *C12N 15/00* | (2006.01) | |
| *C12N 9/02* | (2006.01) | |
| *C12N 9/04* | (2006.01) | |
| *C12N 9/06* | (2006.01) | |
| *C12N 9/10* | (2006.01) | |
| *C12N 9/12* | (2006.01) | |
| *C12N 9/88* | (2006.01) | |
| *C08G 63/183* | (2006.01) | |
| *C12P 7/24* | (2006.01) | |
| *C12P 7/40* | (2006.01) | |
| *C12P 9/00* | (2006.01) | |
| *C07F 9/09* | (2006.01) | |
| *C07C 51/43* | (2006.01) | |
| *C12P 7/62* | (2006.01) | |

(52) U.S. Cl.
CPC .............. *C12P 7/44* (2013.01); *C07C 51/43* (2013.01); *C07F 9/091* (2013.01); *C08G 63/183* (2013.01); *C12N 9/0004* (2013.01); *C12N 9/0006* (2013.01); *C12N 9/0008* (2013.01); *C12N 9/1007* (2013.01); *C12N 9/1022* (2013.01); *C12N 9/1085* (2013.01); *C12N 9/1205* (2013.01); *C12N 9/88* (2013.01); *C12P 7/24* (2013.01); *C12P 7/40* (2013.01); *C12P 7/62* (2013.01); *C12P 9/00* (2013.01)

(58) Field of Classification Search
None
See application file for complete search history.

(56) References Cited

U.S. PATENT DOCUMENTS

| | | |
|---|---|---|
| 2,905,709 A | 9/1959 | Schenk et al. |
| 3,023,234 A | 2/1962 | Schutt et al. |
| 3,042,717 A | 7/1962 | Schenk |
| 3,043,846 A | 7/1962 | Blaser et al. |
| 3,064,041 A | 11/1962 | Blaser et al. |
| 3,096,366 A | 7/1963 | Smith et al. |
| 6,441,225 B1 | 8/2002 | Brownscombe |
| 7,127,379 B2 | 10/2006 | Palsson et al. |
| 2002/0012939 A1 | 1/2002 | Palsson |
| 2002/0168654 A1 | 11/2002 | Maranas et al. |
| 2003/0059792 A1 | 3/2003 | Palsson et al. |
| 2003/0224363 A1 | 12/2003 | Park et al. |
| 2003/0233218 A1 | 12/2003 | Schilling |
| 2004/0009466 A1 | 1/2004 | Maranas et al. |

(Continued)

FOREIGN PATENT DOCUMENTS

| | | |
|---|---|---|
| WO | 2002/055995 A2 | 7/2002 |
| WO | 2003/106998 A1 | 12/2003 |

(Continued)

OTHER PUBLICATIONS

Pang et al., "Review of Conventional and Novel Polymerization Process for Polyesters," Progress in Polymer Science, Pergamon Press, Oxford, GB, vol. 31, No. 11, Nov. 15, 2006, pp. 1009-1037.

(Continued)

*Primary Examiner* — Yong D Pak
(74) *Attorney, Agent, or Firm* — Kagan Binder, PLLC

(57) ABSTRACT

The invention provides non-naturally occurring microbial organisms having a (2-hydroxy-3-methyl-4-oxobutoxy) phosphonate (2H3M4OP) pathway, p-toluate pathway, and/or terephthalate pathway. The invention additionally provides methods of using such organisms to produce 2H3M4OP, p-toluate or terephthalate. Also provided herein are processes for isolating bio-based aromatic carboxylic acid, in particular, p-toluic acid or terephthalic acid, from a culture medium, wherein the processes involve contacting the culture medium with sufficient carbon dioxide ($CO_2$) to lower the pH of the culture medium to produce a precipitate comprised of the aromatic carboxylic acid.

1 Claim, 6 Drawing Sheets

(56) References Cited

U.S. PATENT DOCUMENTS

| | | |
|---|---|---|
| 2004/0029149 A1 | 2/2004 | Palsson et al. |
| 2004/0072723 A1 | 4/2004 | Palsson et al. |
| 2009/0047719 A1 | 2/2009 | Burgard et al. |
| 2011/0124911 A1 | 5/2011 | Burk et al. |
| 2011/0207185 A1* | 8/2011 | Osterhout ............ C12N 9/0006 435/131 |

FOREIGN PATENT DOCUMENTS

| | | |
|---|---|---|
| WO | 2009/120457 A2 | 10/2009 |
| WO | 2011/017560 A1 | 2/2011 |
| WO | 20111094131 A1 | 8/2011 |

OTHER PUBLICATIONS

Ekaterina A. Savrasova et al, "Use of the Valine Biosynthetic Pathway to Convert Glucose into Isobutanol," Journal of Industrial Microbiology & Biotechnology; Official Journal of the Society for Industrial Microbiology, Springer, Berlin, DE, vol. 36, No. 9, Dec. 15, 2010, pp. 1287-1294.

* cited by examiner

MICROORGANISMS AND PROCESSES FOR PRODUCING TEREPHTHALIC ACID AND ITS SALTS

This application claims the benefit of International Application No. PCT/US2013/022113 which was filed on Jan. 18, 2013, which claims the benefit of U.S. Provisional application Ser. No. 61/589,081, filed Jan. 20, 2012, and U.S. Provisional application Ser. No. 61/598,743, filed Feb. 14, 2012, the entire contents of which are incorporated herein by reference.

TECHNICAL FIELD

The present invention relates generally to biosynthetic processes, and more specifically to organisms having (2-hydroxy-3-methyl-4-oxobutoxy)phosphonate (2H3M4OP), p-toluate or terephthalate biosynthetic capability. Also provided herein are processes for isolating a bio-based aromatic carboxylic acid, for example, p-toluic acid or terephthalic acid, from a culture medium, wherein the processes involve lowering the pH of the culture medium to produce a precipitate comprised of the aromatic carboxylic acid.

BACKGROUND OF THE INVENTION

Terephthalate (also known as terephthalic acid and PTA) is the immediate precursor of polyethylene terephthalate (PET), used to make clothing, resins, plastic bottles and even as a poultry feed additive. Nearly all PTA is produced from para-xylene by oxidation in air in a process known as the Mid Century Process. This oxidation is conducted at high temperature in an acetic acid solvent with a catalyst composed of cobalt and/or manganese salts. Para-xylene is derived from petrochemical sources and is formed by high severity catalytic reforming of naphtha. Xylene is also obtained from the pyrolysis gasoline stream in a naphtha steam cracker and by toluene disproportion.

Cost-effective methods for generating renewable PTA have not yet been developed to date. PTA, toluene and other aromatic precursors are naturally degraded by some bacteria. However, these degradation pathways typically involve monooxygenases that operate irreversibly in the degradative direction. Hence, biosynthetic pathways for PTA are severely limited by the properties of known enzymes to date.

A promising precursor for PTA is p-toluate, also known as p-methylbenzoate. P-Toluate is an intermediate in some industrial processes for the oxidation of p-xylene to PTA. It is also an intermediate for polymer stabilizers, pesticides, light sensitive compounds, animal feed supplements and other organic chemicals. Only slightly soluble in aqueous solution, p-toluate is a solid at physiological temperatures, with a melting point of 275° C. Microbial catalysts for synthesizing this compound from sugar feedstocks have not been described to date.

Petrochemical based chemical syntheses for making terephthalic acid are known (see, e.g., U.S. Pat. Nos. 2,905,709; 3,023,234; 3,042,717; 3,043,846; 3,064,041; 3,096,366; and 6,441,225). Alternative technologies for the production of terephthalic acid have been made feasible with the advent of molecular recombinant technologies used to modify biosynthetic pathways in microbial organisms. For example, microbial organisms have been described which produce precursors useful for the synthesis of bio-based terephthalic acid. Exemplary indirect semi-synthetic routes of producing bio-based terephthalic acid are described in U.S. Patent Publication No. 2011/0124911 A1. Direct biosynthetic routes, wherein terephthalate is itself biosynthesized in microbial organisms have been described in U.S. Patent Publication No. 2011/0207185 A1. Even with advantages that bio-based production of terephthalic acid offers, improvements and/or additional processes are sought, for example, to improve recovery of terephthalic acid in terms of yields and purity, and to increase efficiency and scalability of the processes including, for instance, reducing the number of manufacturing steps, lowering energy usage, recapturing and recycling materials and reducing environmental discharges.

Thus, there exists a need for alternative methods for effectively producing and isolating commercial quantities of compounds such as p-toluate or terephthalate. The present invention satisfies this need and provides related advantages as well.

SUMMARY OF INVENTION

The invention provides non-naturally occurring microbial organisms having a 2H3M4OP pathway, p-toluate pathway, and/or terephthalate pathway. The invention additionally provides methods of using such organisms to produce 2H3M4OP, p-toluate or terephthalate.

The invention also provides a process for isolating a bio-based aromatic carboxylic acid from a culture medium. In certain embodiments, the process comprises the steps of: (a) culturing a non-naturally occurring microbial organism in a culture medium to produce an aromatic carboxylate anion at a pH sufficient to maintain the aromatic carboxylate anion in soluble form; (b) lowering the pH of the culture medium to produce an aromatic carboxylic acid precipitate from the aromatic carboxylate anion. In certain embodiments, lowering the pH of the culture medium comprises contacting the culture medium with carbon dioxide ($CO_2$). In certain embodiments, the culture medium is substantially depleted of the aromatic carboxylate anion. In certain embodiments, the process further comprises separating the culture medium from non-soluble materials, for example, cells, cell debris, cellulosic material, feed stock, etc., prior to lowering the pH. In certain embodiments, the process further comprises separating the aromatic carboxylic acid from the culture medium, for example, by centrifugation or membrane filtration, etc.

In certain embodiments of the isolation process, the aromatic carboxylic acid is p-toluic acid. In certain embodiments, the aromatic carboxylic acid is terephthalic acid.

In certain embodiments of the isolation process, a counter ion to the aromatic carboxylate anion in the culture medium is an ammonium, sodium or potassium cation. In certain embodiments, the counter ion is an ammonium cation.

In certain embodiments of the isolation process, the pH sufficient to maintain the aromatic carboxylate anion in soluble form is between about 5.0-9.0 pH units. In some embodiments, the pH is about 6.0 to about 8.0 pH units or about 6.2 to about 7.8 pH units. In certain embodiments, the pH sufficient to maintain the aromatic carboxylate anion in soluble form is about 7.0 pH units. In certain embodiments, base is added to the culture medium in the culturing step to maintain the aromatic carboxylate anion in soluble form. In certain embodiments, the base is ammonia.

In certain embodiments of the isolation process, when lowering the pH of the culture medium, the pH is lowered to less than about 5.0 pH units, less than about 4.5 pH units, less than about 4.0 pH units, less than about 3.5 pH units, less than about 3.0 pH units, less than about 2.5 pH units, less than about 2.0 pH units, less than about 1.5 pH units, or less than about 1.0 pH units. In certain embodiments, the pH of the culture medium following the first separation step is lowered to less than about 3.0 pH units. In certain embodiments, the pH is lowered in the culture medium following separation of culture medium from non-soluble materials such as cells, cell debris, feedstock, and the like, which, for example, can be present when culturing a non-naturally occurring microbial organism.

In certain embodiments of the isolation process, wherein the culture medium is contacted with $CO_2$, the $CO_2$ used in the contacting step is gaseous. In certain embodiments, the gaseous $CO_2$ is pure $CO_2$ gas. In certain embodiments, the gaseous $CO_2$ is in a mixture with one or more additional gases. In certain embodiments, the additional gas is nitrogen gas. In certain embodiments, $CO_2$ generated from the culturing step can be used to lower the pH of the culture medium.

In certain embodiments of the isolation process, the culture medium is contacted with $CO_2$ in the range of 0.1 to 30 atm. In certain embodiments, the culture medium is stirred at temperatures between 0° C. and 80° C. for up to 24 hours during this contacting step.

In certain embodiments of the isolation process, when present, the second separation step comprises filtering and recovering of the aromatic carboxylic acid from the culture medium.

In certain embodiments of the isolation process, the process further comprises purifying the separated aromatic carboxylic acid. In certain embodiments, the purification step comprises crystallizing the aromatic carboxylic acid.

In certain embodiments of the isolation process, the non-naturally occurring microbial organism produces p-toluate and the aromatic carboxylic acid is p-toluic acid.

In certain embodiments of the isolation process, the non-naturally occurring microbial organism produces terephthalate and the aromatic carboxylic acid is terephthalic acid.

In certain embodiments of the isolation process, the non-naturally occurring microbial organism has a 2H3M4OP pathway, p-toluate pathway, and/or terephthalate pathway.

In certain embodiments of the isolation process, the non-naturally occurring microbial organism produces muconate, and the process further comprises contacting muconate with acetylene to form a cyclohexadiene adduct, and oxidizing the cyclohexadiene adduct to form the aromatic carboxylate anion. In certain embodiments, wherein the non-naturally occurring microbial organism produces muconate, the process for isolating a bio-based aromatic carboxylic acid from a culture medium comprises the steps of: (a) culturing a non-naturally occurring microbial organism in a culture medium to produce muconate at a pH sufficient to maintain muconate in soluble form; (b) contacting muconate with acetylene to form a cyclohexadiene adduct; (c) oxidizing the cyclohexadiene adduct to form the aromatic carboxylate anion; and (d) contacting the culture medium with sufficient carbon dioxide ($CO_2$) to lower the pH of the culture medium to produce an aromatic carboxylic acid precipitate, wherein the culture medium is substantially depleted of the aromatic carboxylate anion. In certain embodiments, the process further comprises separating the culture medium from non-soluble materials, for example, cells, cell debris, cellulosic material, feed stock, etc., prior to lowering the pH. In certain embodiments, the process further comprises separating the aromatic carboxylic acid from the culture medium, for example, by centrifugation or membrane filtration, etc. In certain embodiments, the aromatic carboxylic acid is terephthalic acid.

In another aspect of the isolation process, an isolated aromatic carboxylic acid produced by the processes disclosed herein is provided. In certain embodiments, isolated bio-based p-toluic acid is produced. In certain embodiments, isolated bio-based terephthalic acid is produced.

Terephthalate produced by a microorganism or isolation process of the invention can be used as a precursor for production of a polymer, including polyethylene terephthalate (PET), polybutyl terephthalate (PBT) or polytrimethylene terephthalate (PTT). PET can be produced by reacting ethylene glycol with dimethyl terephthalate of the invention by transesterification or by reacting ethylene glycol with terephthalate of the invention by esterification. PBT can be produced by reacting 1,4-butanediol with terephthalate of the invention. PTT can be produced by reacting 1,3-propanediol with terephthalate of the invention. Accordingly, in certain embodiments, the invention provides PET, PBT or PTT comprising, obtained by or manufactured using the terephthalate produced by a microorganism of the invention or isolated by a process described herein. Furthermore, PET can be used to manufacture bulk materials such as, for example, chips (e.g. PET bottle chips), resins and fibers, which in turn can be used to make cloth, clothing and plastic bottles, or even used as a poultry feed additive. PBT can be used to manufacture several products, such as, for example, molded articles, injection-molded products, injection-molded parts, such as an automotive part, extrusion resins, electrical parts or casings. PTT can also be used to manufacture several products, including, for example, fibers, cloth, carpets or bottles.

In certain embodiments, the invention provides a process for obtaining PET by reacting ethylene glycol with dimethyl terephthalate, wherein the dimethyl terephthalate is produced from terephthalate produced by a microorganism of the invention or isolated by a process described herein. In another aspect, the invention provides a process for obtaining PET by reacting ethylene glycol with terephthalic acid, wherein the terephthalic acid is produced by a microorganism of the invention or isolated by a process described herein.

In certain embodiments, the invention provides a process for obtaining PBT by reacting 1,4-butanediol with terephthalate produced by a microorganism of the invention or isolated by a process described herein.

In certain embodiments, the invention provides a process for obtaining PTT by reacting 1,3-propanediol with terephthalate produced by a microorganism of the invention or isolated by a process described herein, or reacting 1,3-propanediol with dimethyl terephthalate, wherein the dimethyl terephthalate is produced from the terephthalate produced by a microorganism of the invention or isolated by a process described herein.

In certain embodiments, the invention provides a polyester fiber, a polyester cloth or a polyester carpet comprising, obtained by or manufactured using PET or PTT, wherein the PET or PTT comprises, was obtained by or was manufactured using the terephthalate produced by a microorganism of the invention or isolated by a process described herein.

In certain embodiments, the invention provides a chip comprising, obtained by or manufactured using PET or PTT, wherein the PET or PTT comprises, was obtained by or was manufactured using the terephthalate produced by a microorganism of the invention or isolated by a process described herein. In another aspect, the invention provides a PET or PTT bottle comprising, obtained by or manufactured using the chips described herein.

In certain embodiments, the invention provides a packaging container comprising, obtained by or manufactured using PET, wherein the PET comprises, was obtained by or was manufactured using the terephthalate produced by a microorganism of the invention or a process described herein.

In certain embodiments, the invention provides a film comprising, obtained by or manufactured using PET, wherein the PET comprises, was obtained by or was manufactured using the terephthalate produced by a microorganism of the invention or a process described herein.

In certain embodiments, the invention provides a molded article comprising, obtained by or manufactured using PET, PBT or PTT, wherein the PET, PBT or PTT comprises, was obtained by or was manufactured using the terephthalate produced by a microorganism of the invention or a process described herein.

DETAILED DESCRIPTION OF THE INVENTION

Figure 1:
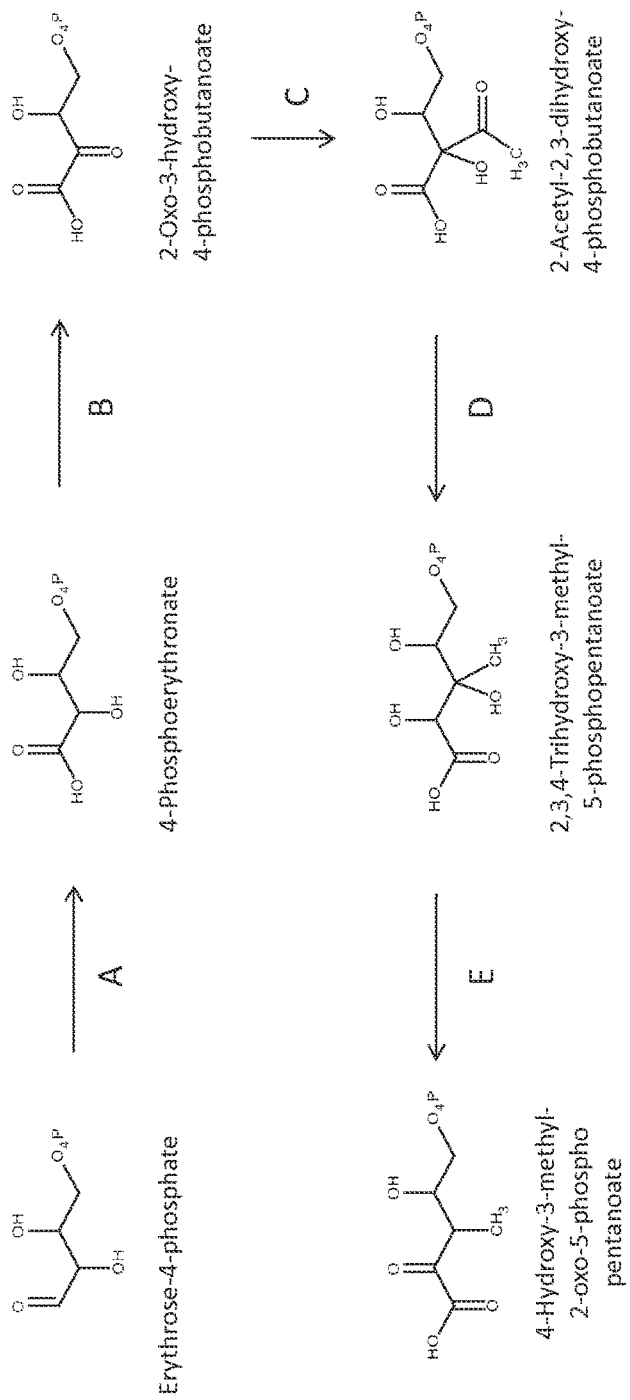
FIG. 1 shows a schematic depiction of an exemplary pathway from erythrose-4-phosphate to (2-hydroxy-3-methyl-4-oxobutoxy)phosphonate ("2H3M4OP"). In steps A-F, the enzymes can be: A. erythrose-4-phosphate dehydrogenase; B. 4-phosphoerythronate dehydrogenase; C. 2-acetyl-2,3-dihydroxy-4-phosphobutanoate synthase; D. 2-acetyl-2,3-dihydroxy-4-phosphobutanoate reductoisomerase; E. 2,3,4-trihydroxy-3-methyl-5-phosphopentanoate dehydratase; and F. 4-hydroxy-3-methyl-2-oxo-5-phosphopentanoate decarboxylase.

The present invention is directed to, at least in part, the design and production of cells and organisms having biosynthetic production capabilities for 2H3M4OP, p-toluate or terephthalate. The results described herein indicate that metabolic pathways can be designed and recombinantly engineered to achieve the biosynthesis of 2H3M4OP, p-toluate or terephthalate in *Escherichia coli* and other cells or organisms. Biosynthetic production of 2H3M4OP, p-toluate or terephthalate can be confirmed by construction of strains having the designed metabolic genotype. These metabolically engineered cells or organisms also can be subjected to adaptive evolution to further augment 2H3M4OP, p-toluate or terephthalate biosynthesis, including under conditions approaching theoretical maximum growth.

The shikimate biosynthesis pathway in *E. coli* converts erythrose-4-phosphate to chorismate, an important intermediate that leads to the biosynthesis of many essential metabolites including 4-hydroxybenzoate. 4-Hydroxybenzoate is structurally similar to p-toluate, an industrial precursor of terephthalic acid. As disclosed herein, shikimate pathway enzymes can be utilized to accept the alternate substrate, 2H3M4OP and transform it to p-toluate. In addition, various pathway enzymes can be used to synthesize the 2H3M4OP precursor from erythrose-4-phosphate using enzymes for P5C biosynthesis and enzymes analogous to the isoleucine biosynthesis pathway, or alternatively from 4,5-dihydroxy-2-oxopentanoate using a methyl transferase, a kinase and a decarboxylase. Synthesis of the 2H3M4OP precursor from glyceraldehydes-3-phosphate and pyruvate can also be done using enzymes from the non-mevalonate pathway for isoprenoid biosynthesis.

Disclosed herein are strategies for engineering a microorganism to produce renewable p-toluate or terephthalate (PTA) from carbohydrate feedstocks. The substrate 4,5-dihydroxy-2-oxopentanoate is naturally derived from sugars such as arabinose and xylose. Additionally, this substrate can be formed enzymatically by condensation of pyruvate and glycolaldehyde by aldolase enzymes such as 2-dehydro-3-deoxypentonate aldolase, 2-dehydro-3-deoxyglucarate aldolase, or other enzymes in EC class 4.1.2 or 4.1.3. The substrate erythrose-4-phosphate is an intermediate in the pentose phosphate pathway and the Calvin cycle. Additionally, erythrose-4-phosphate can serve as a precursor to the biosynthesis of the aromatic amino acids tyrosine, phenylalanine and tryptophan. First, erythrose-4-phosphate can be converted to 2H3M4OP in six enzymatic steps (see Example I and FIG. 1). In one alternative, 4,5-dihydroxy-2-oxopentanoate is converted to 2H3M4OP using one or both of the pathways described in Example I and FIG. 2. In another alternative, glyceraldehyde-3-phosphate (G3P) and pyruvate are converted to 2H3M4OP in three enzymatic steps (see Example II and FIG. 3). The 2H3M4OP intermediate can be subsequently transformed to p-toluate by enzymes in the shikimate pathway (see Example III and FIG. 4). p-Toluate can be further converted to PTA (terephthalate) by a microorganism (see Example IV and FIG. 5).

Figure 6:
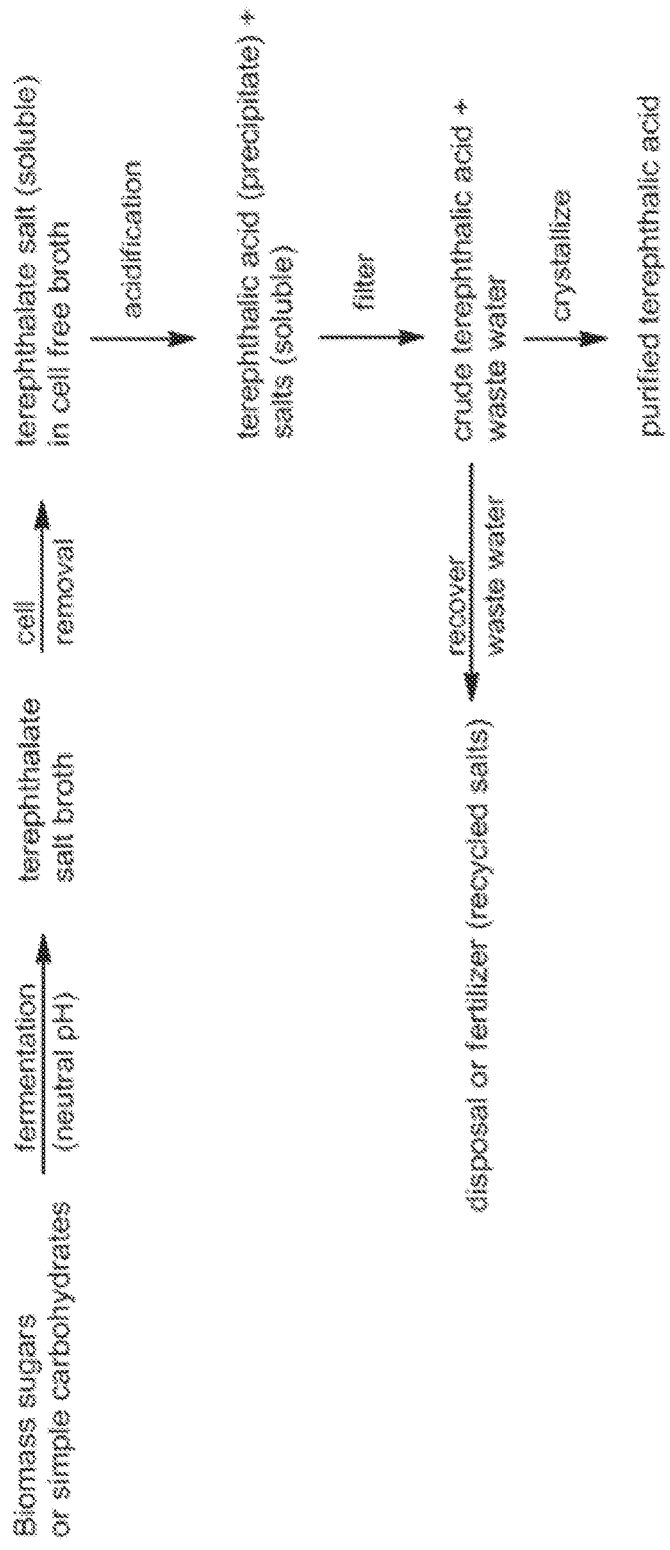
FIG. 6 depicts an exemplary process for preparing bio-based terephthalic acid.

The purification method of the invention, e.g. exemplified in FIG. 6, can also be applied to biosynthetic pathways for aromatic carboxylic acid and terephthalic acid production described in WIPO patent publications WO/2009/120457A2 entitled "Bio-Based Polyethylene Terephthalate Polymer And Method Of Making The Same", WO/2011/094131A1 entitled "Microorganisms And Methods For The Biosynthesis Of P-Toluate And Terephthalate", and WO/2011/017560A1 entitled "Semi-Synthetic Terephthalic Acid Via Microorganisms That Produce Muconic Acid" and U.S. Pat. No. 6,461,840 entitled "Terephthalic acid producing proteobacteria" and U.S. Pat. No. 6,187,569 entitled "Microbial production of terephthalic acid and isophthalic acid."

Figure 4:
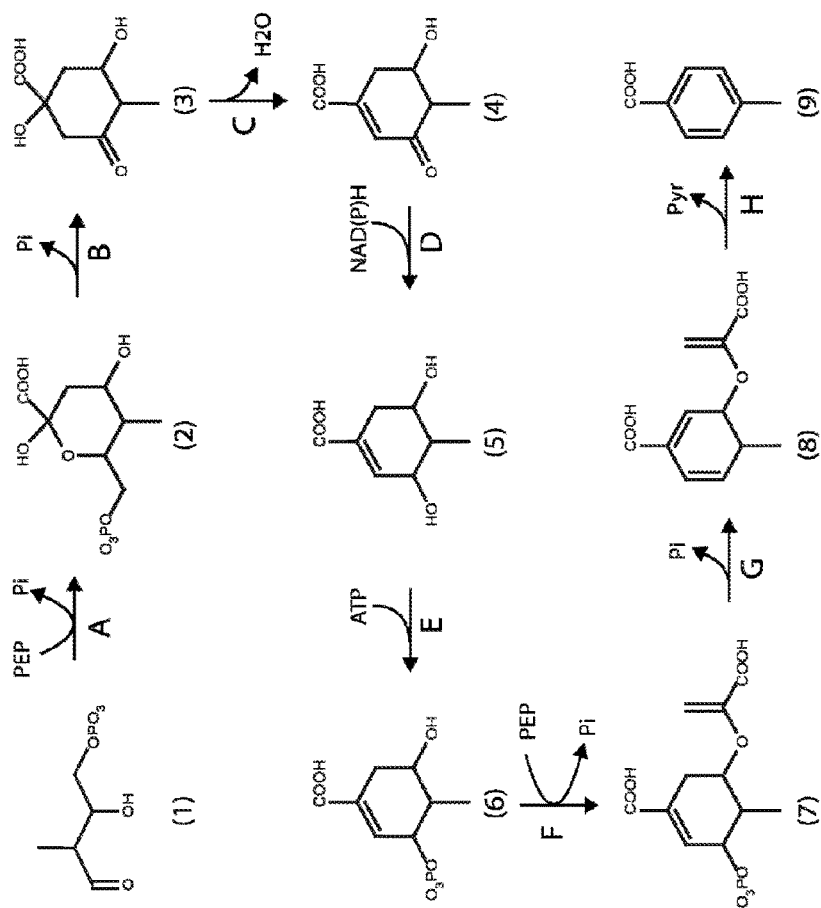
FIG. 4 shows a schematic depiction of an exemplary alternate shikimate pathway to p-toluate. In steps A-H, the enzymes can be: A. 2-dehydro-3-deoxyphosphoheptonate synthase; B. 3-dehydroquinate synthase; C. 3-dehydroquinate dehydratase; D. shikimate dehydrogenase; E. Shikimate kinase; F. 3-phosphoshikimate-2-carboxyvinyltransferase; G. chorismate synthase; and H. chorismate lyase. Compounds are: (1) (2-hydroxy-3-methyl-4-oxobutoxy)phosphonate; (2) 2,4-dihydroxy-5-methyl-6-[(phosphonooxy)methyl]oxane-2-carboxylate; (3) 1,3-dihydroxy-4-methyl-5-oxocyclohexane-1-carboxylate; (4) 5-hydroxy-4-methyl-3-oxocyclohex-1-ene-1-carboxylate; (5) 3,5-dihydroxy-4-methylcyclohex-1-ene-1-carboxylate; (6) 5-hydroxy-4-methyl-3-(phosphonooxy)cyclohex-1-ene-1-carboxylate; (7) 5-[(1-carboxyeth-1-en-1-yl)oxy]-4-methyl-3-(phosphonooxy)cyclohex-1-ene-1-carboxylate; (8) 3-[(1-carboxyeth-1-en-1-yl)oxy]-4-methylcyclohexa-1,5-diene-1-carboxylate; and (9) p-toluate.
Figure 5:
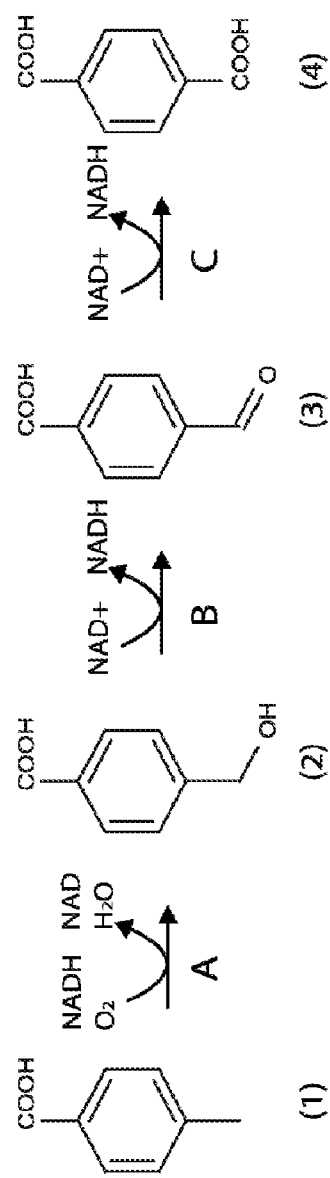
FIG. 5 shows a schematic depiction of an exemplary pathway for conversion of p-toluate to terephthalic acid (PTA). Reactions A, B and C are catalyzed by p-toluate methyl-monooxygenase reductase, 4-carboxybenzyl alcohol dehydrogenase and 4-carboxybenzyl aldehyde dehydrogenase, respectively. The compounds shown are (1) p-toluic acid; (2) 4-carboxybenzyl alcohol; (3) 4-carboxybenzaldehyde and (4) terephthalic acid.

The maximum theoretical PTA yield from glucose via the proposed erythrose-4-phosphate pathway in FIG. 1, in conjunction with the pathways from 2H3M4OP to PTA in FIGS. 4 and 5, is 0.6 moles of PTA per mole of glucose utilized (0.55 g/g). Increasing product yields to 0.61 mol/mol (0.56 g/g) is possible if cells are capable of fixing $CO_2$ through pathways such as the reductive TCA cycle or the Wood-Ljungdahl pathway.

Figure 2:
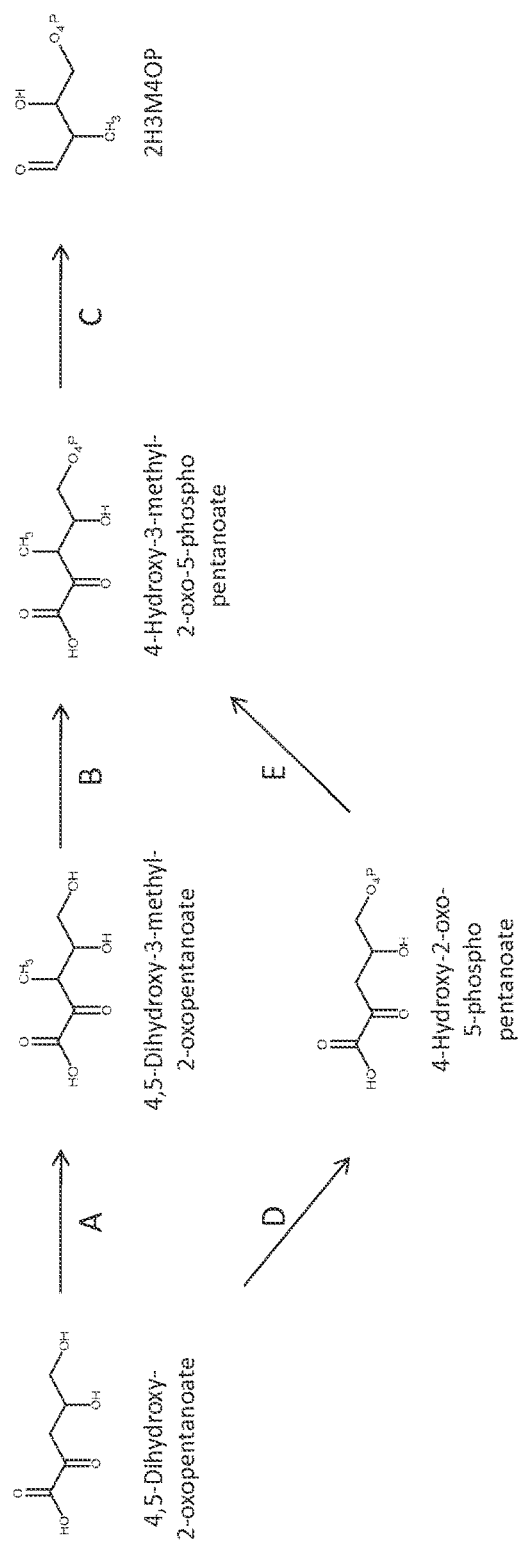
FIG. 2 shows a schematic depiction of exemplary pathways to 2H3M4OP from 4,5-dihydroxy-2-oxopentanoate. In steps A-E, the enzymes can be: A. 4,5-dihydroxy-2-oxopentanoate methyltransferase; B. 4,5-dihydroxy-3-methyl-2-oxopentanoate kinase; C. 4-hydroxy-3-methyl-2-oxo-5-phosphopentanoate decarboxylase; D. 4,5-dihydroxy-2-oxopentanoate kinase; and E. 4-hydroxy-2-oxo-5-phosphopentanoate methyltransferase. 2H3M4OP is (2-hydroxy-3-methyl-4-oxobutoxy)phosphonate.

The maximum theoretical PTA yield from xylose via the 4,5-dihydroxy-2-oxopentanoate pathway of FIG. 2 is 0.46 moles PTA per mole xylose utilized (0.51 g/g).

The conversion of G3P to p-toluate requires one ATP, two reducing equivalents (NAD(P)H), and two molecules of phosphoenolpyruvate, according to net reaction below.

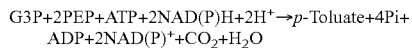
G3P+2PEP+ATP+2NAD(P)H+2H$^+$→p-Toluate+4Pi+ADP+2NAD(P)$^+$+CO$_2$+H$_2$O One equivalent of $CO_2$ is generated in this net reaction.

An additional ATP is required to synthesize G3P from glucose. The maximum theoretical p-toluate yield is 0.67 mol/mol (0.51 g/g) from glucose minus carbon required for energy. Under the assumption that 2 ATPs are consumed per p-toluate molecule synthesized, the predicted p-toluate yield from glucose is 0.62 mol/mol (0.46 g/g) p-toluate.

If p-toluate is further converted to PTA by enzymes as described in Example IV, the predicted PTA yield from glucose is 0.64 mol/mol (0.58 g/g). In this case, the oxidation of p-toluate to PTA generates an additional net reducing equivalent according to the net reaction:

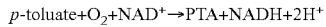
p-toluate+O$_2$+NAD$^+$→PTA+NADH+2H$^+$

Enzyme candidates for catalyzing each step of the proposed pathways are described in the following sections.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a muconate, 2H3M4OP, p-toluate and/or terephthalate biosynthetic pathway.

A metabolic modification refers to a biochemical reaction that is altered from its naturally occurring state. Therefore, non-naturally occurring microorganisms can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "(2-hydroxy-3-methyl-4-oxobutoxy)phosphonate," abbreviated herein as 2H3M4OP, has the chemical formula as shown in FIG. 1. Such a compound can also be described as 3-hydroxy-2-methyl butanal-4-phosphate.

As used herein, the term "p-toluate," having the molecular formula $C_8H_7O_2^-$ (see FIG. 4, compound 9) (IUPAC name 4-methylbenzoate) is the ionized form of p-toluic acid, and it is understood that p-toluate and p-toluic acid can be used interchangeably throughout to refer to the compound in any of its neutral or ionized forms, including any salt forms thereof. It is understood by those skilled understand that the specific form will depend on the pH.

As used herein, the term "terephthalate," having the molecular formula $C_8H_4O_4^{-2}$ (see FIG. 5, compound 4)(IUPAC name terephthalate) is the ionized form or dianionic form of terephthalic acid, also referred to as p-phthalic acid or PTA, depicted below.

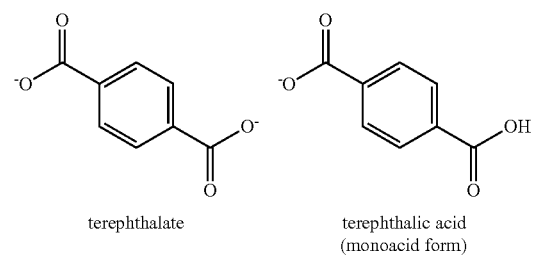

terephthalate     terephthalic acid (monoacid form)

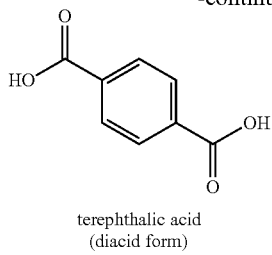

terephthalic acid
(diacid form)

Those skilled in the art will understand that occurrences of terephthalate and terephthalic acid in solution will depend on pH, moreover the terms "terephthalate" and "terephthalic acid," unless otherwise indicated in the context that they are used, can be used interchangeably throughout to refer to the compound in any of its neutral or ionized forms, including any salt forms thereof and are not intended to be limiting to one specific form, e.g., its neutral or acid form, or ionized forms, including any salt forms thereof. As terephthalic acid is a dicarboxylic acid, it can exist in a partially protonated monoacid form or a fully protonated diacid form, dependent on the pH. Unless otherwise specified, as used herein "terephthalic acid" will refer to the fully protonated diacid form.

As used herein, the term "bio-based" means derived from or synthesized by a biological organism and can be considered a renewable resource since it can be generated by a biological organism. Such a biological organism, in particular the microbial organisms of the invention disclosed herein, can utilize feedstock or biomass, such as sugars, glycerol or carbohydrates obtained from an agricultural, plant, bacterial, or animal source. Alternatively, the biological organism can utilize atmospheric carbon, carbon dioxide, formate, methane, methanol, carbon in the form of syngas or a carbon source generated from electrochemical conversion of carbon dioxide.

As used herein, the term "bio-derived" means a product as described herein that is composed, in whole or in part, of a bio-based compound of the invention. A bio-derived or bio-based product is in contrast to a petroleum derived product, wherein such a product is derived from or synthesized from petroleum or a petrochemical feedstock.

As used herein, the term "muconate" is an ionized or anionic form of muconic acid depicted below.

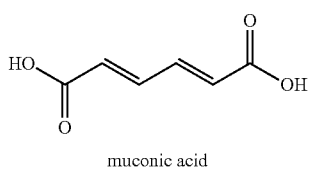

muconic acid

Those skilled in the art will understand that occurrences of muconate and muconic acid in solution will depend on pH, moreover the terms "muconate" and "muconic acid," unless otherwise indicated in the context that they are used, are not intended to be limiting to one specific form, e.g., its neutral or acid form, or ionized forms, including any salt forms thereof.

As used herein, the term "aromatic carboxylic acid" refers to a compound that contains one or more carboxylate (COOH) groups, bonded to an aromatic ring. Examples of aromatic carboxylic acids include benzoic acid, salicylic acid, gallic acid, o-toluic acid, m-toluic acid, p-toluic acid, phthalic acid, isophthalic acid, and terephthalic acid, as depicted below.

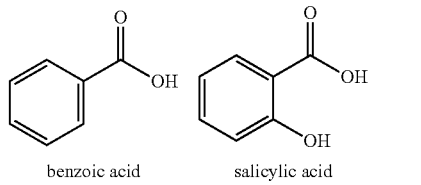

benzoic acid           salicylic acid

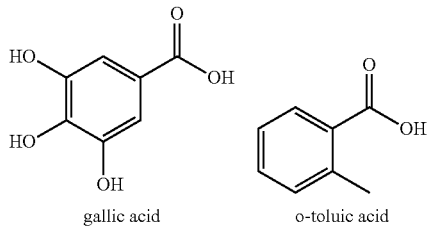

gallic acid            o-toluic acid

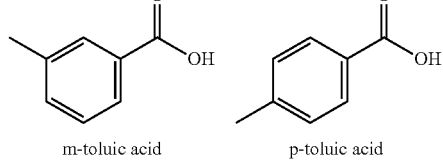

m-toluic acid          p-toluic acid

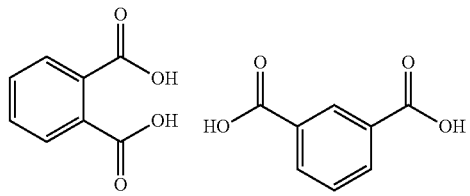

phthalic acid          isophthalic acid

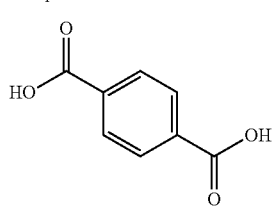

terephthalic acid

Those skilled in the art will understand that certain aromatic carboxylic acids are mono carboxylic acids (monoacids), such as p-toluic acid, whereas certain aromatic carboxylic acids are di carboxylic acids (diacids), such as terephthalic acid.

As used herein, the term "aromatic carboxylate anion" refers to the conjugate base of the aromatic carboxylic acid. Those skilled in the art will understand that when a carboxyl group is deprotonated, the carboxylate anion is formed. Those skilled in the art will further understand that the specific form of the aromatic carboxylic acid (i.e., whether protonated as an acid, or deprotonated as an anion) will depend on the pH.

As used herein, the term "p-toluate" is the ionized or anionic form of p-toluic acid, as depicted below.

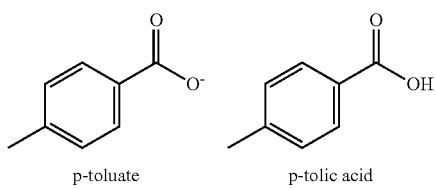

p-toluate          p-tolic acid

Those skilled in the art will understand that occurrences of p-toluate and p-toluic acid in solution will depend on pH, moreover the terms "p-toluate" and "p-toluic acid," unless otherwise indicated in the context that they are used, are not intended to be limiting to one specific form, e.g., its neutral or acid form, or ionized forms, including any salt forms thereof.

As used herein, the terms "about" or "approximately" means an acceptable error for a particular value as determined by those of skill in the art, which depends in part on how the value is measured or determined. In certain embodiments, the terms "about" or "approximately" means within 1, 2, 3, or 4 standard deviations. In certain embodiments, the term "about" or "approximately" means within above or below 20%, 15%, 10%, 9%, 8%, 7%, 6%, 5%, 4%, 3%, 2%, 1%, 0.5%, or 0.05% of a given value or range.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having 2H3M4OP, p-toluate or terephthalate biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In one embodiment, the invention provides a non-naturally occurring microbial organism having a 2H3M4OP pathway and including at least one exogenous nucleic acid encoding a 2H3M4OP pathway enzyme expressed in a sufficient amount to produce 2H3M4OP. The 2H3M4OP pathway of the microbial organism can include a pathway selected from: (1) 1A, 1B, 1C, 1D, 1E and 1F; (2) 2A, 2B and 2C; and (3) 2D, 2E and 2C, wherein 1A is an erythrose-4-phosphate dehydrogenase, wherein 1B is a 4-phosphoerythronate dehydrogenase, wherein 1C is a 2-acetyl-2,3-dihydroxy-4-phosphobutanoate synthase, wherein 1D is a 2-acetyl-2,3-dihydroxy-4-phosphobutanoate reductoisomerase, wherein 1E is a 2,3,4-trihydroxy-3-methyl-5-phosphopentanoate dehydratase, wherein 1F is a 4-hydroxy-3-methyl-2-oxo-5-phosphopentanoate decarboxylase, wherein 2A is a 4,5-dihydroxy-2-oxopentanoate methyltransferase, wherein 2B is a 4,5-dihydroxy-3-methyl-2-oxopentanoate kinase, wherein 2C is a 4-hydroxy-3-methyl-2-oxo-5-phosphopentanoate decarboxylase, wherein 2D is a 4,5-dihydroxy-2-oxopentanoate kinase, wherein 2E is a 4-hydroxy-2-oxo-5-phosphopentanoate methyltransferase (see FIGS. 1 and 2 and Example I). Additionally, in some aspects, the microbial organism of the invention can include two, three, four, five or six exogenous nucleic acids, wherein each exogenous nucleic acid encodes a 2H3M4OP pathway enzyme as described herein. In some aspects, the invention provides a microbial organism of the invention having exogenous nucleic acids encoding each of the 2H3M4OP pathway enzymes of at least one of the 2H3M4OP pathways selected from (1)-(3), as described above.

Figure 3:
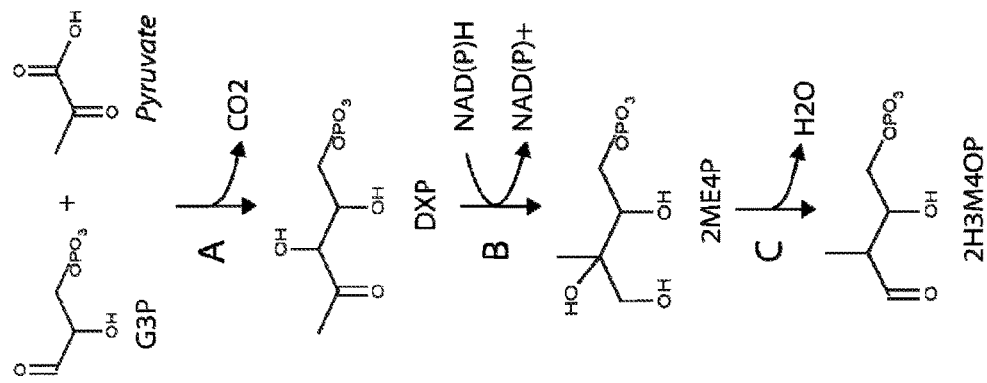
FIG. 3 shows a schematic depiction of an exemplary pathway to 2H3M4OP from glyceraldehyde-3-phosphate and pyruvate. G3P is glyceraldehyde-3-phosphate, DXP is 1-deoxy-D-xylulose-5-phosphate, 2ME4P is C-methyl-D-erythritol-4-phosphate and 2H3M4OP is (2-hydroxy-3-methyl-4-oxobutoxy)phosphonate. In steps A-C, the enzymes can be: A. DXP synthase; B. DXP reductoisomerase; and C. 2ME4P dehydratase.

In some aspects, the invention provides the 2H3M4OP pathway of the microbial organisms includes a 2-C-methyl-D-erythritol-4-phosphate dehydratase (see Example II and FIG. 3, step C). A non-naturally occurring microbial organism having a 2H3M4OP pathway can further have a 1-deoxyxylulose-5-phosphate synthase or a 1-deoxy-D-xylulose-5-phosphate reductoisomerase (see Example II and FIG. 3, steps A and B). Thus, a 2H3M4OP pathway can include a 2-C-methyl-D-erythritol-4-phosphate dehydratase, a 1-deoxyxylulose-5-phosphate synthase and a 1-deoxy-D-xylulose-5-phosphate reductoisomerase.

The invention also provides a non-naturally occurring microbial organism having a 2H3M4OP pathway as described herein and/or a p-toluate pathway. In this aspect, the p-toluate pathway can include at least one exogenous nucleic acid encoding a p-toluate pathway enzyme expressed in a sufficient amount to produce p-toluate. In some aspects, the p-toluate pathway includes 4A, 4B, 4C, 4D, 4E, 4F, 4G and/or 4H, wherein 4A is a 2-dehydro-3-deoxyphosphoheptonate synthase; wherein 4B is a 3-dehydroquinate synthase; wherein 4C is a 3-dehydroquinate dehydratase; wherein 4D is a shikimate dehydrogenase; wherein 4E is a shikimate kinase; wherein 4F is a 3-phosphoshikimate-2-carboxyvinyltransferase; wherein 4G is a chorismate synthase and wherein 4H is a chorismate lyase (see Example III and FIG. 4, steps A-H). A non-naturally occurring microbial organism having a p-toluate pathway can further include a 2H3M4OP pathway as described herein (see Examples I and II and FIGS. 1-3). For example, a 2H3M4OP pathway can include a pathway selected from: (1) 1A, 1B, 1C, 1D, 1E and 1F; (2) 2A, 2B and 2C; and (3) 2D, 2E and 2C, wherein 1A is an erythrose-4-phosphate dehydrogenase, wherein 1B is a 4-phosphoerythronate dehydrogenase, wherein 1C is a 2-acetyl-2,3-dihydroxy-4-phosphobutanoate synthase, wherein 1D is a 2-acetyl-2,3-dihydroxy-4-phosphobutanoate reductoisomerase, wherein 1E is a 2,3,4-trihydroxy-3-methyl-5-phosphopentanoate dehydratase, wherein 1F is a 4-hydroxy-3-methyl-2-oxo-5-phosphopentanoate decarboxylase, wherein 2A is a 4,5-dihydroxy-2-oxopentanoate methyltransferase, wherein 2B is a 4,5-dihydroxy-3-methyl-2-oxopentanoate kinase, wherein 2C is a 4-hydroxy-3-methyl-2-oxo-5-phosphopentanoate decarboxylase, wherein 2D is a 4,5-dihydroxy-2-oxopentanoate kinase, wherein 2E is a 4-hydroxy-2-oxo-5-phosphopentanoate methyltransferase (see FIGS. 1 and 2 and Example I). Alternatively, a 2H3M4OP pathway can include a 2-C-methyl-D-erythritol-4-phosphate dehydratase, a 1-deoxyxylulose-5-phosphate synthase and/or a 1-deoxy-D-xylulose-5-phosphate reductoisomerase (see FIG. 3 and Example II).

In some aspects, the microbial organism of the invention includes two, three, four, five, six, seven or eight exogenous nucleic acids, wherein each nucleic acid encodes a p-toluate pathway enzyme. Additionally, in some aspects, the invention provides that the microbial organism of the invention includes exogenous nucleic acids encoding each of the enzymes of the p-toluate pathway disclosed herein.

The invention additionally provides a non-naturally occurring microbial organism having a 2H3M4OP pathway and/or a p-toluate pathway as disclosed herein and/or a terephthalate pathway. In this aspect, the terephthalate pathway can include at least one exogenous nucleic acid encoding a terephthalate pathway enzyme expressed in a sufficient amount to produce terephthalate. In some aspects of the invention, the terephthalate pathway can include 5A, 5B and 5C, wherein 5A is a p-toluate methyl-monooxygenase reductase, wherein 5B is a 4-carboxybenzyl alcohol dehydrogenase and wherein 5C is a 4-carboxybenzyl aldehyde dehydrogenase (see Example IV and FIG. 5). Such an organism containing a terephthalate pathway can additionally include a p-toluate pathway, wherein the p-toluate pathway includes 4A, 4B, 4C, 4D, 4E, 4F, 4G and/or 4H, wherein 4A is a 2-dehydro-3-deoxyphosphoheptonate synthase; wherein 4B is a 3-dehydroquinate synthase; wherein 4C is a 3-dehydroquinate dehydratase; wherein 4D is a shikimate dehydrogenase; wherein 4E is a shikimate kinase; wherein 4F is a 3-phosphoshikimate-2-carboxyvinyltransferase; wherein 4G is a chorismate synthase and wherein 4H is a chorismate lyase (see Examples III and IV and FIGS. 4 and 5). Such a non-naturally occurring microbial organism having a terephthalate pathway and a p-toluate pathway can further include a 2H3M4OP pathway as described herein (see Examples I and II and FIGS. 1-3). For example, a 2H3M4OP pathway can include a pathway selected from: (1) 1A, 1B, 1C, 1D, 1E and 1F; (2) 2A, 2B and 2C; and (3) 2D, 2E and 2C, wherein 1A is an erythrose-4-phosphate dehydrogenase, wherein 1B is a 4-phosphoerythronate dehydrogenase, wherein 1C is a 2-acetyl-2,3-dihydroxy-4-phosphobutanoate synthase, wherein 1D is a 2-acetyl-2,3-dihydroxy-4-phosphobutanoate reductoisomerase, wherein 1E is a 2,3,4-trihydroxy-3-methyl-5-phosphopentanoate dehydratase, wherein 1F is a 4-hydroxy-3-methyl-2-oxo-5-phosphopentanoate decarboxylase, wherein 2A is a 4,5-dihydroxy-2-oxopentanoate methyltransferase, wherein 2B is a 4,5-dihydroxy-3-methyl-2-oxopentanoate kinase, wherein 2C is a 4-hydroxy-3-methyl-2-oxo-5-phosphopentanoate decarboxylase, wherein 2D is a 4,5-dihydroxy-2-oxopentanoate kinase, wherein 2E is a 4-hydroxy-2-oxo-5-phosphopentanoate methyltransferase (see FIGS. 1 and 2 and Example I). Alternatively, a 2H3M4OP pathway can include a 2-C-methyl-D-erythritol-4-phosphate dehydratase, a 1-deoxyxylulose-5-phosphate synthase and/or a 1-deoxy-D-xylulose-5-phosphate reductoisomerase (see FIG. 3 and Example II).

In some aspects, the microbial organism of the invention includes two or three exogenous nucleic acids, wherein each nucleic acid encodes a terephthalate pathway enzyme. Additionally, in some aspects, the invention provides that the microbial organism of the invention includes exogenous nucleic acids encoding each of the enzymes of the terephthalate pathway disclosed herein.

In an additional embodiment, the invention provides a non-naturally occurring microbial organism having a 2H3M4OP, p-toluate and/or terephthalate pathway, wherein the non-naturally occurring microbial organism comprises at least one exogenous nucleic acid encoding an enzyme or protein that converts a substrate to a product. For example, in a 2H3M4OP pathway, the substrates and products can be selected from the group consisting of erythrose-4-phosphate to 4-phosphoerythronate; 4-phosphoerythronate to 2-oxo-3-hydroxy-4-phosphobutanoate; 2-oxo-3-hydroxy-4-phosphobutanoate to 2-acetyl-2,3-dihydroxy-4-phosphobutanoate; 2-acetyl-2,3-dihydroxy-4-phosphobutanoate to 2,3,4-trihydroxy-3-methyl-5-phosphopentanoate; 2,3,4-trihydroxy-3-methyl-5-phosphopentanoate to 4-hydroxy-3-methyl-2-oxo-5-phosphopentanoate; 4-hydroxy-3-methyl-2-oxo-5-phosphopentanoate to (2-hydroxy-3-methyl-4-oxobutoxy)phosphonate; 4,5-dihydroxy-2-oxopentanoate to 4,5-dihydroxy-3-methyl-2-oxopentanoate; 4,5-dihydroxy-2-oxopentanoate to 4-hydroxy-2-oxo-5-phosphopentanoate; 4-hydroxy-2-oxo-5-phosphopentanoate to 4-hydroxy-3-methyl-2-oxo-5-phosphopentanoate; 4,5-dihydroxy-3-methyl-2-oxopentanoate to 4-hydroxy-3-methyl-2-oxo-5-phosphopentanoate; glyceraldehyde-3-phosphate and pyruvate to 1-deoxy-D-xylulose-5-phosphate; 1-deoxy-D-xylulose-5-phosphate to C-methyl-D-erythritol-4-phosphate; and C-methyl-D-erythritol-4-phosphate to (2-hydroxy-3-methyl-4-oxobutoxy)phosphonate (see Examples I and II and FIGS. 1-3). In another embodiment, a p-toluate pathway can comprise substrates and products selected from (2-hydroxy-3-methyl-4-oxobutoxy)phosphonate to 2,4-dihydroxy-5-methyl-6-[(phosphonooxy)methyl]oxane-2-carboxylate; 2,4-dihydroxy-5-methyl-6-[(phosphonooxy)methyl]oxane-2-carboxylate to 1,3-dihydroxy-4-methyl-5-oxocyclohexane-1-carboxylate; 1,3-dihydroxy-4-methyl-5-oxocyclohexane-1-carboxylate to 5-hydroxy-4-methyl-3-oxocyclohex-1-ene-1-carboxylic acid; 5-hydroxy-4-methyl-3-oxocyclohex-1-ene-1-carboxylic acid to 3,5-dihydroxy-4-methylcyclohex-1-ene-1-carboxylate; 3,5-dihydroxy-4-methylcyclohex-1-ene-1-carboxylate to 5-hydroxy-4-methyl-3-(phosphonooxy)cyclohex-1-ene-1-carboxylate; 5-hydroxy-4-methyl-3-(phosphonooxy)cyclohex-1-ene-1-carboxylate to 5-[(1-carboxyeth-1-en-1-yl)oxy]-4-methyl-3-(phosphonooxy)cyclohex-1-ene-1-carboxylate; 5-[(1-carboxyeth-1-en-1-yl)oxy]-4-methyl-3-(phosphonooxy)cyclohex-1-ene-1-carboxylate to 3-[(1-carboxyeth-1-en-1-yl)oxy]-4-methylcyclohexa-1,5-diene-1-carboxylate; and 3-[(1-carboxyeth-1-en-1-yl)oxy]-4-methylcyclohexa-1,5-diene-1-carboxylate to p-toluate (see Example II and FIG. 2). In still another embodiment, a terephthalate pathway can comprise substrates and products selected from p-toluate to 4-carboxybenzyl alcohol; 4-carboxybenzyl alcohol to 4-carboxybenzaldehyde; and 4-carboxybenzaldehyde to and terephthalic acid (see Example III and FIG. 3). One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a 2H3M4OP, p-toluate or terephthalate pathway, such as that shown in FIGS. 1-5.

While generally described herein as a microbial organism that contains a 2H3M4OP, p-toluate or terephthalate pathway, it is understood that the invention additionally provides a non-naturally occurring microbial organism comprising at least one exogenous nucleic acid encoding a 2H3M4OP, p-toluate or terephthalate pathway enzyme expressed in a sufficient amount to produce an intermediate of a 2H3M4OP, p-toluate or terephthalate pathway. For example, as disclosed herein, a 2H3M4OP, p-toluate or terephthalate pathway is exemplified in FIGS. 1-5. Therefore, in addition to a microbial organism containing a 2H3M4OP, p-toluate or terephthalate pathway that produces 2H3M4OP, p-toluate or terephthalate, the invention additionally provides a non-naturally occurring microbial organism comprising at least one exogenous nucleic acid encoding a 2H3M4OP, p-toluate or terephthalate pathway enzyme, where the microbial organism produces a 2H3M4OP, p-toluate or terephthalate pathway intermediate, for example, 4-phosphoerythronate, 2-oxo-3-hydroxy-4-phosphobutanoate, 2-acetyl-2,3-phosphodutanoate, 2-acetyl-2,3-dihydroxy-4-phosphobutanoate, 2,3,4-trihydroxy-3-methyl-5-phosphopentanoate, 4-hydroxy-3-methyl-2-oxo-5-phosphopentanoate, 4,5-dihydroxy-3-methyl-2-oxopentanoate, 4-hydroxy-2-oxo-5-phosphopentanoate, 1-deoxy-D-xylulose-5-phosphate, C-methyl-D-erythritol-4-phosphate, 2,4-dihydroxy-5-methyl-6-[(phosphonooxy)methyl]oxane-2-carboxylate, 1,3-dihydroxy-4-methyl-5-oxocyclohexane-1-carboxylate, 5-hydroxy-4-methyl-3-oxocyclohex-1-ene-1-carboxylate, 3,5-dihydroxy-4-methylcyclohex-1-ene-1-carboxylate, 5-hydroxy-4-methyl-3-(phosphonooxy)cyclohex-1-ene-1-carboxylate, 5-[(1-carboxyeth-1-en-1-yl)oxy]-4-methyl-3-(phosphonooxy)cyclohex-1-ene-1-carboxylate, 3-[(1-carboxyeth-1-en-1-yl)oxy]-4-methylcyclohexa-1,5-diene-1-carboxylate, 4-carboxybenzyl alcohol or 4-carboxybenzaldehyde.

It is understood that any of the pathways disclosed herein, as described in the Examples and exemplified in the Figures, including the pathways of FIGS. 1-5, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a 2H3M4OP, p-toluate or terephthalate pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, the product p-toluate or terephthalate or the intermediate 4-phosphoerythronate, 2-oxo-3-hydroxy-4-phosphobutanoate, 2-acetyl-2,3-phosphodutanoate, 2-acetyl-2,3-dihydroxy-4-phosphobutanoate, 2,3,4-trihydroxy-3-methyl-5-phosphopentanoate, 4-hydroxy-3-methyl-2-oxo-5-phosphopentanoate, 4,5-dihydroxy-3-methyl-2-oxopentanoate, 4-hydroxy-2-oxo-5-phosphopentanoate, 2,4-dihydroxy-5-methyl-6-[(phosphonooxy)methyl]oxane-2-carboxylate, 1,3- dihydroxy-4-methyl-5-oxocyclohexane-1-carboxylate, 5-hydroxy-4-methyl-3-oxocyclohex-1-ene-1-carboxylate, 3,5-dihydroxy-4-methylcyclohex-1-ene-1-carboxylate, 5-hydroxy-4-methyl-3-(phosphonooxy)cyclohex-1-ene-1-carboxylate, 5-[(1-carboxyeth-1-en-1-yl)oxy]-4-methyl-3-(phosphonooxy)cyclohex-1-ene-1-carboxylate, 3-[(1-carboxyeth-1-en-1-yl)oxy]-4-methylcyclohexa-1,5-diene-1-carboxylate, 4-carboxybenzyl alcohol or 4-carboxybenzaldehyde, as well as other intermediates, are carboxylic acids, which can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl terephthalate, ethyl terephthalate, and n-propyl terephthalate. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitoyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The non-naturally occurring microbial organisms of the invention can be produced by introducing expressible nucleic acids encoding one or more of the enzymes or proteins participating in one or more 2H3M4OP, p-toluate or terephthalate biosynthetic pathways. Depending on the host microbial organism chosen for biosynthesis, nucleic acids for some or all of a particular 2H3M4OP, p-toluate or terephthalate biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve 2H3M4OP, p-toluate or terephthalate biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as 2H3M4OP, p-toluate or terephthalate.

Host microbial organisms can be selected from, and the non-naturally occurring microbial organisms generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*.

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Candida albicans, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. Preferred host microbial organisms can be selected from, and the non-naturally occurring microbial organisms generated in, for example, bacteria, yeast, fungus or any of a variety of other microorganisms applicable to fermentation processes, as disclosed in U.S. Patent Publication No. US 2011/0207185 A1. *E. coli* is a particularly useful and preferred host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the 2H3M4OP, p-toluate or terephthalate biosynthetic pathway constituents of a selected host microbial organism, the non-naturally occurring microbial organisms of the invention will include at least one exogenously expressed 2H3M4OP, p-toluate or terephthalate pathway-encoding nucleic acid and up to all encoding nucleic acids for one or more 2H3M4OP, p-toluate or terephthalate biosynthetic pathways. For example, 2H3M4OP, p-toluate or terephthalate biosynthesis can be established in a host deficient in a pathway enzyme or protein through exogenous expression of the corresponding encoding nucleic acid. In a host deficient in all enzymes or proteins of a 2H3M4OP, p-toluate or terephthalate pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of 2H3M4OP, p-toluate or terephthalate can be included. A non-limiting example of all enzymes in a p-toluate pathway includes a 2-dehydro-3-deoxyphosphoheptonate synthase; a 3-dehydroquinate synthase; a 3-dehydroquinate dehydratase; a shikimate dehydrogenase; shikimate kinase; a 3-phosphoshikimate-2-carboxyvinyltransferase; a chorismate synthase; and a chorismate lyase. In addition, a non-limiting example of all enzymes in a terephthalate pathway included a p-toluate methyl-monooxygenase reductase; a 4-carboxybenzyl alcohol dehydrogenase; and a 4-carboxybenzyl aldehyde dehydrogenase. Furthermore, a non-limiting example of all enzymes in a 2H3M4OP pathway include an erythrose-4-phosphate dehydrogenase, a 4-phosphoerythronate dehydrogenase, a 2-acetyl-2,3-dihydroxy-4-phosphobutanoate synthase, a 2-acetyl-2,3-dihydroxy-4-phosphobutanoate reductoisomerase, a 2,3,4-trihydroxy-3-methyl-5-phosphopentanoate dehydratase and a 4-hydroxy-3-methyl-2-oxo-5-phosphopentanoate decarboxylase.

Given the teachings and guidance provided herein, those skilled in the art will understand that the number of encoding nucleic acids to introduce in an expressible form will, at least, parallel the 2H3M4OP, p-toluate or terephthalate pathway deficiencies of the selected host microbial organism. Therefore, a non-naturally occurring microbial organism of the invention can have one, two, three, four, five, six, seven, eight, nine, ten, eleven, twelve, thirteen, fourteen, fifteen, sixteen or seventeen, up to all nucleic acids encoding the enzymes or proteins constituting a 2H3M4OP, p-toluate or terephthalate biosynthetic pathway disclosed herein. In some embodiments, the non-naturally occurring microbial organisms also can include other genetic modifications that facilitate or optimize 2H3M4OP, p-toluate or terephthalate biosynthesis or that confer other useful functions onto the host microbial organism. One such other functionality can include, for example, augmentation of the synthesis of one or more of the 2H3M4OP, p-toluate or terephthalate pathway precursors such as erythrose-4-phosphate, 4,5-dihydroxy-2-oxopentanoate, glyceraldehyde-3-phosphate and pyruvate.

Generally, a host microbial organism is selected such that it produces the precursor of a 2H3M4OP, p-toluate or terephthalate pathway, either as a naturally produced molecule or as an engineered product that either provides de novo production of a desired precursor or increased production of a precursor naturally produced by the host microbial organism. For example, erythrose-4-phosphate, 4,5-dihydroxy-2-oxopentanoate, glyceraldehyde-3-phosphate and pyruvate are produced naturally in a host organism such as E. coli. A host organism can be engineered to increase production of a precursor, as disclosed herein. In addition, a microbial organism that has been engineered to produce a desired precursor can be used as a host organism and further engineered to express enzymes or proteins of a 2H3M4OP, p-toluate or terephthalate pathway.

In some embodiments, a non-naturally occurring microbial organism of the invention is generated from a host that contains the enzymatic capability to synthesize 2H3M4OP, p-toluate or terephthalate. In this specific embodiment it can be useful to increase the synthesis or accumulation of a 2H3M4OP, p-toluate or terephthalate pathway product to, for example, drive 2H3M4OP, p-toluate or terephthalate pathway reactions toward 2H3M4OP, p-toluate or terephthalate production. Increased synthesis or accumulation can be accomplished by, for example, overexpression of nucleic acids encoding one or more of the above-described 2H3M4OP, p-toluate or terephthalate pathway enzymes or proteins. Overexpression of the enzyme or enzymes and/or protein or proteins of the 2H3M4OP, p-toluate or terephthalate pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing 2H3M4OP, p-toluate or terephthalate, through overexpression of one, two, three, four, five one, two, three, four, five, six, seven, eight, nine, ten, eleven, twelve, thirteen, fourteen, fifteen, sixteen or seventeen, that is, up to all nucleic acids encoding 2H3M4OP, p-toluate or terephthalate biosynthetic pathway enzymes or proteins. In addition, a non-naturally occurring organism can be generated by mutagenesis of an endogenous gene that results in an increase in activity of an enzyme in the 2H3M4OP, p-toluate or terephthalate biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, a 2H3M4OP, p-toluate or terephthalate biosynthetic pathway onto the microbial organism. Alternatively, encoding nucleic acids can be introduced to produce an intermediate microbial organism having the biosynthetic capability to catalyze some of the required reactions to confer 2H3M4OP, p-toluate or terephthalate biosynthetic capability. For example, a non-naturally occurring microbial organism having a 2H3M4OP, p-toluate or terephthalate biosynthetic pathway can comprise at least two exogenous nucleic acids encoding desired enzymes or proteins, such as the combination of a erythrose-4-phosphate dehydrogenase and a 4-phosphoerythronate dehydrogenase, or alternatively a 2-acetyl-2,3-dihydroxy-4-phosphobutanoate reductoisomerase and a 4-hydroxy-3-methyl-2-oxo-5-phosphopentanoate decarboxylase, or alternatively a 4,5-dihydroxy-3-methyl-2-oxopentanoate kinase and a 4-hydroxy-3-methyl-2-oxo-5-phosphopentanoate decarboxylase, or alternatively a 2-dehydro-3-deoxyphosphoheptonate synthase and a shikimate kinase, or alternatively a 4-carboxybenzyl alcohol dehydrogenase and a 4-carboxybenzyl aldehyde dehydrogenase, and the like. Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention, for example, a 2-acetyl-2,3-dihydroxy-4-phosphobutanoate synthase, a 2-acetyl-2,3-dihydroxy-4-phosphobutanoate reductoisomerase and a 2,3,4-trihydroxy-3-methyl-5-phosphopentanoate dehydratase, or alternatively a 4-hydroxy-3-methyl-2-oxo-5-phosphopentanoate decarboxylase, a 4,5-dihydroxy-2-oxopentanoate kinase and a 4-hydroxy-2-oxo-5-phosphopentanoate methyltransferase, or alternatively a shikimate dehydrogenase, a shikimate kinase and a 3-phosphoshikimate-2-carboxyvinyltransferase, and so forth, as desired, so long as the combination of enzymes and/or proteins of the desired biosynthetic pathway results in production of the corresponding desired product. Similarly, any combination of four, five, six, seven, eight, nine, ten, eleven, twelve, thirteen, fourteen, fifteen, sixteen or seventeen or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product.

In addition to the biosynthesis of 2H3M4OP, p-toluate or terephthalate as described herein, the non-naturally occurring microbial organisms and methods of the invention also can be utilized in various combinations with each other and with other microbial organisms and methods well known in the art to achieve product biosynthesis by other routes. For example, one alternative to produce 2H3M4OP, p-toluate or terephthalate other than use of the 2H3M4OP, p-toluate or terephthalate producers is through addition of another microbial organism capable of converting a 2H3M4OP, p-toluate or terephthalate pathway intermediate to 2H3M4OP, p-toluate or terephthalate. One such procedure includes, for example, the fermentation of a microbial organism that produces a 2H3M4OP, p-toluate or terephthalate pathway intermediate. The 2H3M4OP, p-toluate or terephthalate pathway intermediate can then be used as a substrate for a second microbial organism that converts the 2H3M4OP, p-toluate or terephthalate pathway intermediate to 2H3M4OP, p-toluate or terephthalate. The 2H3M4OP, p-toluate or terephthalate pathway intermediate can be added directly to another culture of the second organism or the original culture of the 2H3M4OP, p-toluate or terephthalate pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, 2H3M4OP, p-toluate or terephthalate. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of 2H3M4OP, p-toluate or terephthalate can be accomplished by constructing a microbial organism that contains biosynthetic pathways for conversion of one pathway intermediate to another pathway intermediate or the product. Alternatively, 2H3M4OP, p-toluate or terephthalate also can be biosynthetically produced from microbial organisms through co-culture or co-fermentation using two organisms in the same vessel, where the first microbial organism produces a 2H3M4OP intermediate, p-toluate intermediate or terephthalate intermediate and the second microbial organism converts the intermediate to 2H3M4OP, p-toluate or terephthalate.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 2H3M4OP, p-toluate or terephthalate.

Sources of encoding nucleic acids for a 2H3M4OP, p-toluate or terephthalate pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Arabidopsis thaliana, Azospirillum brasilense, Bacillus subtilis, Bacteroides fragilis, Bos taurus, Bradyrhizobium japonicum* USDA110, *Burkholderia ambifaria, Burkholderia cenocepacia, Corynebacterium glutamicum, Homo sapiens, Lactococcus lactis, Mesorhizobium loti, Methanococcus aeolicus, Mycobacterium tuberculosis, Neurospora crassa, Pseudomonas aeruginosa, Pseudomonas fluorescens, Pseudomonas putida, Pseudomonas stutzeri, Pseudomonas syringae, Ralstonia eutropha, Rattus norvegicus, Saccharomyces cerevisiae, Salmonella typhimurium, Sinorhizobium melitoti, Streptomyces coelicolor, Streptomyces fradiae, Streptomyces luridus, Streptomyces roseosporus, Streptomyces viridochromogenes, Streptomyces wedmorensis, Sulfolobus solfataricus, Synechococcus* sp. PCC 7002, *Thermoproteus tenax, Vibrio cholera, Xanthomonas oryzae* and *Zymomonas mobilis*, as well as other exemplary species disclosed herein or available as source organisms for corresponding genes. Exemplary species for such sources further include, for example, *Escherichia coli*, as well as other exemplary species disclosed in U.S. Patent Publication No. US 2011/0207185 A1. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 2H3M4OP, p-toluate or terephthalate biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of 2H3M4OP, p-toluate or terephthalate described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 2H3M4OP, p-toluate or terephthalate biosynthetic pathway exists in an unrelated species, 2H3M4OP, p-toluate or terephthalate biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize 2H3M4OP, p-toluate or terephthalate.

Methods for constructing and testing the expression levels of a non-naturally occurring 2H3M4OP, p-toluate or terephthalate producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of 2H3M4OP, p-toluate or terephthalate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more muconate, 2H3M4OP, p-toluate or terephthalate biosynthetic pathway encoding nucleic acids as exemplified herein operably linked to expression control sequences functional in the host organism. An expression vector or vectors can be constructed to include one or more muconate biosynthetic pathway encoding nucleic acids as exemplified herein operably linked to expression control sequences functional in the host organism, as disclosed in U.S. Patent Publication No. US 2011/0207185 A1. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention additionally provides a method for producing 2H3M4OP, by culturing the non-naturally occurring microbial organism containing a 2H3M4OP pathway under conditions and for a sufficient period of time to produce 2H3M4OP. Such a microbial organism can have a 2H3M4OP pathway and include at least one exogenous nucleic acid encoding a 2H3M4OP pathway enzyme expressed in a sufficient amount to produce 2H3M4OP. The 2H3M4OP pathway of the microbial organism can include a pathway selected from: (1) 1A, 1B, 1C, 1D, 1E and 1F; (2) 2A, 2B and 2C; and (3) 2D, 2E and 2C, wherein 1A is an erythrose-4-phosphate dehydrogenase, wherein 1B is a 4-phosphoerythronate dehydrogenase, wherein 1C is a 2-acetyl-2,3-dihydroxy-4-phosphobutanoate synthase, wherein 1D is a 2-acetyl-2,3-dihydroxy-4-phosphobutanoate reductoisomerase, wherein 1E is a 2,3,4-trihydroxy-3-methyl-5-phosphopentanoate dehydratase, wherein 1F is a 4-hydroxy-3-methyl-2-oxo-5-phosphopentanoate decarboxylase, wherein 2A is a 4,5-dihydroxy-2-oxopentanoate methyltransferase, wherein 2B is a 4,5-dihydroxy-3-methyl-2-oxopentanoate kinase, wherein 2C is a 4-hydroxy-3-methyl-2-oxo-5-phosphopentanoate decarboxylase, wherein 2D is a 4,5-dihydroxy-2-oxopentanoate kinase, wherein 2E is a 4-hydroxy-2-oxo-5-phosphopentanoate methyltransferase (see FIGS. 1 and 2 and Example I). Additionally, in some aspects, the microbial organism cultured in the methods of the invention can include two, three, four, five or six exogenous nucleic acids, wherein each exogenous nucleic acid encodes a 2H3M4OP pathway enzyme as described herein. In some aspects, the invention provides a method for producing 2H3M4OP by culturing a microbial organism of the invention having exogenous nucleic acids encoding each of the 2H3M4OP pathway enzymes of at least one of the 2H3M4OP pathways selected from (1)-(3), as described above.

In some aspects, the invention provides the 2H3M4OP pathway of the microbial organism cultured in the invention methods includes a 2-C-methyl-D-erythritol-4-phosphate dehydratase (see Example II and FIG. 3, step C). The non-naturally occurring microbial organism having a 2H3M4OP pathway can further have a 1-deoxyxylulose-5-phosphate synthase or a 1-deoxy-D-xylulose-5-phosphate reductoisomerase (see Example II and FIG. 3, steps A and B). Thus, a 2H3M4OP pathway can include a 2-C-methyl-D-erythritol-4-phosphate dehydratase, a 1-deoxyxylulose-5-phosphate synthase and a 1-deoxy-D-xylulose-5-phosphate reductoisomerase.

The invention also provides a method for producing p-toluate by culturing the non-naturally occurring microbial organism containing a 2H3M4OP pathway and/or a p-toluate pathway under conditions and for a sufficient period of time to produce p-toluate. Such a microbial organism can include at least one exogenous nucleic acid encoding a p-toluate pathway enzyme expressed in a sufficient amount to produce p-toluate. In some aspects, the p-toluate pathway includes 4A, 4B, 4C, 4D, 4E, 4F, 4G and/or 4H, wherein 4A is a 2-dehydro-3-deoxyphosphoheptonate synthase; wherein 4B is a 3-dehydroquinate synthase; wherein 4C is a 3-dehydroquinate dehydratase; wherein 4D is a shikimate dehydrogenase; wherein 4E is a shikimate kinase; wherein 4F is a 3-phosphoshikimate-2-carboxyvinyltransferase; wherein 4G is a chorismate synthase and wherein 4H is a chorismate lyase (see Example III and FIG. 4, steps A-H). A non-naturally occurring microbial organism having a p-toluate pathway can further include a 2H3M4OP pathway as described herein (see Examples I and II and FIGS. 1-3). For example, a 2H3M4OP pathway can include a pathway selected from: (1) 1A, 1B, 1C, 1D, 1E and 1F; (2) 2A, 2B and 2C; and (3) 2D, 2E and 2C, wherein 1A is an erythrose-4-phosphate dehydrogenase, wherein 1B is a 4-phosphoerythronate dehydrogenase, wherein 1C is a 2-acetyl-2,3-dihydroxy-4-phosphobutanoate synthase, wherein 1D is a 2-acetyl-2,3-dihydroxy-4-phosphobutanoate reductoisomerase, wherein 1E is a 2,3,4-trihydroxy-3-methyl-5-phosphopentanoate dehydratase, wherein 1F is a 4-hydroxy-3-methyl-2-oxo-5-phosphopentanoate decarboxylase, wherein 2A is a 4,5-dihydroxy-2-oxopentanoate methyltransferase, wherein 2B is a 4,5-dihydroxy-3-methyl-2-oxopentanoate kinase, wherein 2C is a 4-hydroxy-3-methyl-2-oxo-5-phosphopentanoate decarboxylase, wherein 2D is a 4,5-dihydroxy-2-oxopentanoate kinase, wherein 2E is a 4-hydroxy-2-oxo-5-phosphopentanoate methyltransferase (see FIGS. 1 and 2 and Example I). Alternatively, a 2H3M4OP pathway can include a 2-C-methyl-D-erythritol-4-phosphate dehydratase, a 1-deoxyxylulose-5-phosphate synthase and/or a 1-deoxy-D-xylulose-5-phosphate reductoisomerase (see FIG. 3 and Example II).

In some aspects, the microbial organism cultured in the invention methods include two, three, four, five, six, seven or eight exogenous nucleic acids, wherein each nucleic acid encodes a p-toluate pathway enzyme. Additionally, in some aspects, the invention provides that the microbial organism cultured in the invention methods includes exogenous nucleic acids encoding each of the enzymes of the p-toluate pathway disclosed herein.

The invention also provides a method for producing terephthalate by culturing the non-naturally occurring microbial organism containing a 2H3M4OP pathway, a p-toluate pathway and/or a terephthalate pathway under conditions and for a sufficient period of time to produce terephthalate. Such a microbial organism can include at least one exogenous nucleic acid encoding a terephthalate pathway enzyme expressed in a sufficient amount to produce terephthalate. In some aspects of the invention, the terephthalate pathway can include 5A, 5B and 5C, wherein 5A is a p-toluate methyl-monooxygenase reductase, wherein 5B is a 4-carboxybenzyl alcohol dehydrogenase and wherein 5C is a 4-carboxybenzyl aldehyde dehydrogenase (see Example IV and FIG. 5). Such an organism containing a terephthalate pathway can additionally include a p-toluate pathway, wherein the p-toluate pathway includes 4A, 4B, 4C, 4D, 4E, 4F, 4G and/or 4H, wherein 4A is a 2-dehydro-3-deoxyphosphoheptonate synthase; wherein 4B is a 3-dehydroquinate synthase; wherein 4C is a 3-dehydroquinate dehydratase; wherein 4D is a shikimate dehydrogenase; wherein 4E is a shikimate kinase; wherein 4F is a 3-phosphoshikimate-2-carboxyvinyltransferase; wherein 4G is a chorismate synthase and wherein 4H is a chorismate lyase (see Examples III and IV and FIGS. 4 and 5). Such a non-naturally occurring microbial organism having a terephthalate pathway and a p-toluate pathway can further include a 2H3M4OP pathway as described herein (see Examples I and II and FIGS. 1-3). For example, a 2H3M4OP pathway can include a pathway selected from: (1) 1A, 1B, 1C, 1D, 1E and 1F; (2) 2A, 2B and 2C; and (3) 2D, 2E and 2C, wherein 1A is an erythrose-4-phosphate dehydrogenase, wherein 1B is a 4-phosphoerythronate dehydrogenase, wherein 1C is a 2-acetyl-2,3-dihydroxy-4-phosphobutanoate synthase, wherein 1D is a 2-acetyl-2,3-dihydroxy-4-phosphobutanoate reductoisomerase, wherein 1E is a 2,3,4-trihydroxy-3-methyl-5-phosphopentanoate dehydratase, wherein 1F is a 4-hydroxy-3-methyl-2-oxo-5-phosphopentanoate decarboxylase, wherein 2A is a 4,5-dihydroxy-2-oxopentanoate methyltransferase, wherein 2B is a 4,5-dihydroxy-3-methyl-2-oxopentanoate kinase, wherein 2C is a 4-hydroxy-3-methyl-2-oxo-5-phosphopentanoate decarboxylase, wherein 2D is a 4,5-dihydroxy-2-oxopentanoate kinase, wherein 2E is a 4-hydroxy-2-oxo-5-phosphopentanoate methyltransferase (see FIGS. 1 and 2 and Example I). Alternatively, a 2H3M4OP pathway can include a 2-C-methyl-D-erythritol-4-phosphate dehydratase, a 1-deoxyxylulose-5-phosphate synthase and/or a 1-deoxy-D-xylulose-5-phosphate reductoisomerase (see FIG. 3 and Example II).

In some aspects, the microbial organism cultured in the invention methods includes two or three exogenous nucleic acids, wherein each nucleic acid encodes a terephthalate pathway enzyme. Additionally, in some aspects, the invention provides that the microbial organism cultured in the invention methods includes exogenous nucleic acids encoding each of the enzymes of the terephthalate pathway disclosed herein.

Suitable purification and/or assays to test for the production of 2H3M4OP, p-toluate or terephthalate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. For example, p-toluate methyl-monooxygenase activity can be assayed by incubating purified enzyme with NADH, $FeSO_4$ and the p-toluate substrate in a water bath, stopping the reaction by precipitation of the proteins, and analysis of the products in the supernatant by HPLC (Locher et al., *J. Bacteriol.* 173:3741-3748 (1991)).

The 2H3M4OP, p-toluate or terephthalate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the muconate, 2H3M4OP, p-toluate or terephthalate producers can be cultured for the biosynthetic production of muconate, 2H3M4OP, p-toluate or terephthalate. Accordingly, in some embodiments, the invention provides culture medium having muconate, 2H3M4OP, p-toluate or terephthalate or a muconate, 2H3M4OP, p-toluate or terephthalate pathway intermediate described herein. In some aspects, the culture mediums can also be separated from the non-naturally occurring microbial organisms of the invention that produced the muconate, 2H3M4OP, p-toluate or terephthalate or muconate, 2H3M4OP, p-toluate or terephthalate pathway intermediate. Methods for separating a microbial organism from culture medium are well known in the art. Exemplary methods include filtration, flocculation, precipitation, centrifugation, sedimentation, and the like.

For the production of 2H3M4OP, p-toluate or terephthalate, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719, filed Aug. 10, 2007. Exemplary cell growth procedures and fermentations used in the production of a compound of interest, such as, for example, muconate, 2H3M4OP, p-toluate or terephthalate, include, batch fermentation, fed-batch fermentation with batch separation; fed-batch fermentation with continuous separation, and continuous fermentation with continuous separation. All of these processes are well known in the art. Depending on the non-naturally occurring microbial organism's design, the fermentations can be carried out under aerobic or anaerobic conditions. In certain embodiments, the temperature of the cultures are kept between about 30 and about 45° C., including 31, 32, 33, 34, 35, 36, 37, 38, 39, 40, 41, 42, 43, and 44° C.

In batch fermentation, a tank fermenter (or bioreactor) is filled with the prepared media to support growth. The temperature and pH for microbial fermentation is properly adjusted, and any additional supplements are added. An inoculum of a producing non-naturally occurring microbial organism is added to the fermenter. In batch fermentation the fermentation will generally run for a fixed period and then the products from the fermentation are isolated. The process can be repeated in batch runs.

In fed-batch fermentation fresh media is continuously or periodically added to the fermentation bioreactor. Fixed-volume fed-batch fermentation is a type of fed-batch fermentation in which a carbon source is fed without diluting the culture. The culture volume can also be maintained nearly constant by feeding the growth carbon source as a concentrated liquid or gas. In another type of fixed-volume fed-batch culture, sometimes called a cyclic fed-batch culture, a portion of the culture is periodically withdrawn and used as the starting point for a further fed-batch process. Once the fermentation reaches a certain stage, the culture is removed and the biomass is diluted to the original volume with sterile water or medium containing the carbon feed substrate. The dilution decreases the biomass concentration and results in an increase in the specific growth rate. Subsequently, as feeding continues, the growth rate will decline gradually as biomass increases and approaches the maximum sustainable in the vessel once more, at which point the culture can be diluted again. Alternatively, a fed-batch fermentation can be variable volume. In variable-volume mode the volume of the fermentation broth changes with the fermentation time as nutrient and media are continually added to the culture without removal of a portion of the fermentation broth.

In a continuous fermentation, fresh media is generally continually added with continuous separation of spent medium, which can include the product of interest, such as, for example, muconate, 2H3M4OP, p-toluate or terephthalate, when the product is secreted. One feature of the continuous culture is that a time-independent steady-state can be obtained which enables one to determine the relations between microbial behavior and the environmental conditions. Achieving this steady-state is accomplished by means of a chemostat, or similar bioreactor. A chemostat allows for the continual addition of fresh medium while culture liquid is continuously removed to keep the culture volume constant. By altering the rate at which medium is added to the chemostat, the growth rate of the non-naturally occurring microbial organism can be controlled.

The continuous and/or near-continuous production of a compound of interest, such as, for example, muconate, 2H3M4OP, p-toluate or terephthalate, can include culturing a compound-producing non-naturally occurring microbial organism in sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, organisms that produce a compound of interest can be cultured for hours, if suitable for a particular application. It is to be understood that the continuous and/or near-continuous culture conditions also can include all time intervals in between these exemplary periods. It is further understood that the time of culturing the compound-producing non-naturally occurring microbial organism is for a sufficient period of time to produce a sufficient amount of product for a desired purpose.

In certain embodiments, the culture can be conducted under aerobic conditions. An oxygen feed to the culture can be controlled. Oxygen can be supplied as air, enriched oxygen, pure oxygen or any combination thereof. Methods of monitoring oxygen concentration are known in the art. Oxygen can be delivered at a certain feed rate or can be delivered on demand by measuring the dissolved oxygen content of the culture and feeding accordingly with the intention of maintaining a constant dissolved oxygen content.

Fermentations can be performed under anaerobic conditions. For example, as explained above, the culture can be rendered substantially free of oxygen by first sparging the medium with nitrogen and then sealing culture vessel (e.g., flasks can be sealed with a septum and crimp-cap). Microaerobic conditions also can be utilized by providing a small hole for limited aeration. On a commercial scale, microaerobic conditions are achieved by sparging a fermentor with air or oxygen as in the aerobic case, but at a much lower rate and with tightly controlled agitation.

If desired, the pH of the medium can be maintained at a desired pH, in particular neutral pH, such as a pH of around 7 by addition of a base, such as NaOH or other bases, or acid, as needed to maintain the culture medium at a desirable pH.

The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example: sugars such as glucose, xylose, arabinose, galactose, mannose, fructose, sucrose and starch; glycerol; carbon dioxide; formate; methane; methanol; or a carbon source generated from electrochemical conversion of carbon dioxide, such as formate or methanol, alone as the sole source of carbon or in combination with other carbon sources described herein or known in the art. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 2H3M4OP, p-toluate or terephthalate.

In addition to renewable feedstocks such as those exemplified above, the 2H3M4OP, p-toluate or terephthalate microbial organisms of the invention also can be modified for growth on syngas as its source of carbon. In this specific embodiment, one or more proteins or enzymes are expressed in the 2H3M4OP, p-toluate or terephthalate producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

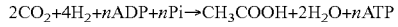

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a 2H3M4OP, p-toluate or terephthalate pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl- CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the 2H3M4OP, p-toluate or terephthalate precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a 2H3M4OP, p-toluate or terephthalate pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains a reductive TCA pathway can confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, 2H3M4OP, p-toluate or terephthalate and any of the intermediate metabolites in the 2H3M4OP, p-toluate or terephthalate pathway. All that is required is to engineer in one or more of the required enzyme or protein activities to achieve biosynthesis of the desired compound or intermediate including, for example, inclusion of some or all of the 2H3M4OP, p-toluate or terephthalate biosynthetic pathways. Accordingly, the invention provides a non-naturally occurring microbial organism that produces and/or secretes 2H3M4OP, p-toluate or terephthalate when grown on a carbohydrate or other carbon source and produces and/or secretes any of the intermediate metabolites shown in the 2H3M4OP, p-toluate or terephthalate pathway when grown on a carbohydrate or other carbon source. The 2H3M4OP, p-toluate or terephthalate producing microbial organisms of the invention can initiate synthesis from an intermediate. For example, a 2H3M4OP pathway intermediate can be 4-phosphoerythronate, 2-oxo-3-hydroxy-4-phosphobutanoate, 2-acetyl-2,3-phosphodutanoate, 2-acetyl-2,3-dihydroxy-4-phosphobutanoate, 2,3,4-trihydroxy-3-methyl-5-phosphopentanoate, 4-hydroxy-3-methyl-2-oxo-5-phosphopentanoate, 4,5-dihydroxy-3-methyl-2-oxopentanoate, 4-hydroxy-2-oxo-5-phosphopentanoate, 1-deoxy-D-xylulose-5-phosphate or C-methyl-D-erythritol-4-phosphate (see Examples I and II and FIGS. 1-3). A p-toluate pathway intermediate can be, for example, 2,4-dihydroxy-5-methyl-6-[(phosphonooxy)methyl]oxane-2-carboxylate, 1,3-dihydroxy-4-methyl-5-oxocyclohexane-1-carboxylate, 5-hydroxy-4-methyl-3-oxocyclohex-1-ene-1-carboxylate, 3,5-dihydroxy-4-methylcyclohex-1-ene-1-carboxylate, 5-hydroxy-4-methyl-3-(phosphonooxy)cyclohex-1-ene-1-carboxylate, 5-[(1-carboxyeth-1-en-1-yl)oxy]-4-methyl-3-(phosphonooxy)cyclohex-1-ene-1-carboxylate, or 3-[(1-carboxyeth-1-en-1-yl)oxy]-4-methylcyclohexa-1,5-diene-1-carboxylate (see Example II and FIG. 2). A terephthalate intermediate can be, for example, 4-carboxybenzyl alcohol or 4-carboxybenzaldehyde (see Example III and FIG. 3).

The non-naturally occurring microbial organisms of the invention are constructed using methods well known in the art as exemplified herein to exogenously express at least one nucleic acid encoding a 2H3M4OP, p-toluate or terephthalate pathway enzyme or protein in sufficient amounts to produce 2H3M4OP, p-toluate or terephthalate. It is understood that the microbial organisms of the invention are cultured under conditions sufficient to produce 2H3M4OP, p-toluate or terephthalate. Following the teachings and guidance provided herein, the non-naturally occurring microbial organisms of the invention can achieve biosynthesis of 2H3M4OP, p-toluate or terephthalate resulting in intracellular concentrations between about 0.1-200 mM or more. Generally, the intracellular concentration of 2H3M4OP, p-toluate or terephthalate is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the 2H3M4OP, p-toluate or terephthalate producers can synthesize 2H3M4OP, p-toluate or terephthalate at intracellular concentrations of 5-10 mM or more as well as all other concentrations exemplified herein. It is understood that, even though the above description refers to intracellular concentrations, 2H3M4OP, p-toluate or terephthalate producing microbial organisms can produce 2H3M4OP, p-toluate or terephthalate intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g. toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth conditions for achieving biosynthesis of 2H3M4OP, p-toluate or terephthalate can include the addition of an osmoprotectant to the culturing conditions, as described, for example, in U.S. Patent Publication No. US 2011/0207185 A1.

In addition to the culturing and fermentation conditions disclosed herein, growth condition for achieving biosynthesis of 2H3M4OP, p-toluate or terephthalate can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylpropionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in 2H3M4OP, p-toluate or terephthalate or any 2H3M4OP, p-toluate or terephthalate pathway intermediate. The various carbon feedstock and other uptake sources enumerated above will be referred to herein, collectively, as "uptake sources." Uptake sources can provide isotopic enrichment for any atom present in the product 2H3M4OP, p-toluate or terephthalate or 2H3M4OP, p-toluate or terephthalate pathway intermediate, or for side products generated in reactions diverging away from a 2H3M4OP, p-toluate or terephthalate pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the bio-based content of solid, liquid, and gaseous samples using radiocarbon dating by the American Society for Testing and Materials (ASTM) International. The standard is based on the use of radiocarbon dating for the determination of a product's bio-derived content. ASTM D6866 was first published in 2004, and the current active version of the standard is ASTM D6866-11 (effective Apr. 1, 2011). Radiocarbon dating techniques are well known to those skilled in the art, including those described herein.

The bio-based content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of 1.176±0.010×10$^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes bio-based sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new bio-based products are produced in a post-bomb environment, all pMC values (after correction for isotopic fraction) must be multiplied by 0.95 (as of 2010) to better reflect the true bio-based content of the sample. A bio-based content that is greater than 103% suggests that either an analytical error has occurred, or that the source of bio-based carbon is more than several years old.

ASTM D6866 quantifies the bio-based content relative to the material's total organic content and does not consider the inorganic carbon and other non-carbon containing substances present. For example, a product that is 50% starch-based material and 50% water would be considered to have a Bio-derived Content=100% (50% organic content that is 100% bio-based) based on ASTM D6866. In another example, a product that is 50% starch-based material, 25% petroleum-based, and 25% water would have a Bio-derived Content=66.7% (75% organic content but only 50% of the product is bio-based). In another example, a product that is 50% organic carbon and is a petroleum-based product would be considered to have a Bio-derived Content=0% (50% organic carbon but from fossil sources). Thus, based on the well known methods and known standards for determining the bio-based content of a compound or material, one skilled in the art can readily determine the bio-derived content and/or prepared downstream products that utilize of the invention having a desired bio-based content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., *supra*, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides 2H3M4OP, p-toluate or terephthalate or a 2H3M4OP, p-toluate or terephthalate pathway intermediate that has a carbon-12, carbon-13, and carbon-14 ratio that reflects an atmospheric carbon, also referred to as environmental carbon, uptake source. For example, in some aspects the 2H3M4OP, p-toluate or terephthalate or a 2H3M4OP, p-toluate or terephthalate pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides 2H3M4OP, p-toluate or terephthalate or a 2H3M4OP, p-toluate or terephthalate pathway intermediate that has a carbon-12, carbon-13, and carbon-14 ratio that reflects petroleum-based carbon uptake source. In this aspect, the 2H3M4OP, p-toluate or terephthalate or a 2H3M4OP, p-toluate or terephthalate pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides 2H3M4OP, p-toluate or terephthalate or a 2H3M4OP, p-toluate or terephthalate pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced 2H3M4OP, p-toluate or terephthalate or a 2H3M4OP, p-toluate or terephthalate pathway intermediate as disclosed herein, and to the products derived therefrom, wherein the 2H3M4OP, p-toluate or terephthalate or a 2H3M4OP, p-toluate or terephthalate pathway intermediate has a carbon-12, carbon-13, and carbon-14 isotope ratio of about the same value as the $CO_2$ that occurs in the environment. For example, in some aspects the invention provides bio-based 2H3M4OP, p-toluate or terephthalate or a bio-based 2H3M4OP, p-toluate or terephthalate intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bio-based 2H3M4OP, p-toluate or terephthalate or a bio-based 2H3M4OP, p-toluate or terephthalate pathway intermediate as disclosed herein, wherein the bio-based product is chemically modified to generate a final product. Methods of chemically modifying a bio-based product of 2H3M4OP, p-toluate or terephthalate, or an intermediate thereof, to generate a desired product are well known to those skilled in the art, as described herein. The invention further provides a chip, resin, fiber, film or any other product described herein having a carbon-12 versus carbon-13 versus carbon-14 isotope ratio of about the same value as the $CO_2$ that occurs in the environment, wherein the chip, resin, fiber, film or any other product described herein is generated directly from or in combination with bio-based 2H3M4OP, p-toluate or terephthalate or a bio-based 2H3M4OP, p-toluate or terephthalate pathway intermediate as disclosed herein.

The terephthalate produced by the microbial organisms, pathways, fermentation process and/or isolation or purification processes described herein can be used as a precursor of polymers including PET, polybutyl terephthalate (PBT), polytrimethylene terephthalate (PTT), and polyethylene naphthalate (PEN). Accordingly, the resulting bio-derived polymer can contain terephthalate, comprise terephthalate, be obtained with terephthalate, be obtained by using terephthalate, be made by using terephthalate, be obtained by converting terephthalate, or be obtained by a reaction using terephthalate, wherein the terephthalate is produced by a microbial organism, pathway, fermentation process and/or isolation or purification process described herein. Moreover, in some aspects, the invention provides use of a bio-derived polymer described herein to make a product disclosed herein. Still further, the invention provides, in some aspects, use of a product disclosed herein in making a composition, product or article.

When both a bio-based terephthalate of the invention and a second non-bio-based terephthalate, such as a petroleum-derived terephthalate or a terephthalate not made or obtained according to the present invention, are present in the same composition or product, such as a polymer, chip, fiber, resin, film or any other product described herein, the bio-based terephthalate can be present in an amount from 5% by weight to 100% by weight based on the total weight of the bio-based terephthalate and the second non-bio-based terephthalate present in the composition or product. In some aspects, the bio-based terephthalate can be from 25% by weight to 100% by weight; or alternatively, from 50% by weight to 100% by weight.

When both a polymer of the invention, i.e. a bio-derived polymer, and a second polymer such as a petroleum based polymer or a polymer not made or obtained by the bio-based terephthalate of the invention are present in the same composition or product, e.g. resin, chip, fiber, film, or any other product described herein, the bio-derived polymer can be present in an amount from 5% by weight to 100% by weight based on the total weight of the bio-derived polymer and the second polymer present in the composition or product. In some aspects, the bio-derived polymer can be present in an amount from 25% by weight to 100% by weight, or alternatively, from 50% by weight to 100% by weight.

In certain embodiments, the invention provides a PET polymer used in polyester products and methods described herein. PET can also be referred to as melt-phase PET resin, reactor-grade polyester or polyester chip, e.g. PET bottle chips. A PET based polymer can be used in the production of polyester fibers or filaments, polyester film, solid-state (bottle-grade) resins and PET engineering resins of the invention. Polyethylene terephthalate used to make synthetic fibers is often referred to as polyester and can be used to make bottle and packaging, which are often referred to by its acronym PET. Products of the invention using polyester fibers include cloth, clothing, bedding, furniture, and carpet. Products of the invention using Bottle Grade PET include beverage, food and pharmaceutical containers and packaging, including beverage bottles. Polyester films or sheets include those having a single layer or a multilayer, a heat-shrinkable film, hollow containers, formed articles, fibers, having a coating material of the solution type, having a coating of the powder type, having a toner and having an adhesive. Products of the invention using polyester film include coated and uncoated film, and includes an Adhesion Film, a Barrier Film, a Coated Film, a Heat Sealable Film, a Lidding Film, a Matte Film, a Siliconized Release Film and/or a UV Stabilized film. Polyester film used for packaging can be coated or uncoated, and can be a Matte Film, High COF (coefficient of friction) Film, Direct Extrudable Film, UV Stabilized Film, Cold Seal Film, White Film, Weldable Film, thermal lamination film, and Peelable Film. Polyester film can also be used in products and uses including: a balloon; as electrical shrink tubing, and electrical wire and cable wraps; as a release liner in multilayer ceramic capacitor (MLCC) and ceramic casting; as a layer or backing for a photovoltaic apparatus such as a photovoltaic solar module or used as a part of the construction for coated flexible photovoltaic solar module; in presentation and display media, printing and pre-press film, overhead transparencies, photo-tool, medical and x-ray film and plates, printing plates, reprographic films, and digital imaging film, for example as used with a printer; for industrial applications as a Roll Leaf, Protective Face Shield or Window Box; for construction industry products including a shingle release liner, peel and stick release liner, flexible ductwork, fiberglass roofing, fiberglass tubing, carpet backing, flooring foam substrate, adhesive pads for carpet tile installation, acoustical panel, ceiling panel, and solar window and safety film; and a Thermal Transfer Ribbons (TTR) for use in thermal transfer printing. An example of such films include those under trade name Hostaphan® (Mitsubishi Polyester Film, Japan) and Mylar®, Melinex®, and Tetoron® (DuPont USA and Teijin Japan).

PET of the invention can be produced by polycondensation of ethylene glycol with either dimethyl terephthalate or terephthalic acid of the invention. For example, with dimethyl terephthalate, a transesterification reaction can be sued, or with terephthalic acid, an esterification reaction can be sued (Köpnick et al. "Polyesters" in Ullmann's Encyclopedia of Industrial Chemistry, A21, Wiley-VCH, Weinheim, 2000). Dimethyl terephthalate can also be produced by di-esterification of terephthalate of the invention and methanol (Sheehan, "Terephthalic Acid, Dimethyl Terephthalate, and Isophthalic Acid" in Ullmann's Encyclopedia of Industrial Chemistry, Wiley-VCH, Weinheim, 2005). Accordingly, in certain embodiments, the invention provides a process for obtaining polyethylene terephthalate by reacting ethylene glycol with dimethyl terephthalate, wherein the dimethyl terephthalate is produced from terephthalate produced by or obtained from a microorganism, pathway, fermentation process and/or isolation or purification process described herein. In another embodiment is a process for obtaining polyethylene terephthalate by reacting ethylene glycol with terephthalate, wherein the terephthalate is produced by or obtained from a microorganism, pathway, fermentation process and/or isolation or purification process described herein.

Accordingly, in certain embodiments, the invention provides polyethylene terephthalate obtained by a process using any of the microorganisms, processes and embodiments described herein. Also provided is polyethylene terephthalate polymer obtained from terephthalate obtained by a process with any of the microorganisms, processes and embodiments described herein claims. Still further provided is polyester chip, resin or fiber comprising or obtained by using polyethylene terephthalate obtained by a process with any of the microorganisms, processes and embodiments described herein claims. Also provided is a product, as well as a process to obtain that product, as described herein above, e.g. a polyester cloth, carpet, film, comprising or obtained by using polyester fiber obtained by terephthalate as disclosed herein. Also provided is a product, as well as a process to obtain that product, as described herein, for example, a PET bottle or PET container or packaging, comprising or obtained by using PET chip or resin obtained by terephthalate as disclosed herein. In another embodiment are PET bottle chips, or method of their making, comprising or obtained by using PET obtained by a process as described herein. Further disclosed is a PET bottle, container or package comprising or obtained by using PET bottle chips obtained as described herein.

In certain embodiments, the invention provides a polybutyl terephthalate (PBT) polymer that can be used in PBT products and processes of the invention as described herein. PBT polymer can be used in molded articles, for example, injection-molded products and parts, including automotive parts, in extrusion resin, in electrical and automotive parts, and in casings, for example, power tool casings. Products include those containing PBT sold under the trade name Advanite (SASA), Anjacom (Almaak International), Arnite (DSM), Celanex, Vandar polyester alloy (Ticona), Duranex (Polyplastics), Crastin (DuPont), Pocan (Lanxess), Ultradur (BASF), Valox (SABIC Innovative Plastics), Schuladur (A. Schulman), Later (LATI), Kebater (BARLOG plastics), VESTODUR (Evonik Degussa), and ENVIRON® (Enviroplas). A PBT polymer of the invention can be produced by reaction of 1,4-butanediol with terephthalic acid of the invention, for example by esterification. Accordingly, in one embodiment, the invention provides a process for obtaining PBT by reacting 1,4-butanediol with terephthalate where the terephthalate is obtained by or produced from a microorganism, pathway, fermentation process and/or isolation or purification process described herein.

In certain embodiments, the invention provides polytrimethylene terephthalate (PTT) polymer that can be used in PTT products and processes of the invention as described herein. A PTT polymer can be used in fibers to make products, such as cloth, clothing and carpet, or bulk products such as, for example, chips for the manufacture of bottles. PTT can be prepared by the esterification of 1,3-propanediol with terephthalic acid, or by transesterification of dimethyl terephthalate, where the terephthalate is obtained by or produced from a microorganism, pathway, fermentation process and/or isolation or purification process described herein. Products and processes of the invention include those that comprise PBT polymer that is sold under the trade name Sorona (DuPont), and includes co-polymers, for example, a poly(trimethylene terephthalate) copolymer (e.g. Tritan by Eastman) and as used to produce Nalgene bottles.

The polymers of the present invention may further comprise additional compounds. Additional compounds include a solvent; one or more other bio-derived polymers described herein; one or more resins including polyester, aliphatic polyester resins, thermoplastic polyester elastomers, polyolefins, polystyrenes, acrylonitrile-butadiene-styrene copolymers, polymethyl methacrylate, polysulfones, polyethers, phenoxy resins, polyphenylene oxides, thermoplastic resins such as polyethylene, polypropylene, acrylic resins, polycarbonates, polyamides, polyphenylene sulfide, polyethylene terephthalate, liquid crystalline polyesters, polyacetals and polyphenylene oxide and thermosetting resins such as phenol resins, melamine resins, silicone resins and epoxy resins (which may be added when a molded article is prepared); and/or one or more auxiliary agents. Auxiliary agents can be added during the polymerization to form the bio-derived polymer or after the polymerization. Auxiliary agents include those for molding and additives such as fillers, coloring agents, reinforcing materials, surface-smoothing agents, leveling agents, accelerators for a curing reaction, photostabilizers, ultraviolet absorbers, plasticizers, antioxidants, extenders, delustering agents, agents for adjusting drying, antistatic agents, agents for preventing precipitating, surfactants, agents for improving flow, drying oils, waxes and thermoplastic oligomers, stabilizers including heat and UV stabilizers, lubricants, catalyst deactivators, nucleating agents for crystallization and promoters for crystallization. To provide the bio-polymer with desired properties, ultraviolet absorbents, stabilizers such as weathering stabilizers, coloring agents such as dyes, antistatic agents, foaming agents, plasticizers and impact resistance improvers can be added. Reinforcing fillers added to the resin of the present invention are not particularly limited, examples include inorganic fibers such as glass fiber, carbon fiber, silica-alumina fiber, zirconia fiber, boron fiber, boron nitride fiber, silicon nitride potassium titanate fiber and metal fibers; and organic fibers such as aromatic polyamide fibers and fluoro-resin fibers. Other fillers include inorganic fillers having a plate shape, ceramic beads, wollastonite, talc, clay, mica, zeolite, kaolin, potassium titanate, barium sulfate, titanium oxide, silicon oxide, aluminum oxide and magnesium hydroxide. By adding an inorganic filler having a plate shape, anisotropy and warp in the molded article can be decreased. Preferable examples of the inorganic filler having a plate shape include glass flakes, mica and metal foils. Among these inorganic fillers having a plate shape, glass flakes are more preferably used. Antioxidants include phenolic antioxidants, sterically hindered phenols and/or phosphites, hydroquinones, aromatic secondary amines, such as diphenylamines, and various substituted representatives of these groups. UV stabilizers include various substituted resorcinols, salicylates, benzotriazoles, and benzophenones. Coloring agents that can be added comprise inorganic and organic pigments, and also dyes, such as nigrosin and anthraquinones. Lubricants and mold-release agents include long-chain fatty acids (e.g. stearic acid or behenic acid), salts of these (e.g. Ca stearate or Zn stearate), or montan waxes (mixtures made of straight-chain, saturated carboxylic acids having chain lengths of from 28 to 32 carbon atoms), Ca montanate or Na montanate, low-molecular-weight polyethylene waxes or low-molecular-weight polypropylene waxes.

The bio-derived polymers of the present invention can be molded in accordance with a conventional process suitable for each application. For example, molded articles can be prepared in accordance with the conventional injection molding process and sheets and films can be prepared in accordance with the extrusion process or the casting process. Formed articles can be prepared in accordance with the extrusion-expansion process or the expansion-in-mold process. A molding process conventionally used for thermoplastic resins such as the injection molding, the blow molding, the extrusion molding and the compression molding can be applied.

In some embodiments, the invention provides chip, resin, fiber, film or any other product described herein comprising bio-based 2H3M4OP, p-toluate or terephthalate, or a bio-based 2H3M4OP, p-toluate or terephthalate pathway intermediate, wherein the bio-based 2H3M4OP, p-toluate or terephthalate, or bio-based 2H3M4OP, p-toluate or terephthalate pathway intermediate includes all or part of the 2H3M4OP, p-toluate or terephthalate, or 2H3M4OP, p-toluate or terephthalate pathway intermediate used in the production of chip, resin, fiber, film or any other product described herein. For example, the final chip, resin, fiber, film or any other product described herein can contain the bio-based 2H3M4OP, p-toluate or terephthalate, 2H3M4OP, p-toluate or terephthalate pathway intermediate, or a portion thereof that is the result of the manufacturing of chip, resin, fiber, film or any other product described herein. Such manufacturing can include chemically reacting the bio-based 2H3M4OP, p-toluate or terephthalate or bio-based 2H3M4OP, p-toluate or terephthalate pathway intermediate (e.g. chemical conversion, chemical functionalization, chemical coupling, oxidation, reduction, polymerization, copolymerization and the like) into the final chip, resin, fiber, film or any other product described herein. Thus, in some aspects, the invention provides a bio-derived chip, resin, fiber, film or any other product described herein comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bio-based 2H3M4OP, p-toluate or terephthalate or bio-based 2H3M4OP, p-toluate or terephthalate pathway intermediate as disclosed herein.

Additionally, in some embodiments, the invention provides a composition having a bio-based 2H3M4OP, p-toluate or terephthalate or 2H3M4OP, p-toluate or terephthalate pathway intermediate disclosed herein and a compound other than the bio-based 2H3M4OP, p-toluate or terephthalate or 2H3M4OP, p-toluate or terephthalate pathway intermediate. For example, in some aspects, the invention provides a bio-derived chip, resin, fiber, film or any other product described herein wherein the 2H3M4OP, p-toluate or terephthalate, or 2H3M4OP, p-toluate or terephthalate pathway intermediate used in its production is a combination of bio-based and petroleum derived 2H3M4OP, p-toluate or terephthalate, or 2H3M4OP, p-toluate or terephthalate pathway intermediate. For example, a bio-derived chip, resin, fiber, film or any other product described herein can be produced using 50% bio-based 2H3M4OP, p-toluate or terephthalate and 50% petroleum derived 2H3M4OP, p-toluate or terephthalate or other desired ratios such as 60%/40%, 70%/30%, 80%/20%, 90%/10%, 95%/5%, 100%/0%, 40%/60%, 30%/70%, 20%/80%, 10%/90% of bio-based/petroleum derived precursors, so long as at least a portion of the product comprises a bio-based product produced by the microbial organisms disclosed herein. It is understood that methods for producing chip, resin, fiber, film or any other product described herein using the bio-based 2H3M4OP, p-toluate or terephthalate or bio-based 2H3M4OP, p-toluate or terephthalate pathway intermediate of the invention are well known in the art.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of 2H3M4OP, p-toluate or terephthalate includes anaerobic culture or fermentation conditions. In certain embodiments, the non-naturally occurring microbial organisms of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of 2H3M4OP, p-toluate or terephthalate. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 2H3M4OP, p-toluate or terephthalate. Generally, and as with non-continuous culture procedures, the continuous and/or near-continuous production of 2H3M4OP, p-toluate or terephthalate will include culturing a non-naturally occurring 2H3M4OP, p-toluate or terephthalate producing organism of the invention in sufficient nutrients and medium to sustain and/or nearly sustain growth in an exponential phase. Continuous culture under such conditions can include, for example, growth for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of 2H3M4OP, p-toluate or terephthalate can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the 2H3M4OP, p-toluate or terephthalate producers of the invention for continuous production of substantial quantities of 2H3M4OP, p-toluate or terephthalate, the 2H3M4OP, p-toluate or terephthalate producers also can be, for example, simultaneously subjected to chemical synthesis and/or enzymatic procedures to convert the product to other compounds or the product can be separated from the fermentation culture and sequentially subjected to chemical and/or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 2H3M4OP, p-toluate or terephthalate.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a 2H3M4OP, p-toluate or terephthalate pathway can be introduced into a host organism. In some cases, it can be desirable to modify an activity of a 2H3M4OP, p-toluate or terephthalate pathway enzyme or protein to increase production of 2H3M4OP, p-toluate or terephthalate. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a 2H3M4OP, p-toluate or terephthalate pathway enzyme or protein. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

Isolation (Purification) Process of the Invention

Provided herein are processes for isolating a bio-based aromatic carboxylic acid such as, for example, p-toluic acid or terephthalic acid, from a culture medium, wherein the processes comprise lowering the pH of the culture medium to produce an aromatic carboxylic acid precipitate. In certain embodiments, lowering the pH of the culture medium comprises contacting the culture medium with carbon dioxide to lower the pH of the culture medium. In certain embodiments, a process as provided herein further comprises culturing a non-naturally occurring microbial organism in a culture medium at a pH sufficient to produce a bio-based aromatic carboxylic acid which will be in an anionic, soluble form in the culture medium.

As used herein, a "bio-based aromatic carboxylic acid" means an aromatic carboxylic acid made biosynthetically from a non-naturally occurring microbial organism.

An aromatic carboxylic acid such as terephthalic acid can be precipitated directly out of a culture medium to substantially deplete the medium of the acid or its conjugate anion. In certain embodiments, the bio-based aromatic carboxylic acid anion can have an ammonium counterion in the culture medium. Moreover, such embodiments where carbon dioxide is used to lower the pH to produce a bio-based aromatic acid precipitate, it will be understood that ammonium carbonate will result which can be easily recovered as ammonia and carbon dioxide, which components may be separated, recovered and recycled. In certain embodiments, the carbon dioxide source for acidifying the culture medium will be that collected as produced from culturing the non-naturally occurring microbial organism.

Culturing the Microbial Organism to Produce the Aromatic Carboxylate Anion

In certain embodiments, the aromatic carboxylate anion is produced by an indirect semi-synthetic route, whereby muconate is biosynthesized in a non-naturally occurring microbial organism from simple carbohydrate feedstocks, which in turn provides a viable synthetic route to the aromatic carboxylate anion, for example, terephthalate, as disclosed in U.S. Patent Publication No. US 2011/0124911 A1, hereby incorporated by reference in its entirety for all purposes. In particular, these pathways provide trans,trans-muconate or cis,trans-muconate biocatalytically from simple sugars. The all trans or cis,trans isomer of muconate may then be converted to terephthalate in a two step process via inverse electron demand Diels-Alder reaction with acetylene followed by oxidation in air or oxygen. The Diels-Alder reaction between muconate and acetylene proceeds to form cyclohexa-2,5-diene-1,4-dicarboxylate (P1) (see FIG. 1 of U.S. Patent Publication No. US 2011/0124911 A1, hereby incorporated by reference). Subsequent exposure to air or oxygen rapidly converts P1 to terephthalate.

In certain embodiments, the Diels-Alder reaction between muconate and acetylene can be performed in the culture medium. Optionally, the culture medium can be filtered, for example, to remove cells of the organism, prior to adding acetylene.

In certain embodiments, the pH sufficient to maintain the muconate in soluble form is between about 5.0-9.0, between about 5.5-9.0, between about 6.0-9.0, between about 6.5-9.0, between about 7.0-9.0, between about 5.5-8.0, between about 6.0-8.0, or between about 6.5-8.0 pH units. In certain embodiments, the pH sufficient to maintain the muconate in soluble form is about 5.5, about 6.0, about 6.5, about 7.0, about 7.5, about 8.0, or about 8.5 pH units. In certain embodiments, the pH sufficient to maintain the muconate in soluble form is about 7.0 pH units. In certain embodiments, the pH sufficient to maintain the muconate in soluble form is a neutral pH, for example a pH of about 7.0 typically bounded on its lower end by pH of about 5.0, 5.5 or 6.0 and on its upper end by a pH of about 9.0, 8.5 or 8.0.

The pH of the culture medium can be maintained at a desired pH, for example, a pH between about 5.0-9.0, by addition of a base, such as NaOH or other bases, or acid, as needed to maintain the culture medium at the desired pH. It will be understood that a pH between about 5.0-9.0 can, for example, be conducive for optimal culturing conditions to produce a desired product (e.g., a bio-based aromatic carboxylate anion or a precursor) and/or to produce an anionic form in a soluble form in culture medium. In certain embodiments, a base is added to the culture medium in sufficient quantities to maintain muconate in soluble form. In certain embodiments, a base is added to the culture medium in sufficient quantities to maintain the culture medium at a pH between about 5.0-9.0.

In certain embodiments, following the Diels-Alder reaction, the culture medium can be separated from the cells and/or any non-soluble material by, for example, centrifugation or membrane filtration, to provide a cell-free medium or broth comprising the terephthalate, prior to the contacting step (described herein and in section "Acidification of the Culture Medium to Precipitate the Aromatic Carboxylic Acid"). For convenience, the culture medium or broth separated from the non-soluble materials will be termed "cell-free." Those skilled in the art will understand that medium and broth can be used interchangeably throughout to refer to a liquid or gel designed to support the growth of the non-naturally occurring microbial organism.

In certain embodiments, the aromatic carboxylate anion is produced by a direct biosynthetic route, whereby the aromatic carboxylate anion, for example, p-toluate or terephthalate, is biosynthesized in a non-naturally occurring microbial organism from simple carbohydrate feedstocks, as disclosed in U.S. Patent Publication No. US 2011/0207185 A1, which is hereby incorporated by reference in its entirety for all purposes.

Exemplary biosynthetic pathways include, for example, the conversion of erythrose-4-phosphate to (2-hydroxy-3-methyl-4-oxobutoxy)phosphonate (2H3M4OP), also known as 3-hydroxy-2-methyl butanal-4-phosphate, in six enzymatic steps (see FIG. 1). In one alternative, 4,5-dihydroxy-2-oxopentanoate is converted to 2H3M4OP using one or both of the pathways described in FIG. 2. In another alternative, glyceraldehyde-3-phosphate (G3P) and pyruvate are converted to 2H3M4OP in three enzymatic steps (see FIG. 3). The 2H3M4OP intermediate can be subsequently transformed to p-toluate by enzymes in the shikimate pathway (see FIG. 4). p-Toluate can be further converted to terephthalate by a microorganism (see FIG. 5). The purification method of the invention (exemplified in FIG. 6) can also be applied to biosynthetic pathways for aromatic carboxylic acid and terephthalic acid production described in WIPO patent publications WO/2009/120457A2 entitled "Bio-Based Polyethylene Terephthalate Polymer And Method Of Making The Same", WO/2011/094131A1 entitled "Microorganisms And Methods For The Biosynthesis Of P-Toluate And Terephthalate", and WO/2011/017560A1 entitled "Semi-Synthetic Terephthalic Acid Via Microorganisms That Produce Muconic Acid" and U.S. Pat. No. 6,461,840 entitled "Terephthalic acid producing proteobacteria" and U.S. Pat. No. 6,187,569 entitled "Microbial production of terephthalic acid and isophthalic acid."

In certain embodiments, the pH sufficient to maintain the p-toluate or terephthalate in soluble form is between about 5.0-9.0, between about 5.5-9.0, between about 6.0-9.0, between about 6.5-9.0, between about 7.0-9.0, between about 5.5-8.0, between about 6.0-8.0, or between about 6.5-8.0 pH units. In certain embodiments, the pH sufficient to maintain the p-toluate or terephthalate in soluble form is about 5.5, about 6.0, about 6.5, about 7.0, about 7.5, about 8.0, or about 8.5 pH units. In certain embodiments, the pH sufficient to maintain the p-toluate or terephthalate in soluble form is about 7.0 pH units. In certain embodiments, the pH sufficient to maintain p-toluate or terephthalate in soluble form is a neutral pH, for example a pH of about 7.0 typically bounded on its lower end by pH of about 5.0, 5.5 or 6.0 and on its upper end by a pH of about 9.0, 8.5 or 8.0.

The pH of the culture medium can be maintained at a desired pH, which can, for example, be a pH between about 5.0-9.0, by addition of a base or acid, as needed to maintain the culture medium at the desired pH.

Those of skill in the art will understand that the dianionic salts of terephthalic acid are soluble at concentrations >100 g/L (up to 13% by weight) at 25° C. In certain embodiments, a base is added to the culture medium in sufficient quantities to maintain terephthalic acid in soluble form. In certain embodiments, a base is added to the culture medium in sufficient quantities to maintain the culture medium at a pH between about 5.0-9.0.

It will be understood that counterions, including for instance, sodium, potassium, ammonium, among others, can be added to the culture medium to produce a desired counterion to an aromatic carboxylate anion, to the extent that the form of the counterion, when added, maintains a desired pH. In certain embodiments, a base, such as sodium hydroxide (NaOH), potassium hydroxide (KOH), sodium bicarbonate ($NaHCO_3$), or other bases, or acid, are added as needed to maintain the culture medium at a desirable pH.

In certain embodiments, anhydrous ammonia ($NH_3$) is added as a base to the culture medium to maintain the pH around 7. In certain embodiments, a solution of ammonia, also known as ammonium hydroxide ($NH_4OH$), ammonia water, ammonical liquor, ammonia liquor, aqua ammonia, aqueous ammonia, or ammonia, is added as a base to the culture medium to maintain the pH around 7. Use of ammonia as a base offers certain advantages for recovery and recycling of salts in the processes disclosed herein (described herein and in section entitled "Recovery of Salts for Recycling").

Those skilled in the art will understand that the aromatic carboxylate anions produced by the biosynthetic routes described herein, i.e., p-toluate and terephthalate, will be in the form of soluble carboxylate salts, i.e., the carboxylate anions will be solvated in solution with a counter ion (a cation) in the culture medium. The choice of base used to maintain the culture medium at a neutral pH will determine the counter ion and the type of salt. For example, where a sodium base, such as NaOH or $NaHCO_3$ is used to maintain neutral pH, the counter ion will be sodium ($Na^+$), and a soluble sodium carboxylate salt will be formed. Similarly, where KOH is used, the counter ion will be potassium ($K^+$) and a soluble potassium carboxylate salt will be formed. Where ammonia is used, the counter ion will be ammonium ($NH_4^+$), and a soluble ammonium carboxylate salt will be formed. Where the aromatic carboxylic anion is a diacid, for example, terephthalate, a disalt (e.g., disodium, dipotassium, or diammonium terephthalate) will be formed.

In certain embodiments, following fermentation, the culture medium can be separated from the cells and/or any non-soluble material by, for example, centrifugation, filtration, or technique used in the art, to provide a cell-free medium or broth comprising the aromatic carboxylate anion, prior to the contacting step (described herein and in section entitled "Acidification of the Culture Medium to Precipitate the Aromatic Carboxylic Acid"). Exemplary filtrations can be micro, nano or ultra filtration. Centrifugation and filtration methods are well known to those skilled in the art.

Acidification of the Culture Medium to Precipitate the Aromatic Carboxylic Acid

In certain embodiments, the aromatic carboxylate anion produced by the biosynthetic routes described herein can be isolated by acidification of the culture medium. For example, in certain embodiments, a process is provided comprising lowering the pH of the culture medium to produce an aromatic carboxylic acid precipitate.

It will be understood that the expressions "acidifying" or "acidification" as used herein mean the addition of substance, acid or otherwise, to an aqueous solution, for example, a culture medium, to result in that solution having a lower pH. Thus, for instance, it will be recognized that contacting a culture medium with $CO_2$ is an acidification of the culture medium.

In certain embodiments, the pH of the culture medium comprising the aromatic carboxylate anion is lowered to less than about 5.0 pH units, less than about 4.5 pH units, less than about 4.0 pH units, less than about 3.5 pH units, less than about 3.0 pH units, less than about 2.5 pH units, less than about 2.0 pH units, less than about 1.5 pH units, or less than about 1.0 pH units. In certain embodiments, the pH of the culture medium is lowered to less than about 3.0 pH units. In certain embodiments, the pH of the culture medium is lowered to less than about 2.0 pH units.

Those skilled in the art will understand that the pH of the culture medium is optimally lowered to a pH value less than the pKa value of the aromatic carboxylic acid to be isolated.

In certain embodiments, the aqueous solubility of the aromatic carboxylate anions and/or salts disclosed herein is greater than about 100 g/L at room temperature. In certain embodiments, the aqueous solubility of the aromatic carboxylic acids disclosed herein is less than 1 g/L at room temperature.

In certain embodiments, acidification of the culture medium results in precipitation of the aromatic carboxylic acid. In certain embodiments, a decrease in pH of the culture medium results in precipitation of the aromatic carboxylic acid.

In certain embodiments, the precipitate is comprised of a monoacid, for example, p-toluic acid. In certain embodiments, the precipitate is comprised of a diacid, for example, terephthalic acid.

In certain embodiments, acidification results in the culture medium being substantially depleted of the aromatic carboxylate anion. In certain embodiments, a decrease in pH of the culture medium results in the culture medium being substantially depleted of the aromatic carboxylate anion. In certain embodiments, precipitation of the aromatic carboxylic acid results in the culture medium being substantially depleted of the aromatic carboxylate anion.

As used herein, the term "substantially depleted" is understood to mean that less than about 50% of the total amount of aromatic carboxylate anion produced biosynthetically remains in the culture medium following acidification. In certain embodiments, less than about 50%, less than about 40%, less than about 30%, less than about 20%, less than about 10%, less than about 5%, or less than about 1% of the aromatic carboxylate anion remains in the culture medium following acidification. In certain embodiments, "substantially depleted" means that the amount of aromatic carboxylate anion in the culture medium is less than that which can measurably detected.

In certain embodiments, the pH of the culture medium is lowered by contacting the culture medium with an acid. Such acids can, for example, be those known in the art, including, for instance, hydrochloric, phosphoric, sulfuric, and so forth. In certain embodiments, the acid is carbon dioxide. It is believed use of carbon dioxide is advantageous in that, it can, for example, be obtained as a product from the cultured microbial organism and/or easily recovered and recycled from the acidified culture medium.

In certain embodiments, the pH of the culture medium is lowered through contact with sufficient carbon dioxide ($CO_2$) to lower the pH of the culture medium to produce the precipitate comprising the aromatic carboxylic acid.

Those skilled in the art will understand that when carbon dioxide dissolves in water it exists in chemical equilibrium producing carbonic acid ($H_2CO_3$):

$$CO_2 + H_2O \rightleftharpoons H_2CO_3,$$

which in sufficient quantities can be used to lower the pH of the culture medium.

In certain embodiments, the culture medium is contacted with a solution of $CO_2$ in water, for example, a solution of carbonic acid ($H_2CO_3$). In certain embodiments, the culture medium is contacted with gaseous $CO_2$. In certain embodiments, the gaseous $CO_2$ is pure $CO_2$ gas. In certain embodiments, the gaseous $CO_2$ is in a mixture with one or more additional gases. In certain embodiments, the one or more additional gases include nitrogen, an inert gas (helium, argon, etc.), or the like.

In certain embodiments, the culture medium is stirred while it is contacted with gaseous $CO_2$.

In certain embodiments, the culture medium is contacted with gaseous $CO_2$ for up to 20 hours.

To provide sufficient $H_2CO_3$ in solution in the culture medium, the temperature and pressure of the culture medium can be adjusted. Those skilled in the art will understand that the optimum temperature and pressure will depend on the pKa of the aromatic carboxylic acid to be precipitated, the concentration of the aromatic carboxylate anion, and the fraction of aromatic carboxylate anion required to be converted to the aromatic carboxylic acid.

In certain embodiments, the culture medium is pressurized in the range of about 1 to 300 atm with $CO_2$. In certain embodiments, the culture medium is pressurized in the range of about 50 to 200 atm with $CO_2$. In certain embodiments, the culture medium is pressurized in the range of about 1 to 100 atm with $CO_2$. In certain embodiments, the culture medium is pressurized in the range of about 20 to 50 atm with $CO_2$. In certain embodiments, the culture medium is pressurized in the range of about 10 to 50 atm with $CO_2$.

More particularly, lower atmospheres of $CO_2$, between, for example, 1 to 30 atm with $CO_2$ may be useful. In certain embodiments, the culture medium is pressurized in the range of about 1 to 30 atm with $CO_2$. In certain embodiments, the culture medium is contacted with $CO_2$ under pressure in the range of about 1 to about 20 atm, about 2 to about 25 atm, about 5 to about 20 atm, about 10 to about 20 atm, about 13 to about 20 atm, about 14 to about 20 atm, about 15 to about 20 atm, about 14 to about 16 atm, about 16 to about 20 atm, about 17 to about 25 atm, about 2 to about 20 atm, or about 10 to about 16 atm. In certain embodiments, the culture medium is contacted with $CO_2$ under about 0.01, 0.1, 0.5, 1.0, 2, 5, 10, 14, 15, 16, or 20 atm with $CO_2$.

Where the culture media is contacted with "sufficient" $CO_2$, by "sufficient," it is meant that the amount $CO_2$ lowers the pH of the culture medium to result in an aromatic carboxylic acid precipitate to substantially deplete the culture medium of the aromatic carboxylate anion. In certain embodiments, "sufficient" $CO_2$ comprises contacting the culture media with $CO_2$ under a pressure and/or temperatures as described in the paragraphs above and below.

In certain embodiments, the temperature of the culture medium is in the range of about 0° C. to 90° C. In certain embodiments, the temperature of the culture medium is in the range of about 0° C. to 80° C. In certain embodiments, the temperature of the culture medium is in the range of about 0° C. to 60° C. In certain embodiments, the temperature of the culture medium is in the range of about 5° C. to 50° C. In certain embodiments, the temperature of the culture medium is in the range of about 5° C. to 10° C., 10° C. to 20° C., 20° C. to 30° C., 30° C. to 40° C., 40° C. to 50° C., or 40° C. to 60° C. In certain embodiments, the temperature of the culture medium is about 5, 10, 15, 20, 25, 30, 35, 40, 45 or 50° C.

In certain embodiments, the contacting step takes place in a vessel. In such embodiments, the pressures and temperatures, and ranges thereof, provided above are those inside the vessel.

In certain embodiments, the vessel is pressurized in the range of about 0.1 to 30 atm with $CO_2$ and the pressurized culture medium in the vessel is stirred at temperatures between about 0° C. and about 80° C. for up to 24 hours.

Trapping and Recycling Side Product from Culturing Step

In certain embodiments, a side product of the culturing step is trapped and recycled. In certain embodiments, the side product of the culturing step is $CO_2$. For example, the biosynthetic pathways to 2H3M4OP, exemplified in FIGS. 1-3, each generate one equivalent of $CO_2$. Carbon dioxide may also be produced in other metabolic pathways when culturing the non-naturally occurring microbial organism. The production of this $CO_2$ if not collected and reused represents inefficiency and, if released, has a potential to contribute to Green House Gas emissions. Production of $CO_2$ by the culture medium is considered bio-based $CO_2$ by virtue of the fact that is has the expected $^{14}C$ content measured by, for example, ASTM D6866-05 analysis methods for dating radioactive carbon.

In certain embodiments, a process as provided herein further comprises collecting $CO_2$ produced by culturing the non-naturally occurring organism. The collected $CO_2$ can, for example, be used to lower the pH of the culture medium to produce the aromatic carboxylic acid precipitate, or, for example, to supplement the $CO_2$ used to lower the pH of the culture medium.

Accordingly, one objective is to improve overall carbon capture and/or improve overall costs and efficiencies of the processes disclosed herein for isolating an aromatic carboxylic acid.

In certain embodiments, $CO_2$ generated in the biosynthesis of the aromatic carboxylic acid can be trapped and recycled for later use, using, for example, a fermentation trap or $CO_2$ capture device.

In certain embodiments, $CO_2$ generated in the biosynthesis of the aromatic carboxylic acid can be trapped and recycled for use to lower the pH of the culture medium to precipitate the aromatic carboxylic acid.

In certain embodiments, $CO_2$ generated, for example, in culturing organisms in the biosynthesis of the aromatic carboxylic acid can be trapped and recycled for use to maintain anaerobic or substantially anaerobic conditions in the culture medium.

Technologies for collecting (also termed trapping, sequestering, recovering) for $CO_2$ are known including those applicable to collecting $CO_2$ from culturing organisms. It will understood that such methods can, for example, be employed in connection with collecting $CO_2$ from the cultured organisms as described herein.

In certain embodiments, $CO_2$ generated in the biosynthesis of the aromatic carboxylic acid can be trapped and recycled for use as a source of carbon to the non-naturally occurring microorganism in the culture medium. In certain embodiments, $CO_2$ can be trapped and mixed with Synthesis gas, also known as syngas or producer gas, for use as a source of carbon to the non-naturally occurring microorganism in the culture medium, as disclosed in U.S. Patent Publication No. US 2011/0207185 A1. Syngas is a mixture primarily of $H_2$ and CO and can be obtained from the gasification of any organic feedstock, including but not limited to coal, coal oil, natural gas, biomass, and waste organic matter. Although largely $H_2$ and CO, syngas can also include $CO_2$ and other gases in smaller quantities. Thus, synthesis gas provides a cost effective source of gaseous carbon such as CO and, additionally, $CO_2$.

Recovery of Salts for Recycling

The aqueous solution remaining after the aromatic carboxylic acid is precipitated from the culture medium contains solvated salts as counter ions, which can be recovered for recycling in the processes disclosed herein. For example, where $CO_2$ is used to lower the pH of the culture medium, the aqueous solution will contain solvated carbonate salts. Where ammonia ($NH_3$) is used as a base to maintain the aromatic carboxylate anion in soluble form, the aqueous solution will contain solvated ammonium salts. Where both $NH_3$ and $CO_2$ are used, the aqueous solution will contain solvated ammonium carbonate (($NH_4$)$_2CO_3$).

In certain advantageous embodiments, it is contemplated that solvated ($NH_4$)$_2CO_3$ salt remaining in the aqueous solution following precipitation of the aromatic carboxylic acid can be recovered and recycled. For example, heating the aqueous solution will decompose the ($NH_4$)$_2CO_3$ into $NH_3$ and $CO_2$, as depicted below.

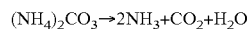

$$(NH_4)_2CO_3 \rightarrow 2NH_3 + CO_2 + H_2O$$

The resultant gaseous $NH_3$ and $CO_2$ can be separated, recovered and/or recycled using, for example, a fermentation trap or gas capture device. Recovery/recycling of gaseous $NH_3$ and $CO_2$ will reduce the costs associated with use of these materials and will also reduce environmental discharges, for example, Green House Gas emissions in the case of the $CO_2$ gas. This will further improve overall carbon capture and/or improve overall costs and efficiencies of the processes disclosed herein for isolating an aromatic carboxylic acid.

In certain embodiments, the $NH_3$ recovered from decomposition of ($NH_4$)$_2CO_3$ can be recycled for use as a base to maintain the aromatic carboxylate anion in soluble form in the culture medium.

In certain embodiments, the $CO_2$ recovered from decomposition of ($NH_4$)$_2CO_3$ can be recycled for use to lower the pH of the culture medium to precipitate the aromatic carboxylic acid.

In certain embodiments, the $CO_2$ recovered from decomposition of ($NH_4$)$_2CO_3$ can be recycled for use to maintain anaerobic or substantially anaerobic conditions in the culture medium used to produce the aromatic carboxylate anion.

In certain embodiments, the $CO_2$ recovered from decomposition of ($NH_4$)$_2CO_3$ can be recycled for use as a source of carbon to the non-naturally occurring microorganism in the culture medium.

The remaining aqueous solution will be at a higher pH, and may also be recycled for use in, for example, the culture medium. In certain embodiments, enough $CO_2$ will be removed so that the aqueous solution returns to a neutral pH to provide a neutral solution for the culture medium.

In certain embodiments, following acidification and precipitation of the aromatic carboxylic acid, the aqueous solution can be filtered to provide an aqueous filtrate from which the solvated salts may be recovered for recycling.

Separating the Aromatic Carboxylic Acid from the Culture Medium

Once precipitated, the aromatic carboxylic acid may be separated from the other components in the culture medium by removing the culture medium. In certain embodiments, the separation of the aromatic carboxylic acid from the other components in the culture medium comprises filtering and recovering of the aromatic carboxylic acid from the culture medium. In certain embodiments the precipitated aromatic carboxylic acid is resolubilized and subjected to extraction or separation procedures well know in the art, which can, for example, include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

In certain embodiments, the aromatic carboxylic acid is purified following separation from the other components in the culture medium. In certain embodiments, the aromatic carboxylic acid is purified using crystallization.

Therefore, provided herein is an isolated bio-based p-toluic acid produced by the processes described herein. Also provided herein is an isolated bio-based terephthalic acid produced by the processes described herein.

Exemplary Calculations

Dependence of Terephthalic Acid Forms on pH

The following describes exemplary calculations of dependence of terephthalic acid forms on pH.

Table 1 further demonstrates that at pH 7, close to 100% of terephthalic acid will be in the anionic form. Thus, in the processes provided herein, where the non-naturally occurring microbial organism produces terephthalate, performing the culturing step at a neutral pH will produce the anion, that is, close to 100% of terephthalic acid will be in the anionic form (terephthalate).

Similarly, a culture medium that is acidified to less than about 3.0 pH units will afford predominantly the diacid form of terephthalic acid. It will be understood that terephthalic acid is virtually insoluble in aqueous solutions (0.017 g/L solubility in water at 25° C.). In light that terephthalic acid is not soluble in aqueous solution, it is quite clear from Table 1 that acidification of the culture medium to values less than about 3.0 pH units will result in a substantial depletion of

TABLE 1

Dependence of terephthalic acid forms on pH

| pH | Total acid (mol/L) | Undissociated acid (mol/L) | Percent | Monoanionic acid (mol/L) | Percent | Dianioninc acid (mol/L) | Percent |
|---|---|---|---|---|---|---|---|
| 2 | 0.354314 | 0.344349 | 97.2% | 0.009931 | 2.8% | 3.44E−05 | 0.0% |
| 3 | 0.00421 | 0.003243 | 77.0% | 0.000935 | 22.2% | 3.24E−05 | 0.8% |
| 4 | 1E−04 | 2.05E−05 | 20.5% | 5.91E−05 | 59.1% | 2.05E−05 | 20.5% |
| 5 | 5.67E−06 | 4.37E−08 | 0.8% | 1.26E−06 | 22.2% | 4.37E−06 | 77.0% |
| 6 | 5.02E−07 | 4.88E−11 | 0.0% | 1.41E−08 | 2.8% | 4.88E−07 | 97.2% |
| 6.5 | 1.43E−07 | 1.42E−12 | 0.0% | 1.29E−09 | 0.9% | 1.42E−07 | 99.1% |

Table 1 demonstrates that at a pH value of 4, terephthalic acid forms exists in a ratio of about 20.5/59/20.5 anion to monoacid to diacid; at a pH value of 3, terephthalic acid forms exists in a ratio of about 1/22/77 anion to monoacid to diacid; at a pH value of 2, terephthalic acid forms exists in a ratio of about 0/3/97 anion to monoacid to diacid, as illustrated below.

terephthalate in the culture medium, because at values less than about 3.0 pH units, there will no soluble form of terephthalic acid remaining in the culture medium, no matter what the form (anion, monoacid or diacid).

Pressure-pH Relationship for $CO_2$ in Water

The following describes exemplary calculations of pressure-pH relationship for $CO_2$ in water.

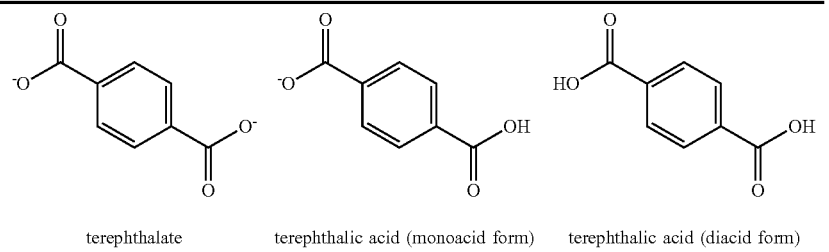

| | terephthalate | terephthalic acid (monoacid form) | terephthalic acid (diacid form) |
|---|---|---|---|
| pH | | Ratios | |
| 2 | 0 | 3 | 97 |
| 3 | 1 | 22 | 77 |
| 4 | 20.5 | 59 | 20.5 |

TABLE 2

Pressure-pH relationship for $CO_2$ in water.

| (atm) | pH | $[CO_2]$ (mol/L) | $[H_2CO_3]$ (mol/L) | $[HCO_3^-]$ (mol/L) | $[CO_3^{2-}]$ (mol/L) |
|---|---|---|---|---|---|
| $1.0 \times 10^{-8}$ | 7.00 | $3.36 \times 10^{-10}$ | $5.71 \times 10^{-13}$ | $1.42 \times 10^{-09}$ | $7.90 \times 10^{-13}$ |
| $1.0 \times 10^{-7}$ | 6.94 | $3.36 \times 10^{-09}$ | $5.71 \times 10^{-12}$ | $5.90 \times 10^{-09}$ | $1.90 \times 10^{-12}$ |
| $1.0 \times 10^{-6}$ | 6.81 | $3.36 \times 10^{-08}$ | $5.71 \times 10^{-11}$ | $9.16 \times 10^{-08}$ | $3.30 \times 10^{-11}$ |
| $1.0 \times 10^{-5}$ | 6.42 | $3.36 \times 10^{-07}$ | $5.71 \times 10^{-09}$ | $3.78 \times 10^{-07}$ | $4.63 \times 10^{-11}$ |
| $1.0 \times 10^{-4}$ | 5.92 | $3.36 \times 10^{-06}$ | $5.71 \times 10^{-09}$ | $1.19 \times 10^{-06}$ | $5.67 \times 10^{-11}$ |
| $3.5 \times 10^{-4}$ | 5.65 | $1.18 \times 10^{-05}$ | $2.00 \times 10^{-08}$ | $2.23 \times 10^{-06}$ | $6.60 \times 10^{-11}$ |
| $1.0 \times 10^{-3}$ | 5.42 | $3.36 \times 10^{-05}$ | $5.71 \times 10^{-08}$ | $3.78 \times 10^{-06}$ | $5.61 \times 10^{-11}$ |
| $1.0 \times 10^{-2}$ | 4.92 | $3.36 \times 10^{-04}$ | $5.71 \times 10^{-07}$ | $1.19 \times 10^{-05}$ | $5.61 \times 10^{-11}$ |
| $1.0 \times 10^{-1}$ | 4.42 | $3.36 \times 10^{-03}$ | $5.71 \times 10^{-06}$ | $3.78 \times 10^{-05}$ | $5.61 \times 10^{-11}$ |
| $1.0 \times 10^{+0}$ | 3.92 | $3.36 \times 10^{-02}$ | $5.71 \times 10^{-05}$ | $1.20 \times 10^{-04}$ | $5.61 \times 10^{-11}$ |
| $2.5 \times 10^{+0}$ | 3.72 | $8.40 \times 10^{-02}$ | $1.43 \times 10^{-04}$ | $1.89 \times 10^{-04}$ | $5.61 \times 10^{-11}$ |
| $1.0 \times 10^{+1}$ | 3.42 | $3.36 \times 10^{-01}$ | $5.71 \times 10^{-04}$ | $3.78 \times 10^{-04}$ | $5.61 \times 10^{-11}$ |

As demonstrated in Table 2, $CO_2$ pressures between 1-10 atmospheres correspond to pH values as low as 3.42. Thus, acidification of aqueous culture media with $CO_2$ pressures greater than 2.5 atmospheres can, for example, reduce pH values to less than 4.0.

It is understood that modifications which do not substantially affect the activity of the various embodiments of this invention are also provided within the definition of the invention provided herein. Accordingly, the following examples are intended to illustrate but not limit the present invention.

EXAMPLES

Example I. Exemplary Pathways for Producing 2H3M4OP

This example describes an exemplary pathway for producing the terephthalic acid (PTA) precursor 2H3M4OP.

The precursor to the p-toluate and PTA pathways is 2H3M4OP. FIG. 1 shows a pathway from erythrose-4-phosphate to 2H3M4OP. The first two steps of the pathway employ enzymes of P5C biosynthesis. In the first step, oxidation of erythrose-4-phosphate to 4-phosphoerythronate is catalyzed by erythrose-4-phosphate dehydrogenase (EC 1.2.1.72). In step B, 4-phosphoerythronate is further oxidized to 2-oxo-3-hydroxy-4-phosphobutanoate by 4-phosphoerythronate dehydrogenase (EC 1.1.1.290). The next three steps of the pathway are analogous to the isoleucine biosynthesis pathway comprising a synthase, a ketol-acid reductoisomerase and a diol dehydratase. In step C, a 2-acetyl-2,3-dihydroxy-4-phosphobutanoate synthase converts pyruvate and 2-oxo-3-hydroxy-4-phosphobutanoate to 2-acetyl-2,3-dihydroxy-4-phosphobutanoate, releasing $CO_2$. This intermediate is then converted to 2,3,4-trihydroxy-3-methyl-5-phosphopentanoate by a reductoisomerase. Dehydration by a diol dehydratase forms the 2H3M4OP precursor, 4-hydroxy-3-methyl-2-oxo-5-phosphopentanoate. 2H3M4OP is then formed by decarboxylation of the ketoacid.

Pathways from 4,5-dihydroxy-2-oxopentanoate to 2H3M4OP are depicted in FIG. 2. 4,5-dihydroxy-2-oxopentanoate is derived from sugars such as arabinose and xylose. It can also be formed enzymatically by condensation of pyruvate and glycolaldehyde by aldolase enzymes such as 2-dehydro-3-deoxypentonate aldolase, 2-dehydro-3-deoxyglucarate aldolase, or other enzymes in EC class 4.1.2 or 4.1.3. In one 2H3M4OP pathway, 4,5-dihydroxy-2-oxopentanoate is converted to 4,5-dihydroxy-3-methyl-2-oxopentanoate by a methyltransferase (step A). The methylated product is then phosphorylated and decarboxylated (steps B/C). In an alternate pathway, the 4,5-dihydroxy-2-oxopentanoate substrate is phosphorylated to 4-hydroxy-2-oxo-5-phosphopentanoate (step D), then methylated by a methyltransferase (step E) to the 4-hydroxy-3-methyl-2-oxo-5-phosphopentanoate intermediate. Both pathways share the final decarboxylation of 4-hydroxy-3-methyl-2-oxo-5-phosphopentanoate to 2H3M4OP.

Enzyme Candidates

| EC Class | Description | Pathway step |
|---|---|---|
| 1.1.1.a | Oxidoreductase (alcohol to oxo) | 1B |
| 1.1.1.b | Ketol-acid reductoisomerase | 1D |
| 1.2.1.a | Oxidoreductase (aldehyde to acid) | 1A |
| 2.2.1.a | Synthase | 1C |
| 2.7.1.a | Kinase | 2B, 2D |
| 4.1.1.a | Decarboxylase | 1F, 2C |
| 4.2.1.b | Diol dehydratase | 1E |
| No EC | Methyltransferase | 2A, 2E |

EC 1.1.1.a

The NAD(P)+ dependent oxidation of erythronate-4-phosphate to 2-oxo-3-hydroxy-4-phosphobutanoate is catalyzed by 4-phosphoerythronate dehydrogenase (Step 1B, EC 1.1.1.290). This enzyme, encoded by the pdxB gene of *E. coli*, participates in pyridoxine biosynthesis (Zhao et al, *J Bacteriol* 177:2804-12 (1995)). An analogous enzyme is encoded by pdxB of *Pseudomonas aeruginosa* (Ha et. al, *J Mol Biol* 366:1294-1304 (2007)). The *E. coli* and *P. aeruginosa* enzymes utilize NAD+ as a cofactor. The pdxR gene from *Sinorhizobium melitoti* utilizes FAD+ as a cofactor (Hoshino et al, WO/2004/029250). Alcohol dehydrogenases that convert 2-hydroxyacids to 2-ketoacids, such as malate dehydrogenase (mdh) and lactate dehydrogenase (ldhA) of *E. coli*, are also suitable candidates. The lactate dehydrogenase from *Ralstonia eutropha* has been shown to demonstrate high activities on 2-ketoacids of various chain lengths includings lactate, 2-oxobutyrate, 2-oxopentanoate and 2-oxoglutarate (Steinbuchel et al., *Eur. J. Biochem.* 130:329-334 (1983)).

| Gene | Accession No. | GI No. | Organism |
|---|---|---|---|
| pdxB | NP_416823.1 | 16130255 | *Escherichia coli* |
| pdxB | Q9I3W9.1 | 46396520 | *Pseudomonas aeruginosa* |
| pdxR | AEH77803.1 | 336031871 | *Sinorhizobium melitoti* |
| mdh | AAC76268.1 | 1789632 | *Escherichia coli* |

| Gene | Accession No. | GI No. | Organism |
|------|---------------|--------|----------|
| ldhA | NP_415898.1 | 16129341 | *Escherichia coli* |
| ldh | YP_725182.1 | 113866693 | *Ralstonia eutropha* |

EC 1.1.1.b

The reduction and isomerization of 2-acetyl-2,3-dihydroxy-4-phosphobutanoate to 2,3,4-trihydroxy-3-methyl-5-phosphopentanoate is catalyzed by a bifunctional enzyme with 2-acetyl-2,3-dihydroxy-4-phosphobutanoate reductoisomerase activity (Step 1D). An analogous transformation is catalyzed by ketol-acid reductoisomerase (EC 1.1.1.86), an enzyme involved in branched chain amino acid biosynthesis. This enzyme, encoded by ilvC of *Escherichia coli*, is active on multiple substrates including 2-hydroxy-2-methyl-3-oxobutanoate, 2,3-dihydroxy-3-methylpentanoate and 2,3-dihydroxy-3-isopentanoate. Crystal structure of enzymes from *E. coli* and *Pseudomonas aeruginosa* are available (Tyagi et al., *Prot Sci* 14:3089-3100 (2005); Ahn et al., *J Mol Biol* 328:505-15 (2003)). Additional candidates are ilvC of *C. glutamicum* (Lewal et al, *J Biotechnol* 104:241-52 (2003)) and ilv5p of *Saccharomyces cerevisiae* (Omura, *Appl Microbiol Biotechnol* 78:503-13 (2008)).

| Gene | Accession No. | GI No. | Organism |
|------|---------------|--------|----------|
| ilvC | NP_418222.1 | 16131632 | *Escherichia coli* |
| ilvC | YP_793157.1 | 116052840 | *Pseudomonas aeruginosa* |
| ilvC | EHE83601.1 | 354510679 | *Corynebacterium glutamicum* |
| Ilv5p | NP_013459.1 | 6323387 | *Saccharomyces cerevisiae* |

EC 1.2.1.a

The oxidation of erythrose-4-phosphate to 4-phosphoerythronate is catalyzed by an oxidoreductase that converts an aldehyde to an acid. An enzyme with this activity is erythrose-4-phosphate dehydrogenase (EC 1.2.1.72). An NAD+ dependent erythrose-4-dehydrogenase is encoded by the epd gene of *E. coli* (Yang et al, *J Bacteriol* 180:4294-99 (1998)). A similar enzyme has been characterized in *Vibrio cholera* (Carroll et al, *J Bacteriol* 179:293-6 (1997)). Additional candidates are NAD+-dependent aldehyde dehydrogenases (EC 1.2.1.-) and NAD(P)+ dependent glyceraldehyde-3-phosphate dehydrogenases (EC 1.2.1.3 and 1.2.1.9). Two aldehyde dehydrogenases found in human liver, ALDH-1 and ALDH-2, have broad substrate ranges for a variety of aliphatic, aromatic and polycyclic aldehydes (Klyosov, *Biochemistry* 35:4457-4467 (1996a)). Active ALDH-2 has been efficiently expressed in *E. coli* using the GroEL proteins as chaperonins (Lee et al., *Biochem. Biophys. Res. Commun.* 298:216-224 (2002)). The rat mitochondrial aldehyde dehydrogenase also has a broad substrate range (Siew et al., *Arch. Biochem. Biophys.* 176:638-649 (1976)). The NAD+ dependent gapN gene of *Thermoproteus tenax* oxidizes glyceraldehyde-3-phosphate to its corresponding acid (Brunner et al, *J Biol Chem* 273:6149-56 (1998)). An exemplary NADP+ dependent glyceraldehyde-3-phosphate dehydrogenase is the GAPN gene product of *Arabidopsis thaliana* (Rius et al *Plant Mol Biol* 61:945-57 (2006))

| Gene | Accession No. | GI No. | Organism |
|------|---------------|--------|----------|
| epd | NP_417402.1 | 16130828 | *Escherichia coli* |
| epd | YP_001216003.2 | 229259769 | *Vibrio cholera* |
| ALDH-2 | P05091.2 | 118504 | *Homo sapiens* |
| ALDH-2 | NP_115792.1 | 14192933 | *Rattus norvegicus* |
| gapN | CAA71651.1 | 3059159 | *Thermoproteus tenax* |
| GAPN | ABB83822.1 | 82570696 | *Arabidopsis thaliana* |

EC 2.2.1.a

Formation of 2-acetyl-2,3-dihydroxy-4-phosphobutanoate in Step 1C is catalyzed by a synthase enzyme in EC class 2.2.1. A suitable enzyme for catalyzing this transformation is acetohydroxyacid synthase (EC 2.2.1.6), which condenses pyruvate and 2-oxobutanoate to 2-aceto-2-hydroxybutanoate and carbon dioxide. Alternately, two pyruvates are condensed forming acetolactate. The enzyme operates in branched chain amino acid biosynthesis pathways. Two isozymes are active in *E. coli*: ilvBN and ilvHI (Vyazmensky et al Biochem, 35:10339-46 (1996); Engel et al, Biotechnol bioeng 88:825-31 (2004)). The IlvBN enzyme has activity on a broad range of aldehyde substrates in vitro. The *Methanococcus aeolicus* ilvBN gene product is similar to the *E. coli* IlvBN enzyme (Xing et al, *J Bacteriol* 176:1207-13 (1994)). The acetolactate synthase from *Bacillus subtilis* (AlsS), which naturally catalyzes the condensation of two molecules of pyruvate to form 2-acetolactate, is also able to catalyze the decarboxylation of 2-ketoisovalerate like KDC both in vivo and in vitro (Atsumi and Liao, *AEM* 75:6306-11 (2009)).

| Gene | Accession No. | GI No. | Organism |
|------|---------------|--------|----------|
| ilvB | NP_418127.1 | 16131541 | *Escherichia coli* |
| ilvN | NP_418126.1 | 16131540 | *Escherichia coli* |
| ilvH | NP_414620.1 | 16128071 | *Escherichia coli* |
| ilvI | YP_025294.2 | 90111084 | *Escherichia coli* |
| ilvB | AAB53488.1 | 2065479 | *Methanococcus aeolicus* |
| ilvN | AAB53489.1 | 2065480 | *Methanococcus aeolicus* |
| alsS | Q04789.3 | 239938889 | *Bacillus subtilis* |

EC 2.7.1.a

Kinases catalyze the ATP-dependent transfer of a phosphate group to an alcohol. Kinase enzymes are required to catalyze the phosphorylation of 4,5-dihydroxy-3-methyl-2-oxopentanoate (Step 2B) and 4,5-dihydroxy-2-oxopentanoate (Step 2D). The enzymes described below naturally possess such activity or can be engineered to exhibit this activity. Kinases that catalyze the transfer of a phosphate group to an alcohol group are members of the EC 2.7.1 enzyme class. The table below lists several useful kinase enzymes in the EC 2.7.1 enzyme class.

| Enzyme Commission Number | Enzyme Name |
|--------------------------|-------------|
| 2.7.1.1 | hexokinase |
| 2.7.1.2 | glucokinase |
| 2.7.1.3 | ketohexokinase |
| 2.7.1.4 | fructokinase |
| 2.7.1.5 | rhamnulokinase |
| 2.7.1.6 | galactokinase |
| 2.7.1.7 | mannokinase |
| 2.7.1.8 | glucosamine kinase |
| 2.7.1.10 | phosphoglucokinase |
| 2.7.1.11 | 6-phosphofructokinase |
| 2.7.1.12 | gluconokinase |
| 2.7.1.13 | dehydrogluconokinase |
| 2.7.1.14 | sedoheptulokinase |

| Enzyme Commission Number | Enzyme Name |
| --- | --- |
| 2.7.1.15 | ribokinase |
| 2.7.1.16 | ribulokinase |
| 2.7.1.17 | xylulokinase |
| 2.7.1.18 | phosphoribokinase |
| 2.7.1.19 | phosphoribulokinase |
| 2.7.1.20 | adenosine kinase |
| 2.7.1.21 | thymidine kinase |
| 2.7.1.22 | ribosylnicotinamide kinase |
| 2.7.1.23 | NAD+ kinase |
| 2.7.1.24 | dephospho-CoA kinase |
| 2.7.1.25 | adenylyl-sulfate kinase |
| 2.7.1.26 | riboflavin kinase |
| 2.7.1.27 | erythritol kinase |
| 2.7.1.28 | triokinase |
| 2.7.1.29 | glycerone kinase |
| 2.7.1.30 | glycerol kinase |
| 2.7.1.31 | glycerate kinase |
| 2.7.1.32 | choline kinase |
| 2.7.1.33 | pantothenate kinase |
| 2.7.1.34 | pantetheine kinase |
| 2.7.1.35 | pyridoxal kinase |
| 2.7.1.36 | mevalonate kinase |
| 2.7.1.39 | homoserine kinase |
| 2.7.1.40 | pyruvate kinase |
| 2.7.1.41 | glucose-1-phosphate phosphodismutase |
| 2.7.1.42 | riboflavin phosphotransferase |
| 2.7.1.43 | glucuronokinase |
| 2.7.1.44 | galacturonokinase |
| 2.7.1.45 | 2-dehydro-3-deoxygluconokinase |
| 2.7.1.46 | L-arabinokinase |
| 2.7.1.47 | D-ribulokinase |
| 2.7.1.48 | uridine kinase |
| 2.7.1.49 | hydroxymethylpyrimidine kinase |
| 2.7.1.50 | hydroxyethylthiazole kinase |
| 2.7.1.51 | L-fuculokinase |
| 2.7.1.52 | fucokinase |
| 2.7.1.53 | L-xylulokinase |
| 2.7.1.54 | D-arabinokinase |
| 2.7.1.55 | allose kinase |
| 2.7.1.56 | 1-phosphofructokinase |
| 2.7.1.58 | 2-dehydro-3-deoxygalactonokinase |
| 2.7.1.59 | N-acetylglucosamine kinase |
| 2.7.1.60 | N-acylmannosamine kinase |
| 2.7.1.61 | acyl-phosphate-hexose phosphotransferase |
| 2.7.1.62 | phosphoramidate-hexose phosphotransferase |
| 2.7.1.63 | polyphosphate-glucose phosphotransferase |
| 2.7.1.64 | inositol 3-kinase |
| 2.7.1.65 | scyllo-inosamine 4-kinase |
| 2.7.1.66 | undecaprenol kinase |
| 2.7.1.67 | 1-phosphatidylinositol 4-kinase |
| 2.7.1.68 | 1-phosphatidylinositol-4-phosphate 5-kinase |
| 2.7.1.69 | protein-Np-phosphohistidine-sugar phosphotransferase |
| 2.7.1.70 | identical to EC 2.7.1.37. |
| 2.7.1.71 | shikimate kinase |
| 2.7.1.72 | streptomycin 6-kinase |
| 2.7.1.73 | inosine kinase |
| 2.7.1.74 | deoxycytidine kinase |
| 2.7.1.76 | deoxyadenosine kinase |
| 2.7.1.77 | nucleoside phosphotransferase |
| 2.7.1.78 | polynucleotide 5'-hydroxyl-kinase |
| 2.7.1.79 | diphosphate-glycerol phosphotransferase |
| 2.7.1.80 | diphosphate-serine phosphotransferase |
| 2.7.1.81 | hydroxylysine kinase |
| 2.7.1.82 | ethanolamine kinase |
| 2.7.1.83 | pseudouridine kinase |
| 2.7.1.84 | alkylglycerone kinase |
| 2.7.1.85 | β-glucoside kinase |
| 2.7.1.86 | NADH kinase |
| 2.7.1.87 | streptomycin 3"-kinase |
| 2.7.1.88 | dihydrostreptomycin-6-phosphate 3'a-kinase |
| 2.7.1.89 | thiamine kinase |
| 2.7.1.90 | diphosphate-fructose-6-phosphate 1-phosphotransferase |
| 2.7.1.91 | sphinganine kinase |
| 2.7.1.92 | 5-dehydro-2-deoxygluconokinase |
| 2.7.1.93 | alkylglycerol kinase |
| 2.7.1.94 | acylglycerol kinase |
| 2.7.1.95 | kanamycin kinase |
| 2.7.1.100 | S-methyl-5-thioribose kinase |
| 2.7.1.101 | tagatose kinase |
| 2.7.1.102 | hamamelose kinase |
| 2.7.1.103 | viomycin kinase |
| 2.7.1.105 | 6-phosphofructo-2-kinase |
| 2.7.1.106 | glucose-1,6-bisphosphate synthase |
| 2.7.1.107 | diacylglycerol kinase |
| 2.7.1.108 | dolichol kinase |
| 2.7.1.113 | deoxyguanosine kinase |
| 2.7.1.114 | AMP-thymidine kinase |
| 2.7.1.118 | ADP-thymidine kinase |
| 2.7.1.119 | hygromycin-B 7"-O-kinase |
| 2.7.1.121 | phosphoenolpyruvate-glycerone phosphotransferase |
| 2.7.1.122 | xylitol kinase |
| 2.7.1.127 | inositol-trisphosphate 3-kinase |
| 2.7.1.130 | tetraacyldisaccharide 4'-kinase |
| 2.7.1.134 | inositol-tetrakisphosphate 1-kinase |
| 2.7.1.136 | macrolide 2'-kinase |
| 2.7.1.137 | phosphatidylinositol 3-kinase |
| 2.7.1.138 | ceramide kinase |
| 2.7.1.140 | inositol-tetrakisphosphate 5-kinase |
| 2.7.1.142 | glycerol-3-phosphate-glucose phosphotransferase |
| 2.7.1.143 | diphosphate-purine nucleoside kinase |
| 2.7.1.144 | tagatose-6-phosphate kinase |
| 2.7.1.145 | deoxynucleoside kinase |
| 2.7.1.146 | ADP-dependent phosphofructokinase |
| 2.7.1.147 | ADP-dependent glucokinase |
| 2.7.1.148 | 4-(cytidine 5'-diphospho)-2-C-methyl-D-erythritol kinase |
| 2.7.1.149 | 1-phosphatidylinositol-5-phosphate 4-kinase |
| 2.7.1.150 | 1-phosphatidylinositol-3-phosphate 5-kinase |
| 2.7.1.151 | inositol-polyphosphate multikinase |
| 2.7.1.153 | phosphatidylinositol-4,5-bisphosphate 3-kinase |
| 2.7.1.154 | phosphatidylinositol-4-phosphate 3-kinase |
| 2.7.1.156 | adenosylcobinamide kinase |
| 2.7.1.157 | N-acetylgalactosamine kinase |
| 2.7.1.158 | inositol-pentakisphosphate 2-kinase |
| 2.7.1.159 | inositol-1,3,4-trisphosphate 5/6-kinase |
| 2.7.1.160 | 2'-phosphotransferase |
| 2.7.1.161 | CTP-dependent riboflavin kinase |
| 2.7.1.162 | N-acetylhexosamine 1-kinase |
| 2.7.1.163 | hygromycin B 4-O-kinase |
| 2.7.1.164 | O-phosphoseryl-tRNASec kinase |

Particularly useful kinase enzymes for catalyzing steps 2B and 2D are mevalonate kinase, glycerol kinase, homoserine kinase, glycerate kinase and erythritol kinase. A good candidate for this step is mevalonate kinase (EC 2.7.1.36) that phosphorylates the terminal hydroxyl group of mevalonate. Some gene candidates for this step are erg12 from *S. cerevisiae*, mvk from *Methanocaldococcus jannaschi*, MVK from *Homo sapiens*, and mvk from *Arabidopsis thaliana* col.

| Protein | GenBank ID | GI Number | Organism |
| --- | --- | --- | --- |
| erg12 | CAA39359.1 | 3684 | Saccharomyces cerevisiae |
| mvk | Q58487.1 | 2497517 | Methanocaldococcus jannaschii |
| mvk | AAH16140.1 | 16359371 | Homo sapiens |
| mvk | NP_851084.1 | 30690651 | Arabidopsis thaliana |

Glycerol kinase also phosphorylates the terminal hydroxyl group in glycerol to form glycerol-3-phosphate. This reaction occurs in several species, including *Escherichia coli, Saccharomyces cerevisiae*, and *Thermotoga maritima*. The *E. coli* glycerol kinase has been shown to accept alternate substrates such as dihydroxyacetone and glyceraldehyde (Hayashi et al., *J Biol. Chem.* 242:1030-1035

(1967)). T, maritime has two glycerol kinases (Nelson et al., Nature 399:323-329 (1999)). Glycerol kinases have been shown to have a wide range of substrate specificity. Crans and Whiteside studied glycerol kinases from four different organisms (Escherichia coli, S. cerevisiae, Bacillus stearothermophilus, and Candida mycoderma) (Crans et al., J. Am. Chem. Soc. 107:7008-7018 (2010); Nelson et al., Nature 399:323-329 (1999)). They studied 66 different analogs of glycerol and concluded that the enzyme could accept a range of substituents in place of one terminal hydroxyl group and that the hydrogen atom at C2 could be replaced by a methyl group. Interestingly, the kinetic constants of the enzyme from all four organisms were very similar.

| Protein | GenBank ID | GI Number | Organism |
|---|---|---|---|
| glpK | AP_003883.1 | 89110103 | Escherichia coli |
| glpK1 | NP_228760.1 | 15642775 | Thermotoga maritime |
| glpK2 | NP_229230.1 | 15642775 | Thermotoga maritime |
| Gut1 | NP_011831.1 | 82795252 | Saccharomyces cerevisiae |

Homoserine kinase is another candidate kinase. This enzyme is present in a number of organisms including E. coli, Streptomyces sp, and S. cerevisiae. Homoserine kinase from E. coli has been shown to have activity on numerous substrates, including, L-2-amino,1,4-butanediol, aspartate semialdehyde, and 2-amino-5-hydroxyvalerate (Huo et al., Biochemistry 35:16180-16185 (1996); Huo et al., Arch. Biochem. Biophys. 330:373-379 (1996)). This enzyme can act on substrates where the carboxyl group at the alpha position has been replaced by an ester or by a hydroxymethyl group.

| Protein | GenBank ID | GI Number | Organism |
|---|---|---|---|
| thrB | BAB96580.2 | 85674277 | Escherichia coli |
| SACT1DRAFT_4809 | ZP_06280784.1 | 282871792 | Streptomyces sp. ACT-1 |
| Thr1 | AAA35154.1 | 172978 | Saccharomyces serevisiae |

The interconversion of 3-phosphoglycerate and glycerate is catalyzed by glycerate kinase (EC 2.7.1.31). Three classes of glycerate kinase have been identified. Enzymes in class I and II produce glycerate-2-phosphate, whereas the class III enzymes found in plants and yeast produce glycerate-3-phosphate (Bartsch et al., FEBS Lett. 582:3025-3028 (2008)). In a recent study, class III glycerate kinase enzymes from Saccharomyces cerevisiae, Oryza sativa and Arabidopsis thaliana were heterologously expressed in E. coli and characterized (Bartsch et al., FEBS Lett. 582:3025-3028 (2008)).

| Protein | GenBank ID | GI Number | Organism |
|---|---|---|---|
| glxK | AAC73616.1 | 1786724 | Escherichia coli |
| YGR205W | AAS56599.1 | 45270436 | Saccharomyces cerevisiae |
| Os01g0682500 | BAF05800.1 | 113533417 | Oryza sativa |
| At1g80380 | BAH57057.1 | 227204411 | Arabidopsis thaliana |

Erythritol is converted to erythritol-4-phosphate by the erythritol kinase. Erythritol kinase (EC 2.7.1.27) catalyzes the phosphorylation of erythritol. Erythritol kinase was characterized in erythritol utilizing bacteria such as Brucella abortus (Sperry et al., J Bacteriol. 121:619-630 (1975)). The eryA gene of Brucella abortus has been functionally expressed in Escherichia coli and the resultant EryA was shown to catalyze the ATP-dependent conversion of erythritol to erythritol-4-phosphate (Lillo et al., Bioorg. Med. Chem. Lett. 13:737-739 (2003)).

| Protein | GenBank ID | GI Number | Organism |
|---|---|---|---|
| eryA | Q8YCU8 | 81850596 | Brucella melitensis |
| eriA | Q92NH0 | 81774560 | Sinorhizobium meliloti |
| eryA | YP_001108625.1 | 134102964 | Saccharopolyspora erythraea NRRL 2338 |

EC 4.1.1.a

Decarboxylation of 4-hydroxy-3-methyl-2-oxo-5-phosphopentanoate to 2H3M4OP (Steps 1F and 2C) is catalyzed by a keto-acid decarboxylase. Although an enzyme with 2H3M4OP-forming activity has not been described in the literature, the decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase, phosphonopyruvate decarboxylase, sulfopyruvate decarboxylase, acetohydroxy acid synthase/acetolactate synthase, glyoxylate carboligase and indole pyruvate decarboxylase.

Branched chain alpha-ketoacid decarboxylase (BCKAD, EC 4.1.1.72) is a particularly useful enzyme for the invention, as the pathway substrate is also a branched alpha-ketoacid. This class of enzyme has been shown to decarboxylate a variety of compounds varying in chain length from 3 to 6 carbons (Oku et al., J Biol Chem. 263:18386-18396 (1988); Smit et al., Appl Environ Microbiol 71:303-311 (2005)). The BCKAD enzyme in Lactococcus lactis has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., Appl Environ Microbiol 71:303-311 (2005)). The enzyme has been structurally characterized (Berg et al., Science. 318:1782-1786 (2007)). Sequence alignments between the Lactococcus lactis enzyme and the pyruvate decarboxylase of Zymomonas mobilus indicate that the catalytic and substrate recognition residues are nearly identical (Siegert et al., Protein Eng Des Sel 18:345-357 (2005)), so this enzyme would be a promising candidate for directed engineering of substrate specificity. Several ketoacid decarboxylases of Saccharomyces cerevisiae catalyze the decarboxylation of branched substrates, including ARO10, PDC6, PDC5, PDC1 and THI3 (Dickenson et al, J Biol Chem 275:10937-42 (2000)). Yet another BCKAD enzyme is encoded by rv0853c of Mycobacterium tuberculosis (Werther et al, J Biol Chem 283:5344-54 (2008)). This enzyme is subject to allosteric activation by alpha-ketoacid substrates. Decarboxylation of alpha-ketoglutarate by a BCKA was detected in Bacillus subtilis; however, this activity was low (5%) relative to activity on other branched-chain substrates (Oku and Kaneda, J Biol Chem. 263:18386-18396 (1988)) and the gene encoding this enzyme has not been identified to date. Additional BCKA gene candidates can be identified by homology to the Lactococcus lactis protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria. Recombinant branched chain alpha-keto acid decarboxylase enzymes derived from the E1 subunits of the mitochondrial branched-chain keto acid dehydrogenase complex from *Homo sapiens* and *Bos taurus* have been cloned and functionally expressed in *E. coli* (Davie et al., *J. Biol. Chem.* 267:16601-16606 (1992); Wynn et al., *J. Biol. Chem.* 267:12400-12403 (1992); Wynn et al., *J. Biol. Chem.* 267:1881-1887 (1992)). In these studies, the authors found that co-expression of chaperonins GroEL and GroES enhanced the specific activity of the decarboxylase by 500-fold (Wynn et al., *J. Biol. Chem.* 267:12400-12403 (1992)).

| Protein | GenBank ID | GI Number | Organism |
| --- | --- | --- | --- |
| kdcA | AAS49166.1 | 44921617 | *Lactococcus lactis* |
| PDC6 | NP_010366.1 | 6320286 | *Saccharomyces cerevisiae* |
| PDC5 | NP_013235.1 | 6323163 | *Saccharomyces cerevisiae* |
| PDC1 | P06169 | 30923172 | *Saccharomyces cerevisiae* |
| ARO10 | NP_010668.1 | 6320588 | *Saccharomyces cerevisiae* |
| THI3 | NP_010203.1 | 6320123 | *Saccharomyces cerevisiae* |
| rv0853c | O53865.1 | 81343167 | *Mycobacterium tuberculosis* |
| BCKDHB | NP_898871.1 | 34101272 | *Homo sapiens* |
| BCKDHA | NP_000700.1 | 11386135 | *Homo sapiens* |
| BCKDHB | P21839 | 115502434 | *Bos taurus* |
| BCKDHA | P11178 | 129030 | *Bos taurus* |

Another class of enzymes suitable for decarboxylating a phosphorylated alpha-ketoacid such as 4-hydroxy-3-methyl-2-oxo-5-phosphopentanoate is phosphonopyruvate decarboxylase (EC 4.1.1.82). This enzyme catalyzes the decarboxylation of 3-phosphonopyruvate to 2-phosphonoacetaldehyde. Exemplary phosphonopyruvate decarboxylase enzymes are encoded by dhpF of *Streptomyces luridus*, ppd of *Streptomyces viridochromogenes*, fom2 of *Streptomyces wedmorensis* (Circello et al, *Chem Biol* 17:402-11 (2010); Blodgett et al, *FEMS Microbiol Lett* 163:149-57 (2005); Hidaka et al, *Mol Gen Genet* 249:274-80 (1995)). The *Bacteroides fragilis* enzyme, encoded by aepY, also decarboxylates pyruvate and sulfopyruvate (Zhang et al, *J Biol Chem* 278:41302-8 (2003)).

| Protein | GenBank ID | GI Number | Organism |
| --- | --- | --- | --- |
| dhpF | ACZ13457.1 | 268628095 | *Streptomyces luridus* |
| Ppd | CAJ14045.1 | 68697716 | *Streptomyces viridochromogenes* |
| Fom2 | BAA32496.1 | 1061008 | *Streptomyces wedmorensis* |
| aepY | AAG26466.1 | 11023509 | *Bacteroides fragilis* |

Other useful ketoacid decarboxylases include pyruvate decarboxylase enzymes such as the pdc gene product of *Zymomonas mobilis*. This enzyme has a broad substrate range and has been a subject of directed engineering studies to alter the affinity for different substrates (Siegert et al., *Protein Eng Des Sel* 18:345-357 (2005)). The crystal structure of this enzyme is available (Killenberg-Jabs et al., *Eur. J. Biochem.* 268:1698-1704 (2001)). The benzoylformate decarboxylase from *Pseudomonas putida* has a broad substrate range and has been the target of enzyme engineering studies (Polovnikova et al., 42:1820-1830 (2003); Hasson et al., 37:9918-9930 (1998)). Site-directed mutagenesis of two residues in the active site of the *Pseudomonas putida* enzyme altered the affinity (Km) of naturally and non-naturally occurring substrates (Siegert et al., *Protein Eng Des Sel* 18:345-357 (2005)). The properties of this enzyme have been further modified by directed engineering (Lingen et al., *Chembiochem.* 4:721-726 (2003); Lingen et al., *Protein Eng* 15:585-593 (2002)). The benzoylformate decarboxylase from *Pseudomonas aeruginosa*, encoded by mdlC, has also been characterized experimentally (Barrowman et al., 34:57-60 (1986)). Additional gene candidates from *Pseudomonas stutzeri, Pseudomonas fluorescens* and other organisms can be inferred by sequence homology or identified using a growth selection system developed in *Pseudomonas putida* (Henning et al., *Appl. Environ. Microbiol.* 72:7510-7517 (2006)). Alpha-ketoglutarate decarboxylases are also relevant to the invention. An exemplary KDC is encoded by kad in *Mycobacterium tuberculosis* (Tian et al., *PNAS* 102:10670-10675 (2005)). KDC enzyme activity has also been detected in several species of *rhizobia* including *Bradyrhizobium japonicum* and *Mesorhizobium loti* (Green et al., *J Bacteriol* 182:2838-2844 (2000)). A novel class of AKG decarboxylase enzymes has recently been identified in cyanobacteria such as *Synechococcus* sp. PCC 7002 and homologs (Zhang and Bryant, *Science* 334:1551-3 (2011)).

| Protein | GenBank ID | GI Number | Organism |
| --- | --- | --- | --- |
| pdc | P06672.1 | 118391 | *Zymomonas mobilis* |
| mdlC | P20906.2 | 3915757 | *Pseudomonas putida* |
| mdlC | Q9HUR2.1 | 81539678 | *Pseudomonas aeruginosa* |
| dpgB | ABN80423.1 | 126202187 | *Pseudomonas stutzeri* |
| ilvB-1 | YP_260581.1 | 70730840 | *Pseudomonas fluorescens* |
| kgd | O50463.4 | 160395583 | *Mycobacterium tuberculosis* |
| kgd | NP_767092.1 | 27375563 | *Bradyrhizobium japonicum* USDA110 |
| kgd | NP_105204.1 | 13473636 | *Mesorhizobium loti* |
| ilvB | ACB00744.1 | 169887030 | *Synechococcus* sp. PCC 7002 |

EC 4.2.1.a

Formation of 4-hydroxy-3-methyl-2-oxo-5-phosphopentanoate from 2,3,4-trihydroxy-3-methyl-5-phosphopentanoate (Step 1E) is catalyzed by a diol dehydratase enzyme in EC class 4.2.1. Exemplary diol dehydratase enzymes are listed in the table below.

| Enzyme Commission Number | Enzyme Name |
| --- | --- |
| 4.2.1.5 | arabinonate dehydratase |
| 4.2.1.6 | galactonate dehydratase |
| 4.2.1.7 | altronate dehydratase |
| 4.2.1.8 | mannonate dehydratase |
| 4.2.1.9 | dihydroxy-acid dehydratase |
| 4.2.1.12 | phosphogluconate dehydratase |
| 4.2.1.25 | L-arabinonate dehydratase |
| 4.2.1.28 | propanediol dehydratase |
| 4.2.1.30 | glycerol dehydratase |
| 4.2.1.32 | L(+)-tartrate dehydratase |
| 4.2.1.39 | gluconate dehydratase |
| 4.2.1.40 | glucarate dehydratase |
| 4.2.1.41 | 5-dehydro-4-deoxyglucarate dehydratase |
| 4.2.1.42 | galactarate dehydratase |
| 4.2.1.43 | 2-dehydro-3-deoxy-L-arabinonate dehydratase |
| 4.2.1.44 | myo-inosose-2 dehydratase |
| 4.2.1.45 | CDP-glucose 4,6-dehydratase |
| 4.2.1.46 | dTDP-glucose 4,6-dehydratase |
| 4.2.1.47 | GDP-mannose 4,6-dehydratase |
| 4.2.1.76 | UDP-glucose 4,6-dehydratase |
| 4.2.1.81 | D(−)-tartrate dehydratase |
| 4.2.1.82 | xylonate dehydratase |

| Enzyme Commission Number | Enzyme Name |
|---|---|
| 4.2.1.90 | L-rhamnonate dehydratase |
| 4.2.1.109 | methylthioribulose 1-phosphate dehydratase |

Particularly useful diol dehydratase enzymes include dihydroxy-acid dehydratase (EC 4.2.1.9), phosphogluconate dehydratase (EC 4.2.1.12) and arabonate dehydratase (EC 4.2.1.25). Dihydroxy-acid dehydratase (DHAD, EC 4.2.1.9) is a B12-independent enzyme participating in branched-chain amino acid biosynthesis. In its native role, it converts 2,3-dihydroxy-3-methylvalerate to 2-keto-3-methyl-valerate, a precursor of isoleucine. In valine biosynthesis the enzyme catalyzes the dehydration of 2,3-dihydroxy-isovalerate to 2-oxoisovalerate. The DHAD from *Sulfolobus solfataricus* has a broad substrate range and activity of a recombinant enzyme expressed in *E. coli* was demonstrated on a variety of aldonic acids (KIM et al., *J. Biochem.* 139:591-596 (2006)). The *S. solfataricus* enzyme is tolerant of oxygen unlike many diol dehydratase enzymes. The *E. coli* enzyme, encoded by ilvD, is sensitive to oxygen, which inactivates its iron-sulfur cluster (Flint et al., *J. Biol. Chem.* 268:14732-14742 (1993)). Similar enzymes have been characterized in *Neurospora crassa* (Altmiller et al., Arch. Biochem. Biophys. 138:160-170 (1970)), *Salmonella typhimurium* (Armstrong et al., Biochim. Biophys. Acta 498: 282-293 (1977)) and *Corynebacterium glutamicum* (Holatko et al, J Biotechnol 139:203-10 (2009)). Other groups have shown that the overexpression of one or more Aft proteins or homologs thereof improves DHAD activity (US Patent Application 2011/0183393. In *Saccharomyces cerevisiae*, the Aft1 and Aft2 proteins are transcriptional activators that regulate numerous proteins related to the acquisition, compartmentalization, and utilization of iron. Phosphogluconate dehydratase is another keto-acid forming diol dehydratase that is active on a phosphorylated substrate. This enzyme participates in the pentose phosphate pathway catalyzing the conversion of 6-phosphogluconate to 2-dehydro-3-deoxygluconate-6-phosphate. These enzymes are B12-independent and contain an Fe—S cluster in the active site. Exemplary enzymes are the edd gene products of *E. coli* (Egan et al, J Bacteriol 174:4638-46 (1992)), *Pseudomonas aeruginosa* (Cuskey et al, J Bacteriol 162:865-71 (1985)) and *Xanthomonas oryzae* (Kim et al, Biotechnol Lett 32:527-31 (2010)). Another suitable enzyme is arabonate dehydratase. A gene encoding this activity is araC of *Azospirillum brasilense* (Watanabe et al, J Biol Chem 287: 33521-36 (2006)). Additional diol dehydratase candidates are described in Example II.

| Protein | GenBank ID | GI Number | Organism |
|---|---|---|---|
| ilvD | NP_344419.1 | 15899814 | *Sulfolobus solfataricus* |
| ilvD | AAT48208.1 | 48994964 | *Escherichia coli* |
| ilvD | NP_462795.1 | 16767180 | *Salmonella typhimurium* |
| ilvD | XP_958280.1 | 85090149 | *Neurospora crassa* |
| ilvD | CAB57218.1 | 6010023 | *Corynebacterium glutamicum* |
| Aft1 | P22149.2 | 1168370 | *Saccharomyces cerevisiae* |
| Aft2 | Q08957.1 | 74583775 | *Saccharomyces cerevisiae* |
| edd | NP_416365.1 | 16129804 | *Escherichia coli* |
| edd | NP_251884.1 | 15598390 | *Pseudomonas aeruginosa* |
| edd | YP_001913412.1 | 188576483 | *Xanthomonas oryzae* |
| araC | BAE94269.1 | 95102048 | *Azospirillum brasilense* |

No EC

Step 2A depicts 4,5-dihydroxy-2-oxopentanoate methyltransferase which catalyzes the methylation of 4.5-dihydroxy-2-oxopentanoate to form 4,5-dihydroxy-3-methyl-2-oxopentanoate. A similar transformation is catalyzed by 4-hydroxy-2-oxo-5-phosphopentanoate methyltransferase in Step 2E. Although enzymes with these activities have not been identified to date, methyltransferase enzymes that react with similar substrates include alpha-ketoglutarate methyltransferase and keto-arginine methyltransferase. Alpha-ketoglutarate methyltransferase is catalyzed by the products of genes glmT from *Streptomyces coelicolor*, dptI from *Streptomyces roseosporus*, and lptI from *Streptomyces fradiae* (Mahlert et al., J. Am. Chem. Soc., 2007, 129 (39), 12011-12018). Keto-arginine methyltransferase is encoded by mrsA of *Pseudomonas syringae* (Braun et al, AEM 76:2500-8 (2010)).

| Protein | GenBank ID | GI Number | Organism |
|---|---|---|---|
| glmT | NP_627429.1 | 21221650 | *Streptomyces coelicolor* |
| dptI | ZP_04706744.1 | 239986080 | *Streptomyces roseosporus* |
| lptI | AAZ23087.1 | 71068232 | *Streptomyces fradiae* |
| mrsA | ACY54549.1 | 262342060 | *Pseudomonas syringae* |

Example II. Exemplary Pathway for Producing 2H3M4OP from Glyceraldehyde-3-Phosphate (G3P) and Pyruvate This example describes an exemplary pathway for producing the terephthalic acid (PTA) precursor 2H3M4OP.

The precursor to the p-toluate and PTA pathways is 2H3M4OP. This chemical can be derived from central metabolites glyceraldehyde-3-phosphate (G3P) and pyruvate in three enzymatic steps as shown in FIG. 3. The first two steps are native to *E. coli* and other organisms that utilize the methylerythritol phosphate (non-mevalonate) pathway for isoprenoid biosynthesis. Pyruvate and G3P are first condensed to form 1-deoxy-D-xylulose 5-phosphate (DXP) by DXP synthase. Subsequent reduction and rearrangement of the carbon backbone is catalyzed by DXP reductoisomerase. Finally, a novel diol dehydratase transforms 2-C-methyl-D-erythritol-4-phosphate to the p-toluate precursor 2H3M4OP.

A. 1-Deoxyxylulose-5-phosphate (DXP) Synthase

Pyruvate and G3P are condensed to form DXP by DXP synthase (EC 2.2.1.7). This enzyme catalyzes the first step in the non-mevalonate pathway of isoprenoid biosynthesis. The enzyme requires thiamine diphosphate as a cofactor, and also requires reduced FAD, although there is no net redox change. A crystal structure of the *E. coli* enzyme is available (Xiang et al., *J. Biol. Chem.* 282:2676-2682 (2007)). Other enzymes have been cloned and characterized in *M. tuberculosis* (Bailey et al., *Glycobiology* 12:813-820 (2002)) and *Agrobacterium tumefaciens* (Lee et al., *J. Biotechnol.* 128:555-566 (2007). DXP synthase enzymes from *B. subtilis* and *Synechocystis* sp. PCC 6803 were cloned into *E. coli* (Harker and Bramley, *FEBS Lett.* 448:115-119 (1999).

| Gene | GenBank Accession No. | GI No. | Organism |
|---|---|---|---|
| dxs | AAC73523.1 | 1786622 | Escherichia coli |
| dxs | P0A554.1 | 61222979 | M. tuberculosis |
| dxs11 | AAP56243.1 | 37903541 | Agrobacterium tumefaciens |
| dxs | P54523.1 | 1731052 | Bacillus subtilis |
| sll1945 | BAA17089.1 | 1652165 | Synechocystis sp. PCC 6803 |

B. 1-Deoxy-D-xylulose-5-phosphate Reductoisomerase (EC 1.1.1.267)

The NAD(P)H-dependent reduction and rearrangement of 1-deoxy-D-xylulose-5-phosphate (DXP) to 2-C-methyl-D-erythritol-4-phosphate is catalyzed by DXP reductoisomerase (DXR, EC 1.1.1.267) in the second step of the non-mevalonate pathway for isoprenoid biosynthesis. The NADPH-dependent E. coli enzyme is encoded by dxr (Takahashi et al., Proc. Natl. Acad. Sci. USA 95:9879-9884 (1998)). A recombinant enzyme from Arabidopsis thaliana was functionally expressed in E. coli (Carretero-Paulet et al., Plant Physiol. 129:1581-1591 (2002). DXR enzymes from Zymomonas mobilis and Mycobacterium tuberculosis have been characterized and crystal structures are available (Grolle et al., FEMS Microbiol. Lett. 191:131-137 (2000); Henriksson et al., Acta Crystallogr. D. Biol. Crystallogr. 62:807-813 (2006). Most characterized DXR enzymes are strictly NADPH dependent, but the enzymes from A. thaliana and M. tuberculosis react with NADH at a reduced rate (Argyrou and Blanchard, Biochemistry 43:4375-4384 (2004); Rohdich et al., FEBS J. 273:4446-4458 (2006)).

| Gene | GenBank Accession No. | GI No. | Organism |
|---|---|---|---|
| dxr | AAC73284.1 | 1786369 | Escherichia coli |
| dxr | AAF73140.1 | 8131928 | Arabisopsis thaliana |
| dxr | CAB60758.1 | 6434139 | Zymomonas mobilis |
| dxr | NP_217386.2 | 57117032 | Mycobacterium tuberculosis |

C. 2-C-Methyl-D-erythritol-4-phosphate Dehydratase

A diol dehydratase is required to convert 2-C-methyl-D-erythritol-4-phosphate into the p-toluate precursor (Altmiller and Wagner, Arch. Biochem. Biophys. 138:160-170 (1970)). Although this transformation has not been demonstrated experimentally, several enzymes catalyze similar transformations including dihydroxy-acid dehydratase (EC 4.2.1.9), propanediol dehydratase (EC 4.2.1.28), glycerol dehydratase (EC 4.2.1.30), myo-inositose dehydratase (EC 4.2.1.44), 2-keto-3-deoxyarabonate dehydratase (EC 4.2.1.43), phosphogluconate dehydratase (EC 4.2.1.12) and arabonate dehydratase. These enzymes are described in further detail below. Additional diol dehydratase enzyme candidates are described above in Example 1.

Diol dehydratase or propanediol dehydratase enzymes (EC 4.2.1.28) capable of converting the secondary diol 2,3-butanediol to 2-butanone are excellent candidates for this transformation. Adenosylcobalamin-dependent diol dehydratases contain alpha, beta and gamma subunits, which are all required for enzyme function. Exemplary gene candidates are found in Klebsiella pneumoniae (Tobimatsu et al., Biosci. Biotechnol. Biochem. 62:1774-1777 (1998); Toraya et al., Biochem. Biophys. Res. Commun. 69:475-480 (1976)), Salmonella typhimurium (Bobik et al., J. Bacteriol. 179:6633-6639 (1997)), Klebsiella oxytoca (Tobimatsu et al., J. Biol. Chem. 270:7142-7148 (1995)) and Lactobacillus collinoides (Sauvageot et al., FEMS Microbiol. Lett. 209: 69-74 (2002)). Methods for isolating diol dehydratase gene candidates in other organisms are well known in the art (see, for example, U.S. Pat. No. 5,686,276).

| Gene | GenBank Accession No. | GI No. | Organism |
|---|---|---|---|
| pddA | BAA08099.1 | 868006 | Klebsiella oxytoca |
| pddB | BAA08100.1 | 868007 | Klebsiella oxytoca |
| pddC | BAA08101.1 | 868008 | Klebsiella oxytoca |
| pduC | AAB84102.1 | 2587029 | Salmonella typhimurium |
| pduD | AAB84103.1 | 2587030 | Salmonella typhimurium |
| pduE | AAB84104.1 | 2587031 | Salmonella typhimurium |
| pduC | CAC82541.1 | 18857678 | Lactobacullus collinoides |
| pduD | CAC82542.1 | 18857679 | Lactobacullus collinoides |
| pduE | CAD01091.1 | 18857680 | Lactobacullus collinoides |
| pddA | AAC98384.1 | 4063702 | Klebsiella pneumoniae |
| pddB | AAC98385.1 | 4063703 | Klebsiella pneumoniae |
| pddC | AAC98386.1 | 4063704 | Klebsiella pneumoniae |

Enzymes in the glycerol dehydratase family (EC 4.2.1.30) can also be used to dehydrate 2-C-methyl-D-erythritol-4-phosphate. Exemplary gene candidates encoded by gldABC and dhaB123 in Klebsiella pneumoniae (WO 2008/137403) and (Toraya et al., Biochem. Biophys. Res. Commun. 69:475-480 (1976)), dhaBCE in Clostridium pasteuranum (Macis et al., FEMS Microbiol Lett. 164:21-28 (1998)) and dhaBCE in Citrobacter freundii (Seyfried et al., J. Bacteriol. 178:5793-5796 (1996)). Variants of the B12-dependent diol dehydratase from K. pneumoniae with 80- to 336-fold enhanced activity were recently engineered by introducing mutations in two residues of the beta subunit (Qi et al., J. Biotechnol. 144:43-50 (2009)). Diol dehydratase enzymes with reduced inactivation kinetics were developed by DuPont using error-prone PCR (WO 2004/056963).

| Gene | GenBank Accession No. | GI No. | Organism |
|---|---|---|---|
| gldA | AAB96343.1 | 1778022 | Klebsiella pneumoniae |
| gldB | AAB96344.1 | 1778023 | Klebsiella pneumoniae |
| gldC | AAB96345.1 | 1778024 | Klebsiella pneumoniae |
| dhaB1 | ABR78884.1 | 150956854 | Klebsiella pneumoniae |
| dhaB2 | ABR78883.1 | 150956853 | Klebsiella pneumoniae |
| dhaB3 | ABR78882.1 | 150956852 | Klebsiella pneumoniae |
| dhaB | AAC27922.1 | 3360389 | Clostridium pasteuranum |
| dhaC | AAC27923.1 | 3360390 | Clostridium pasteuranum |
| dhaE | AAC27924.1 | 3360391 | Clostridium pasteuranum |
| dhaB | P45514.1 | 1169287 | Citrobacter freundii |
| dhaC | AAB48851.1 | 1229154 | Citrobacter freundii |
| dhaE | AAB48852.1 | 1229155 | Citrobacter freundii |

If a B12-dependent diol dehydratase is utilized, heterologous expression of the corresponding reactivating factor is recommended. B12-dependent diol dehydratases are subject to mechanism-based suicide activation by substrates and some downstream products. Inactivation, caused by a tight association with inactive cobalamin, can be partially overcome by diol dehydratase reactivating factors in an ATP-dependent process. Regeneration of the B12 cofactor requires an additional ATP. Diol dehydratase regenerating factors are two-subunit proteins. Exemplary candidates are found in Klebsiella oxytoca (Mori et al., J. Biol. Chem. 272:32034-32041 (1997)), Salmonella typhimurium (Bobik et al., J. Bacteriol. 179:6633-6639 (1997); Chen et al., J. Bacteriol. 176:5474-5482 (1994)), Lactobacillus collinoides (Sauvageot et al., *FEMS Microbiol. Lett.* 209:69-74 (2002)), and *Klebsiella pneumonia* (WO 2008/137403).

| Gene | GenBank Accession No. | GI No. | Organism |
|---|---|---|---|
| ddrA | AAC15871.1 | 3115376 | *Klebsiella oxytoca* |
| ddrB | AAC15872.1 | 3115377 | *Klebsiella oxytoca* |
| pduG | AAL20947.1 | 16420573 | *Salmonella typhimurium* |
| pduH | AAL20948.1 | 16420574 | *Salmonella typhimurium* |
| pduG | YP_002236779 | 206579698 | *Klebsiella pneumonia* |
| pduH | YP_002236778 | 206579863 | *Klebsiella pneumonia* |
| pduG | CAD01092 | 29335724 | *Lactobacillus collinoides* |
| pduH | CAD01093 | 29335725 | *Lactobacillus collinoides* |

B12-independent diol dehydratase enzymes utilize S-adenosylmethionine (SAM) as a cofactor, function under strictly anaerobic conditions, and require activation by a specific activating enzyme (Frey et al., *Chem. Rev.* 103: 2129-2148 (2003)). The glycerol dehydrogenase and corresponding activating factor of *Clostridium butyricum*, encoded by dhaB1 and dhaB2, have been well-characterized (O'Brien et al., *Biochemistry* 43:4635-4645 (2004); Raynaud et al., *Proc. Natl. Acad. Sci USA* 100:5010-5015 (2003)). This enzyme was recently employed in a 1,3-propanediol overproducing strain of *E. coli* and was able to achieve very high titers of product (Tang et al., *Appl. Environ. Microbiol.* 75:1628-1634 (2009)). An additional B12-independent diol dehydratase enzyme and activating factor from *Roseburia inulinivorans* was shown to catalyze the conversion of 2,3-butanediol to 2-butanone (US publication 2009/09155870).

| Gene | GenBank Accession No. | GI No. | Organism |
|---|---|---|---|
| dhaB1 | AAM54728.1 | 27461255 | *Clostridium butyricum* |
| dhaB2 | AAM54729.1 | 27461256 | *Clostridium butyricum* |
| rdhtA | ABC25539.1 | 83596382 | *Roseburia inulinivorans* |
| rdhtB | ABC25540.1 | 83596383 | *Roseburia inulinivorans* |

Dihydroxy-acid dehydratase (DHAD, EC 4.2.1.9) is a B12-independent enzyme participating in branched-chain amino acid biosynthesis. In its native role, it converts 2,3-dihydroxy-3-methylvalerate to 2-keto-3-methyl-valerate, a precursor of isoleucine. In valine biosynthesis, the enzyme catalyzes the dehydration of 2,3-dihydroxy-isovalerate to 2-oxoisovalerate. The DHAD from *Sulfolobus solfataricus* has a broad substrate range, and activity of a recombinant enzyme expressed in *E. coli* was demonstrated on a variety of aldonic acids (Kim and Lee, *J. Biochem.* 139:591-596 (2006)). The *S. solfataricus* enzyme is tolerant of oxygen unlike many diol dehydratase enzymes. The *E. coli* enzyme, encoded by ilvD, is sensitive to oxygen, which inactivates its iron-sulfur cluster (Flint et al., *J. Biol. Chem.* 268:14732-14742 (1993)). Similar enzymes have been characterized in *Neurospora crassa* (Altmiller and Wagner, *Arch. Biochem. Biophys.* 138:160-170 (1970)) and *Salmonella typhimurium* (Armstrong et al., *Biochim. Biophys. Acta* 498:282-293 (1977)).

| Gene | GenBank Accession No. | GI No. | Organism |
|---|---|---|---|
| ilvD | NP_344419.1 | 15899814 | *Sulfolobus solfataricus* |
| ilvD | AAT48208.1 | 48994964 | *Escherichia coli* |
| ilvD | NP_462795.1 | 16767180 | *Salmonella typhimurium* |
| ilvD | XP_958280.1 | 85090149 | *Neurospora crassa* |

The diol dehydratase myo-inosose-2-dehydratase (EC 4.2.1.44) is another exemplary candidate. Myo-inosose is a six-membered ring containing adjacent alcohol groups. A purified enzyme encoding myo-inosose-2-dehydratase functionality has been studied in *Klebsiella aerogenes* in the context of myo-inositol degradation (Berman and Magasanik, *J. Biol. Chem.* 241:800-806 (1966)), but has not been associated with a gene to date. The myo-inosose-2-dehydratase of *Sinorhizobium fredii* was cloned and functionally expressed in *E. coli* (Yoshida et al., *Biosci. Biotechnol. Biochem.* 70:2957-2964 (2006)). A similar enzyme from *B. subtilis*, encoded by iolE, has also been studied (Yoshida et al., *Microbiology* 150:571-580 (2004)).

| Gene | GenBank Accession No. | GI No. | Organism |
|---|---|---|---|
| iolE | P42416.1 | 1176989 | *Bacillus subtilis* |
| iolE | AAX24114.1 | 60549621 | *Sinorhizobium fredii* |

2-Keto-3-deoxyarabonate dehydratase participates in arabinose degradation in *Azospirillum brasilense*, converting 2-keto-3-deoxyarabonate to alpha-ketoglutarate semialdehyde (Watanabe et al, *J Biol Chem* 287:33521-36 (2006)). Similar enzymes can be identified by sequence homology. Phosphogluconate dehydratase is a diol dehydratase that participates in the pentose phosphate pathway catalyzing the conversion of 6-phosphogluconate to 2-dehydro-3-deoxygluconate-6-phosphate. Phosphogluconate dehydratase enzymes are B12-independent and contain an Fe—S cluster in the active site. Exemplary enzymes are the edd gene products of *E. coli* (Egan et al, *J Bacteriol* 174:4638-46 (1992)), *Pseudomonas aeruginosa* (Cuskey et al, *J Bacteriol* 162:865-71 (1985)) and *Xanthomonas oryzae* (Kim et al, *Biotechnol Lett* 32:527-31 (2010)). Another suitable enzyme is arabonate dehydratase. A gene encoding this activity is araC of *Azospirillum brasilense* (Watanabe et al, *J Biol Chem* 287:33521-36 (2006)).

| Protein | GenBank ID | GI Number | Organism |
|---|---|---|---|
| araD | BAE94270.1 | 95102049 | *Azospirillum brasilense* |
| dapA | ZP_02907581.1 | 171318425 | *Burkholderia ambifaria* |
| BCAM2800 | P_002235400.1 | 206564637 | *Burkholderia cenocepacia* |
| edd | NP_416365.1 | 16129804 | *Escherichia coli* |
| edd | NP_251884.1 | 15598390 | *Pseudomonas aeruginosa* |
| edd | YP_001913412.1 | 188576483 | *Xanthomonas oryzae* |
| araC | BAE94269.1 | 95102048 | *Azospirillum brasilense* |

Example III. Exemplary Pathway for Synthesis of p-Toluate from 2H3M4OP by Shikimate Pathway Enzymes This example describes exemplary pathways for synthesis of p-toluate using shikimate pathway enzymes.

The chemical structure of p-toluate closely resembles p-hydroxybenzoate, a precursor of the electron carrier ubiquinone. 4-Hydroxybenzoate is synthesized from central metabolic precursors by enzymes in the shikimate pathway, found in bacteria, plants and fungi. The shikimate pathway is comprised of seven enzymatic steps that transform D-erythrose-4-phosphate (E4P) and phosphoenolpyruvate (PEP) to chorismate. Pathway enzymes include 2-dehydro-3-deoxyphosphoheptonate (DAHP) synthase, dehydroquinate (DHQ) synthase, DHQ dehydratase, shikimate dehydrogenase, shikimate kinase, 5-enolpyruvylshikimate-3-phosphate (EPSP) synthase and chorismate synthase. In the first step of the pathway, D-erythrose-4-phosphate and phosphoenolpyruvate are joined by DAHP synthase to form 3-deoxy-D-arabino-heptulosonate-7-phosphate. This compound is then dephosphorylated, dehydrated and reduced to form shikimate. Shikimate is converted to chorismate by the actions of three enzymes: shikimate kinase, 3-phosphoshikimate-2-carboxyvinyltransferase and chorismate synthase. Subsequent conversion of chorismate to 4-hydroxybenzoate is catalyzed by chorismate lyase.

The synthesis of p-toluate proceeds in an analogous manner as shown in FIG. 4. The pathway originates with PEP and 2H3M4OP, a compound analogous to E4P with a methyl group in place of the 3-hydroxyl group of E4P. The hydroxyl group of E4P does not directly participate in the chemistry of the shikimate pathway reactions, so the methyl-substituted 2H3M4OP precursor is expected to react as an alternate substrate. Directed or adaptive evolution can be used to improve preference for 2H3M4OP and downstream derivatives as substrates. Such methods are well-known in the art.

Strain engineering strategies for improving the efficiency of flux through shikimate pathway enzymes are also applicable here. The availability of the pathway precursor PEP can be increased by altering glucose transport systems (Yi et al., *Biotechnol. Prog.* 19:1450-1459 (2003)). 4-Hydroxybenzoate-overproducing strains were engineered to improve flux through the shikimate pathway by means of overexpression of a feedback-insensitive isozyme of 3-deoxy-D-arabinoheptulosonic acid-7-phosphate synthase (Barker and Frost, *Biotechnol. Bioeng.* 76:376-390 (2001)). Additionally, expression levels of shikimate pathway enzymes and chorismate lyase were enhanced. Similar strategies can be employed in a strain for overproducing p-toluate.

A. 2-Dehydro-3-deoxyphosphoheptonate Synthase (EC 2.5.1.54)

The condensation of D-erythrose-4-phosphate and phosphoenolpyruvate is catalyzed by 2-dehydro-3-deoxyphosphoheptonate (DAHP) synthase (EC 2.5.1.54). Three isozymes of this enzyme are encoded in the *E. coli* genome by aroG, aroF and aroH and are subject to feedback inhibition by phenylalanine, tyrosine and tryptophan, respectively. In wild-type cells grown on minimal medium, the aroG, aroF and aroH gene products contributed 80%, 20% and 1% of DAHP synthase activity, respectively (Hudson and Davidson, *J. Mol. Biol.* 180:1023-1051 (1984)). Two residues of AroG were found to relieve inhibition by phenylalanine (Kikuchi et al., *Appl. Environ. Microbiol.* 63:761-762 (1997)). The feedback inhibition of AroF by tyrosine was removed by a single base-pair change (Weaver and Herrmann, *J. Bacteriol.* 172:6581-6584 (1990)). The tyrosine-insensitive DAHP synthase was overexpressed in a 4-hydroxybenzoate-overproducing strain of *E. coli* (Barker and Frost, *Biotechnol. Bioeng.* 76:376-390 (2001)). The aroG gene product was shown to accept a variety of alternate 4- and 5-carbon length substrates (Sheflyan et al., *J. Am. Chem. Soc.* 120(43):11027-11032 (1998); Williamson et al., *Bioorg. Med. Chem. Lett.* 15:2339-2342 (2005)). The enzyme reacts efficiently with (3S)-2-deoxyerythrose-4-phosphate, a substrate analogous to D-erythrose-4-phosphate but lacking the alcohol at the 2-position (Williamson et al., supra 2005). Enzymes from *Helicobacter pylori* and *Pyrococcus furiosus* also accept this alternate substrate (Schofield et al., *Biochemistry* 44:11950-11962 (2005); Webby et al., *Biochem. J.* 390:223-230 2005)) and have been expressed in *E. coli*. An evolved variant of DAHP synthase, differing from the wild type *E. coli* AroG enzyme by 7 amino acids, was shown to exhibit a 60-fold improvement in Kcat/$K_M$ (Ran and Frost, *J. Am. Chem. Soc.* 129:6130-6139 (2007)).

| Gene | GenBank Accession No. | GI No. | Organism |
| --- | --- | --- | --- |
| aroG | AAC73841.1 | 1786969 | *Escherichia coli* |
| aroF | AAC75650.1 | 1788953 | *Escherichia coli* |
| aroH | AAC74774.1 | 1787996 | *Escherichia coli* |
| aroF | Q9ZMU5 | 81555637 | *Helicobacter pylori* |
| PF1690 | NP_579419.1 | 18978062 | *Pyrococcus furiosus* |

B. 3-Dehydroquinate Synthase (EC 4.2.3.4)

The dephosphorylation of substrate (2)(2,4-dihydroxy-5-methyl-6-[(phosphonooxy)methyl]oxane-2-carboxylate) to substrate (3)(1,3-dihydroxy-4-methylcyclohex-1-ene-1-carboxylate) as shown in FIG. 4 is analogous to the dephosphorylation of 3-deoxy-arabino-heptulonate-7-phosphate by 3-dehydroquinate synthase. The enzyme has been characterized in *E. coli* (Mehdi et al., *Methods Enzymol.* 142:306-314 (1987), *B. subtilis* (Hasan and Nester, *J. Biol. Chem.* 253:4999-5004 (1978)) and *Mycobacterium tuberculosis* H37Rv (de Mendonca et al., *J. Bacteriol.* 189:6246-6252 (2007)). The *E. coli* enzyme is subject to inhibition by L-tyrosine (Barker and Frost, *Biotechnol. Bioeng.* 76:376-390 2001)).

| Gene | GenBank Accession No. | GI No. | Organism |
| --- | --- | --- | --- |
| aroB | AAC76414.1 | 1789791 | *Escherichia coli* |
| aroB | NP_390151.1 | 16079327 | *Bacillus subtilis* |
| aroB | CAB06200.1 | 1781064 | *Mycobacterium tuberculosis* |

C. 3-Dehydroquinate Dehydratase (EC 4.2.1.10)

3-Dehydroquinate dehydratase, also termed 3-dehydroquinase (DHQase), naturally catalyzes the dehydration of 3-dehydroquinate to 3-dehydroshikimate, analogous to step C in the p-toluate pathway of FIG. 4. DHQase enzymes can be divided into two classes based on mechanism, stereochemistry and sequence homology (Gourley et al., *Nat. Struct. Biol.* 6:521-525. (1999)). Generally the type 1 enzymes are involved in biosynthesis, while the type 2 enzymes operate in the reverse (degradative) direction. Type 1 enzymes from *E. coli* (Kinghorn et al., *Gene* 14:73-80. 1981)), *Salmonella typhi* (Kinghorn et al., supra 1981; Servos et al., *J. Gen. Microbiol.* 137:147-152 (1991)) and *B. subtilis* (Warburg et al., *Gene* 32:57-66 1984)) have been cloned and characterized. Exemplary type II 3-dehydroquinate dehydratase enzymes are found in *Mycobacterium* tuberculosis, Streptomyces coelicolor (Evans et al., FEBS Lett. 530:24-30 (2002)) and Helicobacter pylori (Lee et al., Proteins 51:616-7 (2003)).

| Gene | GenBank Accession No. | GI No. | Organism |
|---|---|---|---|
| aroD | AAC74763.1 | 1787984 | Escherichia coli |
| aroD | P24670.2 | 17433709 | Salmonella typhi |
| aroC | NP_390189.1 | 16079365 | Bacillus subtilis |
| aroD | P0A4Z6.2 | 61219243 | Mycobacterium tuberculosis |
| aroQ | P15474.3 | 8039781 | Streptomyces coelicolor |
| aroQ | Q48255.2 | 2492957 | Helicobacter pylori |

D. Shikimate Dehydrogenase (EC 1.1.1.25)

Shikimate dehydrogenase catalyzes the NAD(P)H dependent reduction of 3-dehydroshikimate to shikimate, analogous to Step D of FIG. 4. The E. coli genome encodes two shikimate dehydrogenase paralogs with different cofactor specificities. The enzyme encoded by aroE is NADPH specific, whereas the ydiB gene product is a quinate/shikimate dehydrogenase which can utilize NADH (preferred) or NADPH as a cofactor (Michel et al., J. Biol. Chem. 278: 19463-19472 (2003). NADPH-dependent enzymes from Mycobacterium tuberculosis (Zhang et al., J. Biochem. Mol. Biol. 38:624-631 (2005)), Haemophilus influenzae (Ye et al., J. Bacteriol. 185:4144-4151 (2003)) and Helicobacter pylori (Han et al., FEBS J. 273:4682-4692 (2006)) have been functionally expressed in E. coli.

| Gene | GenBank Accession No. | GI No. | Organism |
|---|---|---|---|
| aroE | AAC76306.1 | 1789675 | Escherichia coli |
| ydiB | AAC74762.1 | 1787983 | Escherichia coli |
| aroE | NP_217068.1 | 15609689 | Mycobacterium tuberculosis |
| aroE | P43876.1 | 1168510 | Haemophilus influenzae |
| aroE | AAW22052.1 | 56684731 | Helicobacter pylori |

E. Shikimate Kinase (EC 2.7.1.71)

Shikimate kinase catalyzes the ATP-dependent phosphorylation of the 3-hydroxyl group of shikimate analogous to Step E of FIG. 4. Two shikimate kinase enzymes are encoded by aroK (SK1) and aroL (SK2) in E. coli (DeFeyter and Pittard, J. Bacteriol. 165:331-333 (1986); Lobner-Olesen and Marinus, J. Bacteriol. 174:525-529 (1992)). The Km of SK2, encoded by aroL, is 100-fold lower than that of SK1, indicating that this enzyme is responsible for aromatic biosynthesis (DeFeyter et al., supra 1986). Additional shikimate kinase enzymes from Mycobacterium tuberculosis (Gu et al., J. Mol. Biol. 319:779-789 (2002)); Oliveira et al., Protein Expr. Purif. 22:430-435 (2001)), Helicobacter pylori (Cheng et al., J. Bacteriol. 187:8156-8163 (2005)) and Erwinia chrysanthemi (Krell et al., Protein Sci. 10:1137-1149 (2001)) have been cloned in E. coli.

| Gene | GenBank Accession No. | GI No. | Organism |
|---|---|---|---|
| aroK | YP_026215.2 | 90111581 | Escherichia coli |
| aroL | NP_414922.1 | 16128373 | Escherichia coli |
| aroK | CAB06199.1 | 1781063 | Mycobacterium tuberculosis |
| aroK | NP_206956.1 | 15644786 | Helicobacter pylori |
| SK | CAA32883.1 | 42966 | Erwinia chrysanthemi |

F. 3-Phosphoshikimate-2-carboxyvinyltransferase (EC 2.5.1.19)

3-Phosphoshikimate-2-carboxyvinyltransferase, also known as 5-enolpyruvylshikimate-3-phosphate synthase (EPSPS), catalyzes the transfer of the enolpyruvyl moiety of phosphoenolpyruvate to the 5-hydroxyl of shikimate-3-phosphate. The enzyme is encoded by aroA in E. coli (Anderson et al., Biochemistry 27:1604-1610 (1988)). EPSPS enzymes from Mycobacterium tuberculosis (Oliveira et al., Protein Expr. Purif. 22:430-435 (2001)), Dunaliella salina (Yi et al., J. Microbiol. 45:153-157 (2007)) and Staphylococcus aureus (Priestman et al., FEBS Lett. 579:728-732 (2005)) have been cloned and functionally expressed in E. coli.

| Gene | GenBank Accession No. | GI No. | Organism |
|---|---|---|---|
| aroA | AAC73994.1 | 1787137 | Escherichia coli |
| aroA | AAA25356.1 | 149928 | Mycobacterium tuberculosis |
| aroA | AAA71897.1 | 152956 | Staphylococcus aureus |
| aroA | ABM68632.1 | 122937807 | Dunaliella salina |

G. Chorismate Synthase (EC 4.2.3.5)

Chorismate synthase is the seventh enzyme in the shikimate pathway, catalyzing the transformation of 5-enolpyruvylshikimate-3-phosphate to chorismate. The enzyme requires reduced flavin mononucleotide (FMN) as a cofactor, although the net reaction of the enzyme does not involve a redox change. In contrast to the enzyme found in plants and bacteria, the chorismate synthase in fungi is also able to reduce FMN at the expense of NADPH (Macheroux et al., Planta 207:325-334 (1999)). Representative monofunctional enzymes are encoded by aroC of E. coli (White et al., Biochem. J. 251:313-322 (1988)) and Streptococcus pneumoniae (Maclean and Ali, Structure 11:1499-1511 (2003)). Bifunctional fungal enzymes are found in Neurospora crassa (Kitzing et al., J. Biol. Chem. 276:42658-42666 (2001)) and Saccharomyces cerevisiae (Jones et al., Mol. Microbiol. 5:2143-2152 (1991)).

| Gene | GenBank Accession No. | GI No. | Organism |
|---|---|---|---|
| aroC | NP_416832.1 | 16130264 | Escherichia coli |
| aroC | ACH47980.1 | 197205483 | Streptococcus pneumoniae |
| U25818.1:19...1317 | AAC49056.1 | 976375 | Neurospora crassa |
| ARO2 | CAA42745.1 | 3387 | Saccharomyces cerevisiae |

H. Chorismate Lyase (EC 4.1.3.40)

Chorismate lyase catalyzes the first committed step in ubiquinone biosynthesis: the removal of pyruvate from chorismate to form 4-hydroxybenzoate. The enzymatic reaction is rate-limited by the slow release of the 4-hydroxybenzoate product (Gallagher et al., *Proteins* 44:304-311 (2001)), which is thought to play a role in delivery of 4-hydroxybenzoate to downstream membrane-bound enzymes. The chorismate lyase of *E. coli* was cloned and characterized and the enzyme has been crystallized (Gallagher et al., *supra* 2001; Siebert et al., *FEBS Lett.* 307:347-350 (1992)). Structural studies implicate the G90 residue as contributing to product inhibition (Smith et al., *Arch. Biochem. Biophys.* 445:72-80 (2006)). Modification of two surface-active cysteine residues reduced protein aggregation (Holden et al., *Biochim. Biophys. Acta* 1594:160-167 (2002)). A recombinant form of the *Mycobacterium tuberculosis* chorismate lyase was cloned and characterized in *E. coli* (Stadthagen et al., *J. Biol. Chem.* 280:40699-40706 2005)).

| Gene | GenBank Accession No. | GI No. | Organism |
| --- | --- | --- | --- |
| ubiC | AAC77009.2 | 87082361 | *Escherichia coli* |
| Rv2949c | NP_217465.1 | 15610086 | *Mycobacterium tuberculosis* |

B-F. Multifunctional AROM Protein

In most bacteria, the enzymes of the shikimate pathway are encoded by separate polypeptides. In microbial eukaryotes, five enzymatic functions are catalyzed by a polyfunctional protein encoded by a pentafunctional supergene (Campbell et al., *Int. J. Parasitol.* 34:5-13 (2004)). The multifunctional AROM protein complex catalyzes reactions analogous to reactions B-F of FIG. 4. The AROM protein complex has been characterized in fungi including *Aspergillus nidulans, Neurospora crassa, Saccharomyces cerevisiae* and *Pneumocystis carinii* (Banerji et al., *J. Gen. Microbiol.* 139:2901-2914 (1993); Charles et al., *Nucleic Acids Res.* 14:2201-2213 (1986); Coggins et al., *Methods Enzymol.* 142:325-341 (1987); Duncan, K., *Biochem. J.* 246:375-386 (1987)). Several components of AROM have been shown to function independently as individual polypeptides. For example, dehydroquinate synthase (DHQS) forms the amino-terminal domain of AROM, and can function independently when cloned into *E. coli* (Moore et al., *Biochem. J.* 301 (Pt 1):297-304 (1994)). Several crystal structures of AROM components from *Aspergillus nidulans* provide insight into the catalytic mechanism (Carpenter et al., *Nature* 394:299-302 (1998)).

| Gene | GenBank Accession No. | GI No. | Organism |
| --- | --- | --- | --- |
| AROM | P07547.3 | 238054389 | *Aspergillus nidulans* |
| AROM | P08566.1 | 114166 | *Saccharomyces cerevisiae* |
| AROM | P07547.3 | 238054389 | *Aspergillus nidulans* |
| AROM | Q12659.1 | 2492977 | *Pneumocystis carinii* |

Example IV. Exemplary Pathway for Enzymatic Transformation of p-Toluate to Terephthalic Acid This example describes exemplary pathways for conversion of p-toluate to terephthalic acid (PTA).

P-toluate can be further transformed to PTA by oxidation of the methyl group to an acid in three enzymatic steps as shown in FIG. 5. The pathway is comprised of a p-toluate methyl-monooxygenase reductase, a 4-carboxybenzyl alcohol dehydrogenase and a 4-carboxybenzyl aldehyde dehydrogenase. In the first step, p-toluate methyl-monooxygenase oxidizes p-toluate to 4-carboxybenzyl alcohol in the presence of $O_2$. The *Comamonas testosteroni* enzyme (tsaBM), which also reacts with 4-toluene sulfonate as a substrate, has been purified and characterized (Locher et al., *J. Bacteriol.* 173:3741-3748 (1991)). 4-Carboxybenzyl alcohol is subsequently converted to an aldehyde by 4-carboxybenzyl alcohol dehydrogenase (tsaC). The aldehyde to acid transformation is catalyzed by 4-carboxybenzaldehyde dehydrogenase (tsaD). Enzymes catalyzing these reactions are found in *Comamonas testosteroni* T-2, an organism capable of utilizing p-toluate as the sole source of carbon and energy (Junker et al., *J. Bacteriol.* 179:919-927 (1997)). Additional genes to transform p-toluate to PTA can be found by sequence homology, in particular to proteobacteria in the genera *Burkholderia, Alcaligenes, Pseudomonas, Shingomonas* and *Comamonas* (U.S. Pat. No. 6,187,569 and US publication 2003/0170836). Genbank identifiers associated with the *Comamonas testosteroni* enzymes are listed below.

| Gene | GenBank Accession No. | GI No. | Organism |
| --- | --- | --- | --- |
| tsaB | AAC44805.1 | 1790868 | *Comamonas testosteroni* |
| tsaM | AAC44804.1 | 1790867 | *Comamonas testosteroni* |
| tsaC | AAC44807.1 | 1790870 | *Comamonas testosteroni* |
| tsaD | AAC44808.1 | 1790871 | *Comamonas testosteroni* |

Example V. Exemplary Process for Production and Recovery of Terephthalic Acid

The following example describes an exemplary process for production and recovery of terephthalic acid from a culture medium, as exemplified and illustrated in FIG. 6.

Culturing the Non-Naturally Occurring Microbial Organism to Produce Terephthalate:

Sugars can be fermented in a culture medium at neutral pH using a non-naturally occurring microbial organism containing a functional terephthalate pathway. Under these conditions, terephthalate thus produced will be in the culture medium of the cells.

If conventional sugars are employed, cells can be removed by centrifugation or membrane filtration. If biomass is used as a primary feedstock, a pretreated stream of biomass can be introduced into the fermenter along with cellulolytic enzymes in order to engage in a simultaneous saccharification and fermentation process.

Ammonia can be used as a base to maintain pH at 7, in which case the fermentation process will produce diammonium terephthalate, which is soluble in the aqueous culture medium.

Following fermentation, once sufficient quantities of terephthalate are produced, the culture medium can be separated from any non-soluble materials by centrifugation or membrane filtration to provide a cell-free broth containing the terephthalate salt. Where biomass is used as a primary feedstock, both cells and any non-soluble lignocellulosic material remaining can be removed together through centrifugation or membrane filtration to provide a cell-free broth containing the terephthalate salt, which is soluble in the cell-free broth.

Lowering the pH with CO₂ to Precipitate the Terephthalic Acid:

The cell-free broth can be acidified by adding gaseous carbon dioxide ($CO_2$). The vessel can be pressurized in the range of 0.1 to 30 atm with $CO_2$ and allowed to stir at temperatures between 0° C. and 50° C. for up to 20 hours. Lowering the pH of the cell-free broth leads to the insoluble terephthalic acid precipitating from solution, where the resulting ammonium carbonate $((NH_4)_2CO_3)$ remains in solution.

Filtering and Recovering the Terephthalic Acid:

The crude terephthalic acid can be filtered from the solution and recovered. The remaining aqueous filtrate contains $(NH_4)_2CO_3$, and this solution can be heated to decompose $(NH_4)_2CO_3$ into $NH_3$ and $CO_2$ for separation, recovery, and recycling of both or either of these materials. Crude terephthalic acid solid can be recrystallized using standard techniques and solvents to afford purified terephthalic acid.

Using this exemplary process, a high predicted fermentation yield of up to 0.58 lb terephthalic acid/lb sugar may be obtained.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method for producing terephthalate, comprising culturing a non-naturally occurring *Escherichia coli* under conditions and for a sufficient period of time to produce terephthalate, wherein the non-naturally occurring *Escherichia coli* comprises:

a (2-hydroxy-3-methyl-4-oxobutoxy)phosphonate (2H3M4OP) pathway comprising at least one exogenous nucleic acid encoding a 2H3M4OP pathway enzyme expressed in a sufficient amount to produce 2H3M4OP, wherein said 2H3M4OP pathway comprises a pathway selected from:
   (1) 1A, IB, 1C, 1D, 1E and 1F;
   (2) 2A, 2B and 2C; and
   (3) 2D, 2E and 2C, wherein 1 A is an erythrose-4-phosphate dehydrogenase, wherein 1B is a 4-phosphoerythronate dehydrogenase, wherein 1C is a 2-acetyl-2,3-dihydroxy-4-phosphobutanoate synthase, wherein 1D is a 2-acetyl-2,3-dihydroxy-4-phosphobutanoate reductoisomerase, wherein 1E is a 2,3,4-trihydroxy-3-methyl-5-phosphopentanoate dehydratase, wherein 1F is a 4-hydroxy-3-methyl-2-oxo-5-phosphopentanoate decarboxylase, wherein 2A is a 4,5-dihydroxy-2-oxopentanoate methyltransferase, wherein 2B is a 4,5-dihydroxy-3-methyl-2-oxopentanoate kinase, wherein 2C is a 4-hydroxy-3-methyl-2-oxo-5-phosphopentanoate decarboxylase, wherein 2D is a 4,5-dihydroxy-2-oxopentanoate kinase, wherein 2E is a 4-hydroxy-2-oxo-5-phosphopentanoate methyltransferase;

a p-toluate pathway comprising at least one exogenous nucleic acid encoding a p-toluate pathway enzyme expressed in a sufficient amount to produce p-toluate, wherein said p-toluate pathway comprises 4A, 4B, 4C, 4D, 4E, 4F, 4G and 4H, wherein 4A is a 2-dehydro-3-deoxyphosphoheptonate synthase; wherein 4B is a 3-dehydroquinate synthase; wherein 4C is a 3-dehydroquinate dehydratase; wherein 4D is a shikimate dehydrogenase; wherein 4E is a shikimate kinase; wherein 4F is a 3-phosphoshikimate-2-carboxyvinyltransferase; wherein 4G is a chorismate synthase and wherein 4H is a chorismate lyase; and a terephthalate pathway comprising at least one exogenous nucleic acid encoding a terephthalate pathway enzyme expressed in a sufficient amount to produce terephthalate, wherein said terephthalate pathway comprises 5A, 5B and 5C, wherein 5A is a p-toluate methyl-monooxygenase reductase, wherein 5B is a 4-carboxybenzyl alcohol dehydrogenase and wherein 5C is a 4-carboxybenzyl aldehyde dehydrogenase.

\* \* \* \* \*